US010799369B2

(12) United States Patent
Trauner

(10) Patent No.: US 10,799,369 B2
(45) Date of Patent: Oct. 13, 2020

(54) BONE IMPLANT AUGMENT METHOD AND APPARATUS

(71) Applicant: Kenneth B Trauner, San Francisco, CA (US)

(72) Inventor: Kenneth B Trauner, San Francisco, CA (US)

(73) Assignee: Kenneth B. Trauner, San Francisco, CA (US)

( * ) Notice: Subject to any disclaimer, the term of this patent is extended or adjusted under 35 U.S.C. 154(b) by 128 days.

(21) Appl. No.: 15/582,380

(22) Filed: Apr. 28, 2017

(65) Prior Publication Data

US 2017/0296358 A1    Oct. 19, 2017

Related U.S. Application Data

(63) Continuation-in-part of application No. 15/059,511, filed on Mar. 3, 2016, now abandoned.

(Continued)

(51) Int. Cl.
*A61F 2/46* (2006.01)
*A61F 2/30* (2006.01)
*A61F 2/38* (2006.01)

(52) U.S. Cl.
CPC ........ *A61F 2/4601* (2013.01); *A61F 2/30734* (2013.01); *A61F 2/38* (2013.01); *A61F 2/3877* (2013.01); *A61F 2002/3008* (2013.01); *A61F 2002/30065* (2013.01); *A61F 2002/3082* (2013.01); *A61F 2002/3085* (2013.01); *A61F 2002/3096* (2013.01); *A61F 2002/30224* (2013.01); *A61F 2002/30242* (2013.01); *A61F 2002/30266* (2013.01); *A61F 2002/30299* (2013.01); *A61F 2002/30561* (2013.01); *A61F 2002/30579* (2013.01); *A61F 2002/30599* (2013.01); *A61F 2002/30616* (2013.01); *A61F 2002/30617* (2013.01); *A61F 2002/30736* (2013.01); *A61F 2002/30784* (2013.01); *A61F 2002/30841* (2013.01); *A61F 2002/4619* (2013.01); *A61F 2002/4631* (2013.01); *A61F 2310/00353* (2013.01); *A61F 2310/00952* (2013.01)

(58) Field of Classification Search
CPC ................ A61F 2/30734; A61F 2/4601; A61F 2002/30766
See application file for complete search history.

(56) References Cited

U.S. PATENT DOCUMENTS

2008/0050699 A1* 2/2008 Zhang .................. A61C 8/0012
   433/171
2012/0215311 A1* 8/2012 Parry .................. A61F 2/30734
   623/16.11

* cited by examiner

*Primary Examiner* — Bruce E Snow
*Assistant Examiner* — Melissa A Hoban
(74) *Attorney, Agent, or Firm* — Staniford Tomita LLP

(57) ABSTRACT

The strength of bone implant attached to a bone is improved by using hybrid inserts which have stems and wings having bone ingrowth surface features and caps having outer surfaces of cured polymethyl methacrylate (PMMA). The stems and wings of the hybrid inserts are inserted into living bone and the bone implant is attached to the hybrid inserts with PMMA cement. Over time, the bone grows into the bone ingrowth surface features. The bone ingrowth strengthens the bonding of the hybrid inserts and the bone implant with the bone over time. The hybrid inserts increase the shear, tensile and torque strength of the bone implants. Bone inserts that do not have ingrowth surface features loosen over time.

18 Claims, 38 Drawing Sheets

Related U.S. Application Data

(60) Provisional application No. 62/328,799, filed on Apr. 28, 2016, provisional application No. 62/237,018, filed on Oct. 5, 2015, provisional application No. 62/133,072, filed on Mar. 13, 2015, provisional application No. 62/128,732, filed on Mar. 5, 2015.

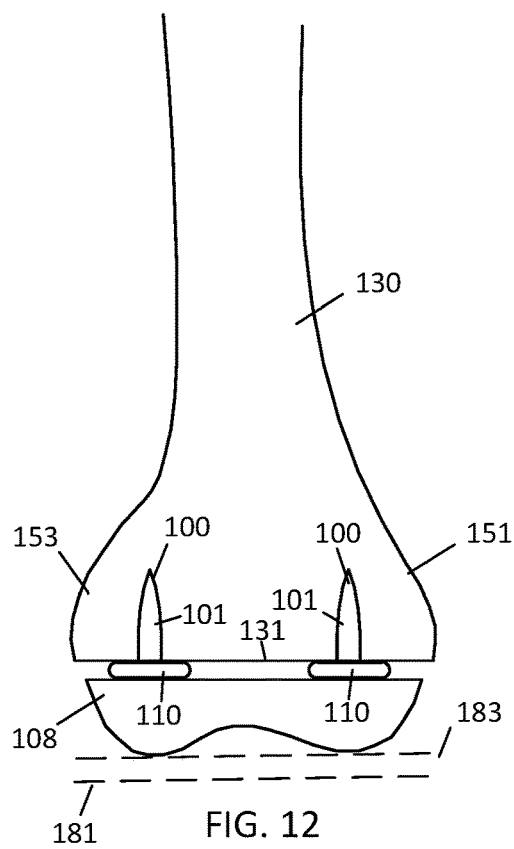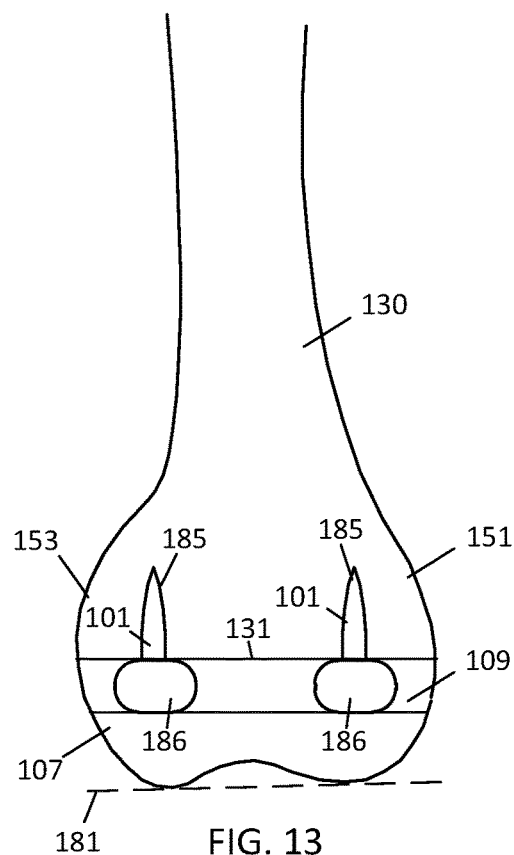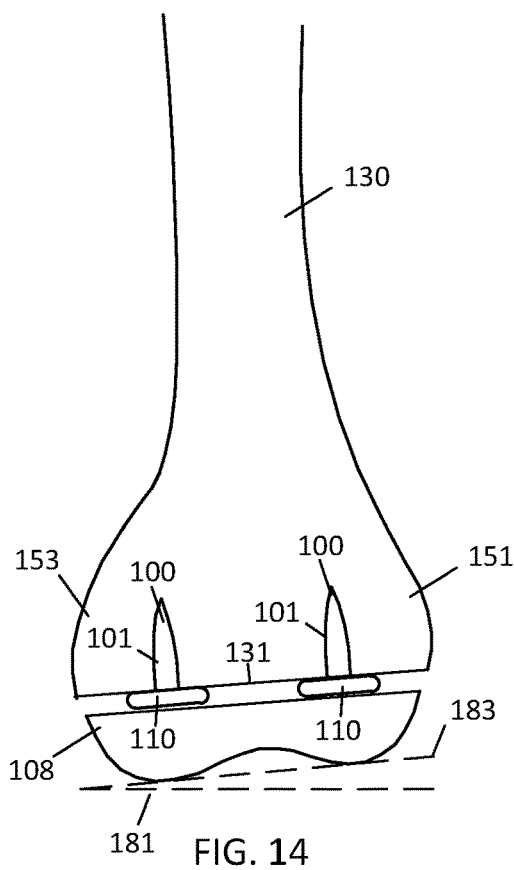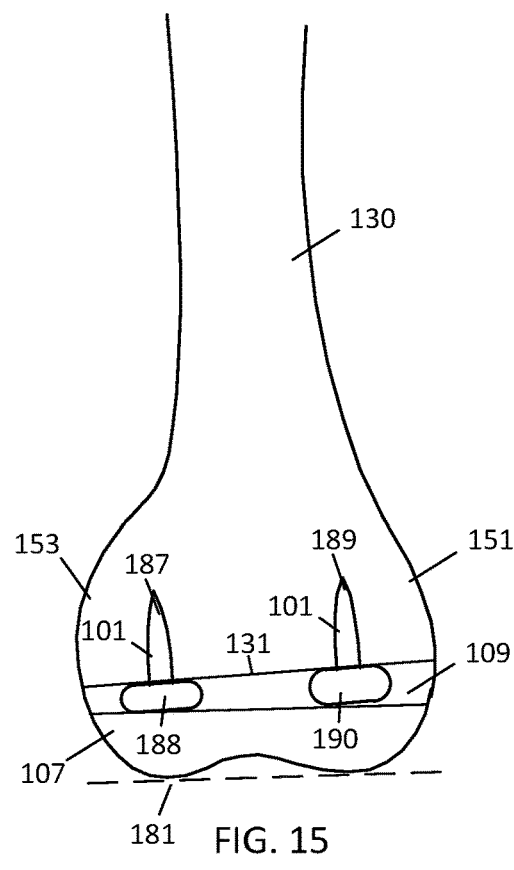

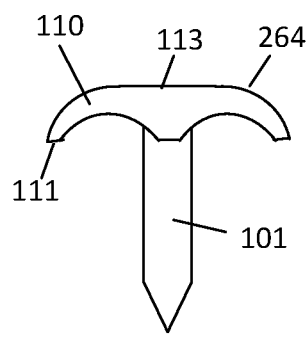
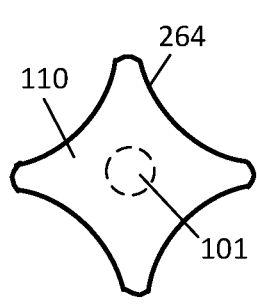
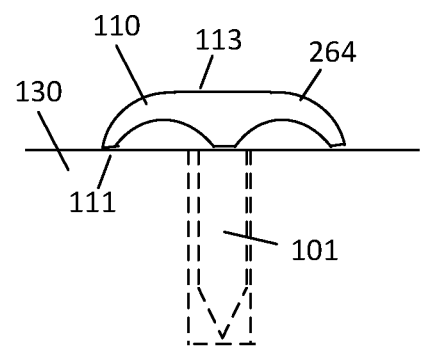
FIG. 35      FIG. 36      FIG. 37
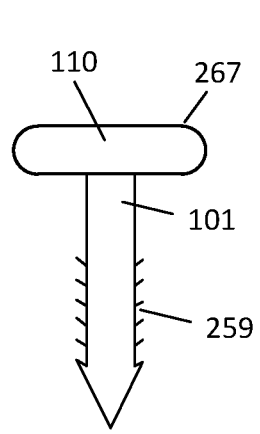
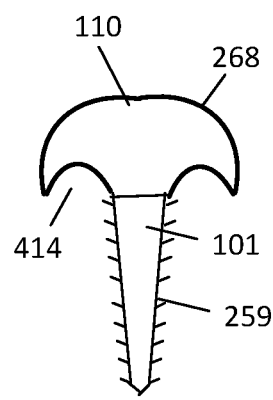
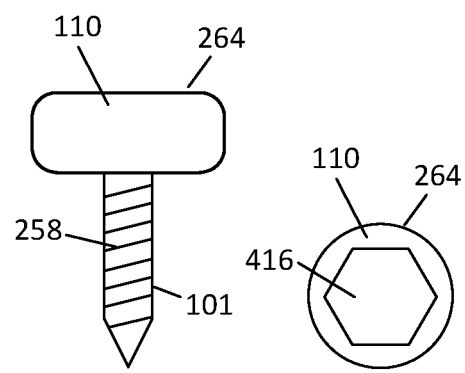
FIG. 38      FIG. 39      FIG. 40      FIG. 41

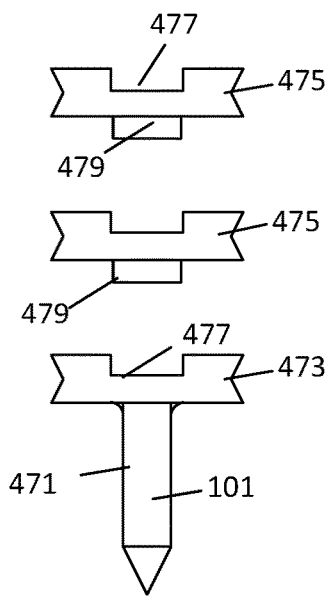
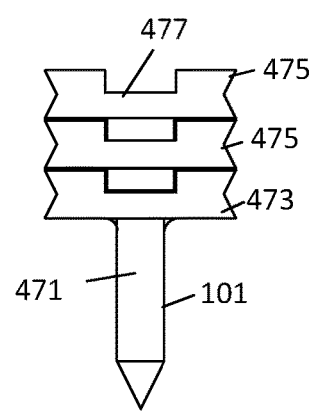
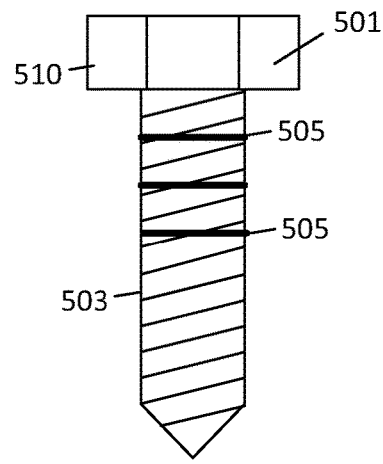
FIG. 75
FIG. 76
FIG. 77
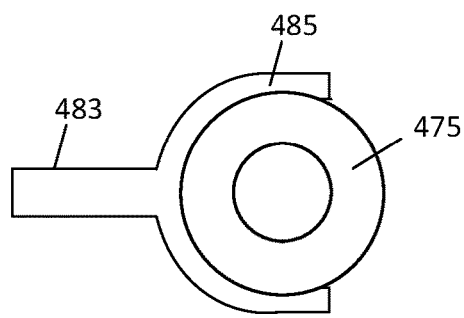
FIG. 78
FIG. 79
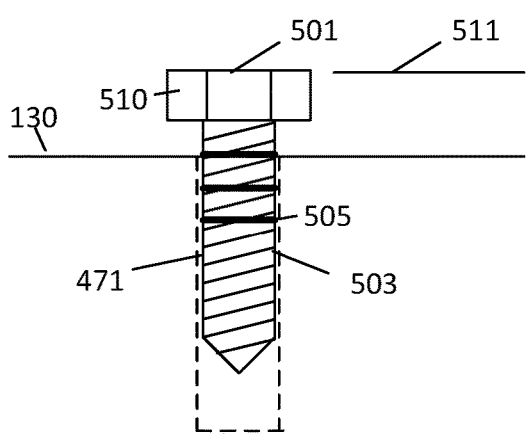
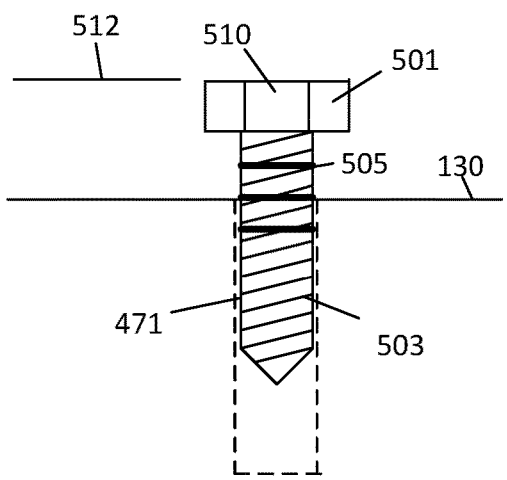
FIG. 80
FIG. 81

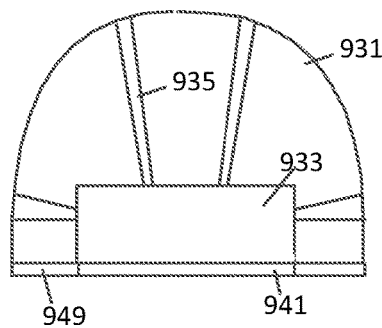
FIG. 141
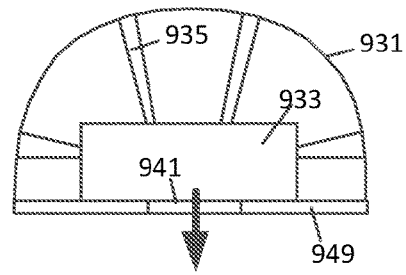
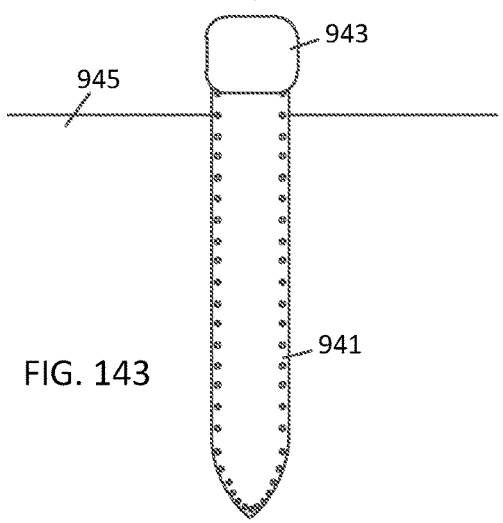
FIG. 143
FIG. 142
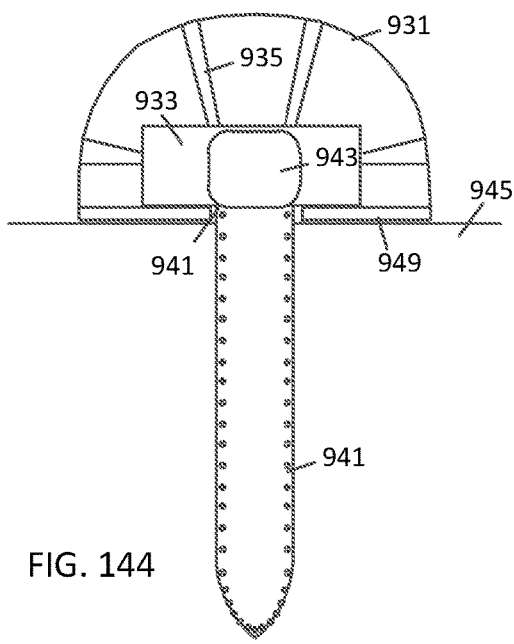
FIG. 144
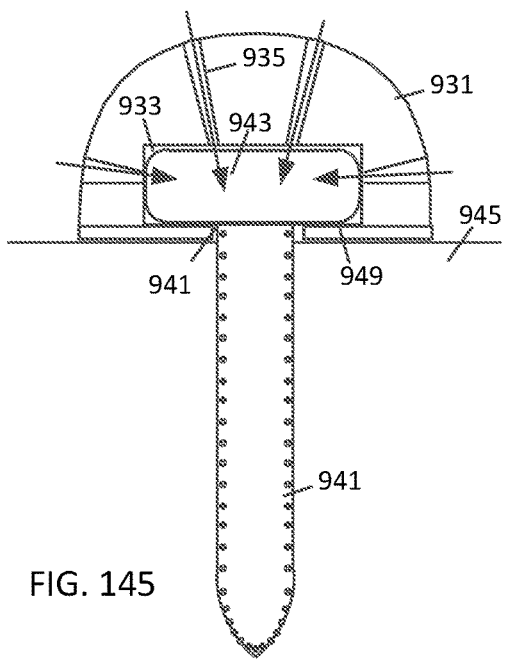
FIG. 145

BONE IMPLANT AUGMENT METHOD AND APPARATUS

CROSS REFERENCE TO RELATED APPLICATIONS

This patent application claims priority to U.S. Provisional Patent Application No. 62/328,799, "Bone Implant Augment Method And Apparatus" filed Apr. 28, 2016. This application is also a continuation in part of U.S. patent application Ser. No. 15/059,511, "Bone Implant Augment Method And Apparatus" filed Mar. 3, 2016, which claims priority to U.S. Provisional Patent Application No. 62/128,732, "PMMA Shims For Total Knee Arthroplasty" filed Mar. 5, 2015, U.S. Provisional Patent Application No. 62/133,072, "PMMA Shims For Total Knee Arthroplasty" filed Mar. 13, 2015, and U.S. Provisional Patent Application No. 62/237,018, "Shims Augment System" filed Oct. 5, 2015. U.S. patent application Ser. Nos. 15/059,511, 62/328,799, 62/237,018, 62/133,072, and 62/128,732 are hereby incorporated by reference in their entireties.

BACKGROUND

The proper functioning of a joint, such as the knee, hip, shoulder, ankle or elbow can be impeded by a variety of factors, including, disease, such as osteoarthritis, mechanical injury, bone deformation and a variety of other factors. Arthroplasty, or the surgical restoration of a joint, is a known procedure that is often used to relieve pain and improve joint function by replacing the diseased or damaged articulating surfaces of a joint with prosthetic components. Achieving stable joint balance is a primary goal for arthroplasty surgeons. A balanced joint is a joint that has the proper articulation and ligamentous balance in all orientations of the joint. The patient may be most comfortable when the artificial joint replicates the kinematics of the original, natural joint.

One of the most common arthroplasty procedures is knee replacement surgery. Some common forms of knee replacement surgery include total knee replacement ("TKR") surgery; partial knee replacement surgery, which is also known as unicompartmental arthroplasty ("UKA"); and revision knee surgery. Generally, in a TKR, the femur's bone from the lateral and medial condyles, or the articulating surfaces at the femur's distal end, are removed and replaced with a femoral prosthetic component. Additionally, in a TKR, the tibial plateau at the tibia's proximal end is also removed and replaced with a tibial prosthetic component.

The stability of a total knee arthroplasty is based upon the correct amount of bone resection from the femur and tibia of the knee and the balancing or release of soft tissues about the joint. Determining the correct amount of bone to resect can be challenging in the presence of preoperative bone loss or deformity. The surgeon frequently is forced to guess as to the correct amount of bone to resect. The surgeon performs releases of tissues to improve balance in the knee, especially if the patient has developed contractures prior to the procedure. The surgeon then performs trial range of motion and stressing of the knee with trial implants to determine knee stability. If the balance is not adequate the surgeon has several choices for improving balance. Depending on the type of imbalance, the surgeon can recut and remove bone from any surface, can perform soft tissue balancing or can add increased thickness to plastic tibial liner.

There are several situations in total knee arthroplasty that are not currently well addressed. When too much bone is removed from the distal femur as occurs with knees where bone collapse has occurred preoperatively, the surgeon has limited technical options for addressing the deficiency. Too much bone resection leads to the clinical problem of hyperextension of the knee or if the angle of the resection is incorrect leads to the clinical problem of instability of the knee. The desired solution is to correct the position of the femoral component by building up the implant from the bone surface. The correction may need to be longitudinal, i.e. moving the femur distally and symmetrically from the boney cuts or may be asymmetric, i.e. moving the angle of the femur relative to the boney resection surface, with or without longitudinal displacement of the implant.

A problem with bone implants is that they can weaken over time and in some cases fail. What is needed is a device for improving the bonding of bone implants to living bone that will enhance the shear, tensile and rotational strength of the bond.

SUMMARY OF THE INVENTION

The invention is a system for adjusting the length and angle of bone implants relative to the bone during surgeries. For example, a total knee replacement surgery involves cutting (resectioning) an end of the bone and then bonding a knee implant to the end of the bone and then reassembling the knee. The implant which can be a metal structure that is secured by mechanical bonding to the resection surface of the bone with a liquid (Polymethyl methacrylate) PMMA cement. The liquid PMMA cement is applied to the bone and implant in liquid form which structurally bonds the implant to the bone when the liquid PMMA hardens and cures.

A problem with existing systems is that if there is an error in the bone resectioning, there can be length and/or angular alignment errors of the knee implant. Without making corrections, the patient will not have a good surgical outcome. Incorrect length of cuts can produce excess joint laxity or increased tightness of the joint both associated with decreased pain and function. Any imbalance of a joint will lead to instability which is associated with pain, inflammation and impaired function. Alternatively, the angle of the knee can be wrong resulting in misalignment of the femur and tibia and/or angular instability of the joint. For example, when the implant is offset too far from the bone, the resulting arthroplasty can be too tight resulting in pain and not enough freedom of rotation. Conversely, if the implant offset is not offset enough the implant can be too loose resulting in joint instability. Laxity of just a few millimeters can result in pain and joint instability.

To solve this problem, the invention uses a hybrid bone inserts that include a pre-cured PMMA portion which is made at least partially of hardened PMMA and has good physical strength and a stem portion that is made of a material and has surface features that promote bone ingrowth and/or ongrowth. Suitable stem materials can include titanium and tantalum. The surface features of the stem can include pores, holes, grooves, recesses and/or protrusions which are about 40-800 microns in diameter, width and/or depth. The hybrid bone inserts can include various types of structures that are placed between the bone implant and the bone. The hybrid bone insert structures can include: tacks, shims, rods and any other suitable hybrid insert structures. The hybrid bone inserts can have a stem portion which is inserted into a hole formed in the resectioned surface of the bone and a portion that extends away from the surface of the bone to create an offset for the bone implant relative to the bone.

In an embodiment, a hybrid bone implant can be secured to a resectioned bone surface. The resectioned bone can be drilled and the stem section of the hybrid insert can be inserted into the drilled hole(s). This can be necessary when the hybrid bone insert is being placed into hard bone surfaces. In other embodiments, the hybrid inserts can be physically pressed into the surface of the bone without drilling the bone. The pressed insertion of the hybrid inserts can be useful when the exposed bony surface of the bone is soft. For example, the soft exposed bony surface of the bone: a metaphyseal bone, a cancellous bone, a trabecular bone, or a porous bone. By manually inserting the hybrid bone inserts, the surgeon can more easily control the positions and angles of the hybrid inserts.

Once the hybrid bone inserts are placed in the bone, the surgeon can then check the position of the hybrid implant against or adjacent to the insert(s) to determine the offset of the hybrid implant relative to the bone. A trial implant can be placed against PMMA portions of the hybrid inserts and a trial assessment can be performed which can include checking the range of motion and stability of the joint with the trial implant. The trial implants can provide all of the function needed for the trial assessment without having to use the final implant. In other embodiments, rather than using the trial implants, the alignment provided by the hybrid bone inserts can be checked with an alignment template to determine if the hybrid bone insert(s) will provide the proper implant length or angular offset.

The surgeon can check the functional correction of the joint with trial implants placed against the hybrid insert(s) to determine if proper correction is achieved or if a correction is deemed to not be adequate by the surgeon. If an error is made or if additional adjustments need to be made, the hybrid insert(s) can be removed and replaced with other hybrid bone insert(s) to adjust the implant offset relative to the bone so that the implant will be properly positioned relative to the bone and the revised bone implant offset can be trialed again. The trialing can be passed when the surgeon determines that the hybrid bone insert offset will provide a sufficient stability and range of motion. The trialing requirements can be predetermined. However, in some embodiments, the surgeon may need to determine a best fit hybrid insert which will provide the best surgical outcome for the patient based upon empirical trial and error rather than strict offset measurements. This hybrid bone insert replacement and trialing process can be repeated until the hybrid bone inserts that properly position the implant are found and the trial assessment is passed.

In an embodiment, once the correct offset is achieved as determined by the surgeon, the hybrid bone inserts can be left in place in or on the bone. The hybrid bone insert can have surface fenestrations and/or porosity which can allow ongrowth or ingrowth of the bone. Since the surface features of the stem provide bone interdigitation, liquid PMMA cement may not be applied to the interface between the stem and the bone to bond the hybrid bone inserts directly to the bone. The cured PMMA portions of the hybrid inserts can extend away from the bone and liquid PMMA can be applied to the exposed bone and the cured PMMA portions of the hybrid bone inserts.

The final bone implant can be unwrapped and placed on the liquid PMMA, hybrid inserts and bone. The liquid PMMA cement will then cure to chemically bond to the PMMA portions of the hybrid bone inserts and mechanically bond the implant to the bone. The cured PMMA cement and the PMMA portions of the hybrid bone inserts can form a solid substantially homogeneous high strength structure between the implant and exposed bone. While the stem of the hybrid insert can promote direct interdigitation with the bone through ingrowth and ongrowth without PMMA at the bone and stem contact interface. The hybrid bone insert offsets may only be applied to the bony surfaces and the final implant is not altered in any way, which improves the efficiency of the arthroplasty.

As discussed, various different types of hybrid bone inserts can be used to offset the implant such as: tacks, shims and/or rods. A hybrid tack insert can include a stem that does not include PMMA that is in direct physical contact with a cap that has cured PMMA. The stem of the hybrid tack is made of a material that has surface features that promotes bone ingrowth and/or ongrowth. The stem can be made of titanium or tantalum and the surface features of the stem can include 40-800 micron depth: recesses, grooves, or other surface features such as diameter, width and/or depth. In a tack embodiment, the stem is inserted into the bone and a bottom surface of the cap adjacent to the stem can contact the bone surface and the thickness of the cap can provide a predetermined offset. A trial implant can be placed in contact with the top surface of the cap opposite the stem and trialing of the hybrid insert offsets can be performed. Different tacks having different cap thicknesses can be available to change the implant offset from the bone and if adjustments are necessary the hybrid tack inserts can be replaced and trialed. The tacks can also have tapered or angled caps which are not uniform in thickness. For example, the upper and lower surface of the cap can include non-parallel planes and the intersection of the planes can define an acute angle. Once the hybrid tack inserts that provide the proper implant offset to pass the trialing are found the liquid PMMA cement can be used to create a chemical bond with the PMMA portions of the hybrid inserts and mechanically bond the final implant to the bone.

In different embodiments, the inventive system can be used for bone deficiency issues with PMMA cap portions of the hybrid bone inserts being used for augmentation of liquid PMMA cement. In an embodiment, stems of the hybrid bone insert structures can pre-penetrate bony surfaces. For example, stemmed augments can be inserted into holes formed in bones which can function like strengthening rebar in liquid PMMA cement. The technique that utilize the insert structures can include: 1) placing the non-PMMA bone ingrowth/ongrowth portions of hybrid bone inserts into bone and across bony surfaces, 2) applying cement to surface(s) of the bone and cured PMMA portions of the hybrid inserts, 3) applying the bone implant to the bone interface and liquid PMMA cement and cured PMMA portions of the hybrid bone insert, and 4) curing the PMMA cement to create a chemical bond with the PMMA portions of the hybrid bone inserts and a mechanical bond between the implant and the host bone. The entire assembly of bone, hybrid inserts, PMMA cement and the implant can be a composite structure.

In an embodiment, the hybrid inserts can be rods that have cured PMMA portions which are positioned outside the bone and bone ingrowth/ongrowth portions which do not include cured PMMA which can be inserted into a host bone. A cured PMMA portion of the hybrid rod inserts can extend away from the bony surfaces. Distal ends of the hybrid rod inserts may rest against the bottoms of the holes formed in the bone. The offsets of the hybrid rod inserts extending from the holes can be controlled by the lengths of the rods and the depths of the holes. The offset of the implant can be tested against the ends of the hybrid rod inserts with a trial implant and an assessment can be made of the hybrid rod inserts. If offset adjustments need to be made, the hybrid rod inserts can be replaced with different length hybrid rod inserts. In some embodiments, if the hybrid rod inserts need to be shortened, they can be replaced, cut or broken. In other embodiments, the hybrid rod inserts may not contact the implant. Once the proper hybrid rod inserts have been inserted into the bone, liquid PMMA cement can be applied to the bone, cured PMMA portions of the hybrid rod inserts and the implant. The liquid PMMA cement can cure to form a chemical bond with the PMMA portions of the hybrid rod inserts and a mechanical bond between the implant and the host bone.

In a hybrid shim insert embodiment, the insert structure can include a cured PMMA head having a larger cross section and a shape that can correspond to features of the implant and a stem section made of a material and with surface features that promote bone ingrowth and/or ongrowth. The surgeon can have a set of hybrid shim inserts which can have different thicknesses and the upper and lower surface of the heads of the hybrid shim inserts can be non-parallel planes and the intersection of the planes can define an acute angle. The hybrid shim inserts can include one or more stems which are inserted into the bone. The stems can be made of a material that has surface features and coatings which can promote bone ingrowth and ongrowth. The stems portions of the hybrid shim inserts may not have cured PMMA. The surgeon can perform a trial assessment with a trial implant to determine if the hybrid shim inserts will provide the proper implant offset. If there is an error in the offset of the implant relative to the bone, the hybrid shim inserts can be removed and replaced with hybrid shim inserts having different thicknesses and/or angles. Once a set of hybrid shim inserts passes the trial assessment, liquid PMMA can be applied to the bone, the exposed PMMA portions of the hybrid inserts and implant. The liquid PMMA cement can cure and chemically bond with the PMMA portions of the hybrid shim inserts and form a strong mechanical bond between the implant and the host bone.

Although the cured PMMA portions of the hybrid shim insert are described as being made of PMMA, in some embodiments, the hybrid inserts can include other materials. For example, the hybrid inserts may include metal or polymer substrates. For example, a metal rod such as stainless steel or titanium can be encapsulated within the cured PMMA in the cured PMMA area. In other embodiments, the inserts can include polymer structures with the PMMA portions encapsulated with cured PMMA. This composite design can be useful when higher structural strength is needed for the hybrid insert which can increase the mechanical properties such as shear and compression strength.

The inventive system can be particularly useful in surgeries that require a very high implant position accuracy such as Total Knee Arthroplasty (TKA). In an embodiment, a TKA may require resectioning the distal end of the femur. If there are any errors in the resection surfaces the femoral implant will not be positioned correctly relative to the femur. The error may cause the patient to have difficulty walking because the length and/or angle of the reconstructed limb may be incorrect. Incorrect balancing of the knee is associated with increased pain and inflammation and decreased function. In an embodiment, the TKR may include a first resection surface on a medial condyle of the femur (MFC) and the second resection surface on a lateral femoral condyle of the femur (LFC). If there are errors in the MFC and/or LFC resection surfaces, hybrid shim inserts placed on these surfaces can be used to correct the position of the implant relative to the bone. More specifically, medial and lateral hybrid shim inserts having the same offsets can be used if the errors are only in length or distal offset and there are no angular errors. In contrast, medial and lateral hybrid shim inserts having different offsets can be used if there are angular and length offset errors or a single hybrid shim insert can be used to make angular correction. This invention describes an efficient technique for using corrective hybrid shim inserts that are stable for trial reductions and stress testing and require no additional manipulation is required once the trial reduction determines that the positioning of an implant bonded to the inserts is correct.

In different embodiments, hybrid tack inserts can be used with a distal femoral application. For example, in different scenarios the inventive system can be used for femoral over-resections where there is a flexion/extension mismatch. The inventive system can provide corrective options. The inventive system can be used to lower a joint line which can quickly and accurately make alignment adjustments so that any alignment imbalance can be corrected. In some embodiments, the inventive system can be used with hybrid tack inserts placed in multiple surfaces of the bone such as the anterior, posterior and/or distal surface(s) when the position of the implant needs to be adjusted.

In an embodiment, the hybrid bone inserts can be used to make angular corrections such as angular augments and asymmetric augments. In the illustration, the head of the hybrid shim insert structure between the bone and the implant can be angled. The thickness of the hybrid shim insert can be thicker at one side surface than the opposite side. This can allow the angle between the implant and the bone to be adjusted. This angular correction can be used for various angular scenarios including: restoring the correct angulation if there is over-resection. The hybrid insert can be applied to bony surfaces and the different thicknesses to create different angular corrections. These angular corrections can be applied to single or multiple surfaces of the bone.

BRIEF DESCRIPTION OF THE DRAWINGS

FIG. 12 illustrates an anterior view of a femur with a distal resection surface with PMMA tack inserts and a trial implant.

FIG. 13 illustrates an anterior view of a femur with a distal resection surface with PMMA tack inserts bonded to a final implant.

FIG. 14 illustrates an anterior view of a femur with a distal resection surface with PMMA tack inserts and a trial implant.

FIG. 15 illustrates an anterior view of a femur with a distal resection surface with PMMA tack inserts bonded to a final implant.

FIG. 27-35 illustrate side views of different embodiments of PMMA tack inserts.

FIG. 36 illustrates a top view of an embodiment of a PMMA tack insert.

FIG. 37 illustrates a side view of an embodiment of a PMMA tack insert in a bone.

FIGS. 38-40 illustrate side views of different embodiments of PMMA tack inserts with bone retention mechanisms.

FIG. 41 illustrates a top view of an embodiment of a PMMA tack insert.

FIG. 75 illustrates a modular PMMA tack with separated PMMA cap attachments.

FIG. 76 illustrates a modular PMMA tack coupled to PMMA cap attachments.

FIG. 77 illustrates a modular PMMA tack coupled to PMMA cap attachments in a bone hole.

FIG. 78 illustrates a top view of a tool used with the PMMA cap attachments.

FIG. 79 illustrates a side view of an embodiment of a threaded PMMA insert.

FIGS. 80-81 illustrate side views of an embodiment of a threaded PMMA insert positioned at different offsets in a bone.

FIG. 141 illustrates a side view of an embodiment of a PMMA cap.

FIG. 142 illustrates a bottom view of an embodiment of a PMMA cap.

FIG. 143 illustrates a side view of an embodiment of a PMMA cap over a stem inserted into a bone.

FIG. 144 illustrates a side view of an embodiment of a PMMA cap on a stem inserted into a bone.

FIG. 145 illustrates a side view of an embodiment of a PMMA cap in a locked position on a stem inserted into a bone.

DETAILED DESCRIPTION

The present invention is directed towards bone implant augment methods and apparatus for surgical procedures such as Total Knee Arthroplasty (TKA). The present invention can allow surgeons to meet increased technical demands and expectations of both speed and accuracy. The inventive systems can provide more accurate adjustments to implant positions to supplement existing instrumentation and smaller increment implant sizing which can improve the accuracy limitations of mechanical systems due to imperfect mechanical resection bone cuts in both axial length and angular orientation.

The present invention can provide a system and method for adjusting the bone implant components for these imperfect mechanical bone cuts. The inventive devices for correction of imperfect resection cuts are accurate and quickly installed during surgery so that the offset and position of the implant relative to the bone is corrected. The inventive system and apparatus can minimize surgical delays and can be provided in a simple surgical kit. The kit components can include bone inserts that have cured PMMA portions and stems which have bone ingrowth or ongrowth surfaces. The kit components which can integrate with existing techniques/methods and tools. In situations with hardened or sclerotic bone, the final bone implant construct of inserts with stems placed within the bone and precured PMMA portions which are chemically bonded to the cured liquid cement. This hybrid bone insert construction has stronger mechanical properties at the bone to stem interface through ingrowth and at the liquid PMMA cement interface to the cured PMMA portion of the bone insert than an implant mechanically bonded to a bone with just PMMA cement. In some embodiments, the hybrid bone inserts can have high strength substrates with the cured PMMA portions encapsulated in cured PMMA which can improve the bonding strength of the implant connection to the bone.

Figure 1:
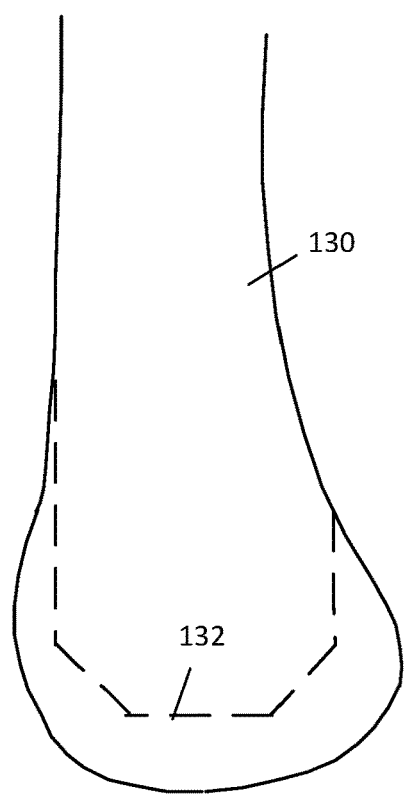
FIG. 1 illustrates a side view of a bone.
Figure 2:
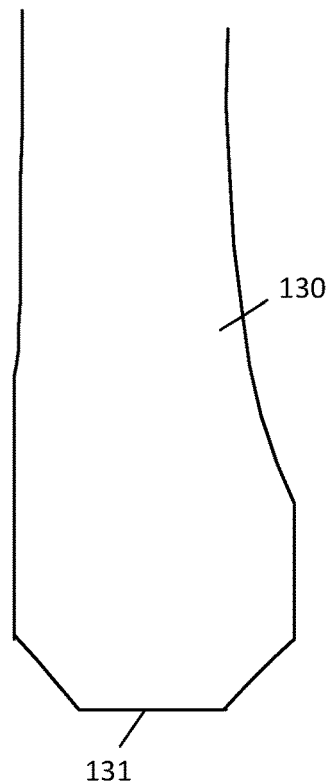
FIG. 2 illustrates a side view of a bone with resectioned surfaces.
Figure 3:
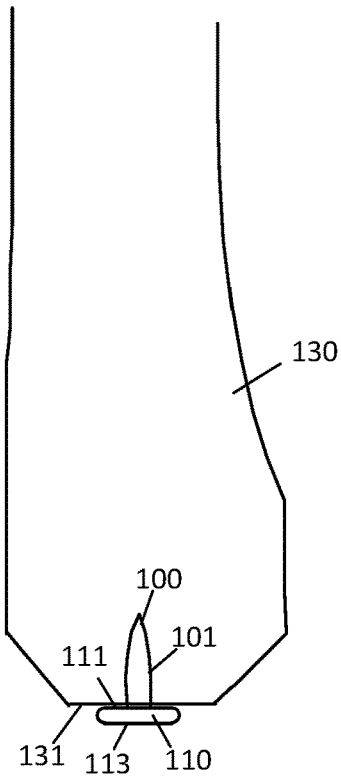
FIG. 3 illustrates a side view of a bone with an embodiment of a PMMA tack insert in a distal resection surface.
Figure 4:
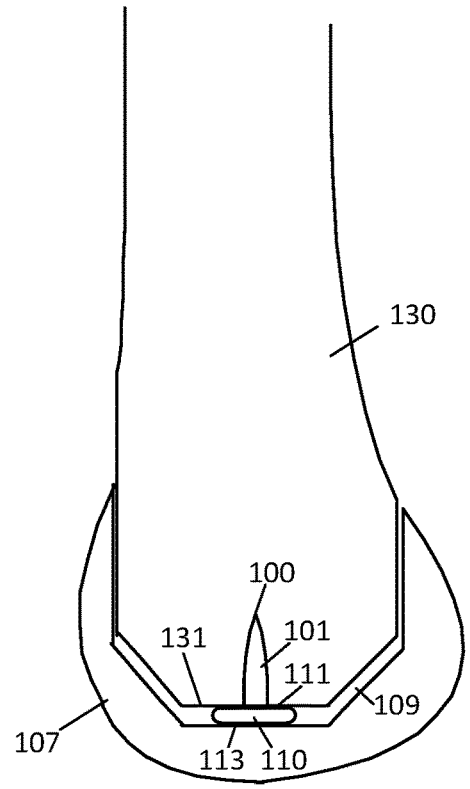
FIG. 4 illustrates a side view of an implant bonded to a bone and a tack on a PMMA distal resection surface.

FIGS. 1-4 illustrates side views of a femur bone 130 to which a bone implant 107 will be bonded to. With reference to FIG. 1, a bone 130 is illustrated with markings 132 indicating locations of resection cuts. With reference to FIG. 2, the bone 130 has been cut and includes resection surfaces 131. With reference to FIG. 3, a bone insert 100 has been placed in the resection surface 131. In this embodiment, the hybrid bone insert 100 includes a cap 110 having cured PMMA surfaces and a stem 101 made of a material with surface features which promote bone ingrowth and/or ongrowth which does not have PMMA. The hybrid bone insert 100 has been fully inserted into the bone 130 so that a first surface 111 of the cap 110 is adjacent to and in direct physical contact with the resection surface 131. With reference to FIG. 4, the implant 107 is placed on the bone 130 with a surface of the implant 107 in direct physical contact with a second surface 113 of the cap 110 which is opposite the first surface 111.

Liquid PMMA cement 109 can be applied to the exposed bone 130, exposed hybrid bone insert 100 and the implant 107. In an embodiment, the liquid PMMA cement 109 can be pressurized and injected into the space between the implant 107 and the bone 130. The liquid PMMA cement 109 can cure and chemically bond to the PMMA portion cap 110 of the hybrid bone insert 100 and create a strong mechanical bond between the implant 107 and the bone 130. In an embodiment, the cap 110 surfaces of the bone implant 107 can be coated with materials that can chemically bond to the liquid PMMA cement 109. For example, the cap 110 surfaces of the implant can be coated with cured PMMA. In other embodiments, the cap 110 surfaces of the implant 107 can be textured or have physical features such as grooves, holes, fenestrations, etc. which can improve the interdigitation of the liquid PMMA cement with the implant 107.

Figure 5:
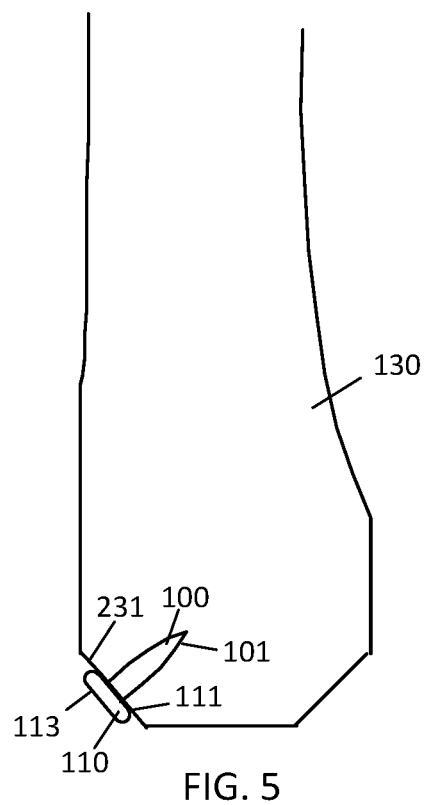
FIG. 5 illustrates a side of view of a bone with an embodiment of a PMMA tack insert in an anterior resection surface.
Figure 6:
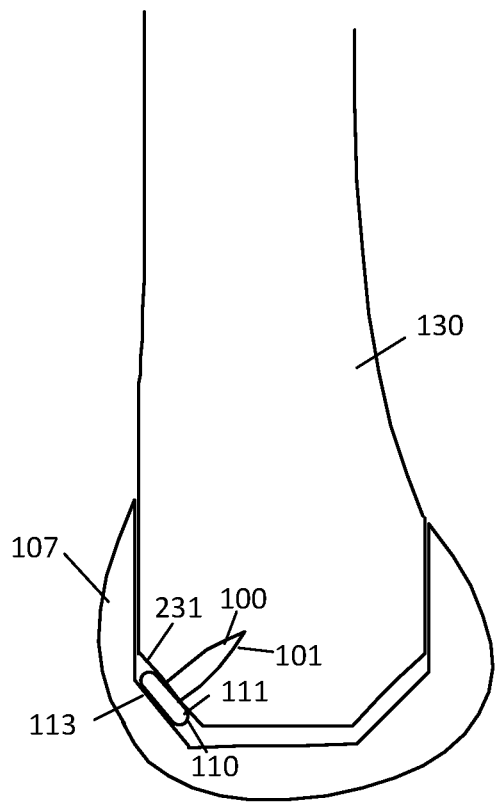
FIG. 6 illustrates a side view of an implant bonded to a bone and a PMMA tack insert on an anterior resection surface.

In other embodiments, the hybrid bone insert 100 can be inserted into a different resection surface such as an anterior resection surface With reference to FIG. 5, a hybrid bone insert 100 has been placed in the anterior resection surface 231. In this embodiment, the hybrid bone insert 100 includes a cap 110 which can have PMMA surfaces and a stem 101 made of a material with surface features which promote bone ingrowth and/or ongrowth which does not have PMMA. The hybrid bone insert 100 has been fully inserted into the bone 130 so that a first surface 111 of the cap 110 is adjacent to and in direct physical contact with the anterior chamfer resection surface 231. With reference to FIG. 6, the implant 107 is placed on the bone 130 with a surface of the implant 107 in direct physical contact with a second surface 113 of the cap 110 which is opposite the first surface 111. In other embodiments, the hybrid bone insert 100 can be placed on any surface of the bone 130 between the bone 130 and the implant 107.

The insertion of the hybrid bone insert 100 into the bone 130 can comprise various procedural steps. In an embodiment, the bone resection surface can be drilled and the stem of the hybrid bone insert 100 can be placed into the hole formed. The drill can be a stepped drill bit which creates an insert hole having a specific depth and diameter. In other embodiments, the hybrid bone insert 100 can be physically pressed into the bone 130. The force of the stem 101 against the bone 130 can create the hole in the bone. The surgeon can then trial the offset of the hybrid bone insert 100 to determine the proper offset of the hybrid bone insert 100. If the insert needs to be replaced, the insert 100 can be removed and a replacement hybrid bone insert 100 can be pressed into the same hole formed by the previously trialed hybrid bone insert 100. The hybrid bone inserts 100 can have caps 110 that have cured PMMA surfaces and structural features that can allow the surgeon to easily remove the bone inserts 100. In the illustrated example, the caps 110 can have a rounded outer surface facing the bone 130 that allows the surgeon to grasp and pull up on the cap 110. In other embodiments, a tool can be used to grasp and/or pull the cap 110 away from the bone 130.

The inventive process solves a significant problem that occurs when too much bone is removed during resectioning. There are no known methods for easily adding bone material to the cut bone surfaces and readjusting the bone to compensate for over cuts can be impossible. The application of the described hybrid bone inserts solves this problem by allowing surgeons to increase the implant offset and has the added benefit of providing a stronger bond between the bone and implant because the implants can be secured to stems mechanically bonded in holes in the bone. In contrast, a normal bone implant may only rely upon PMMA cement placed on the outer surfaces of the bone to provide the mechanical bonding to the implant.

Figure 7:
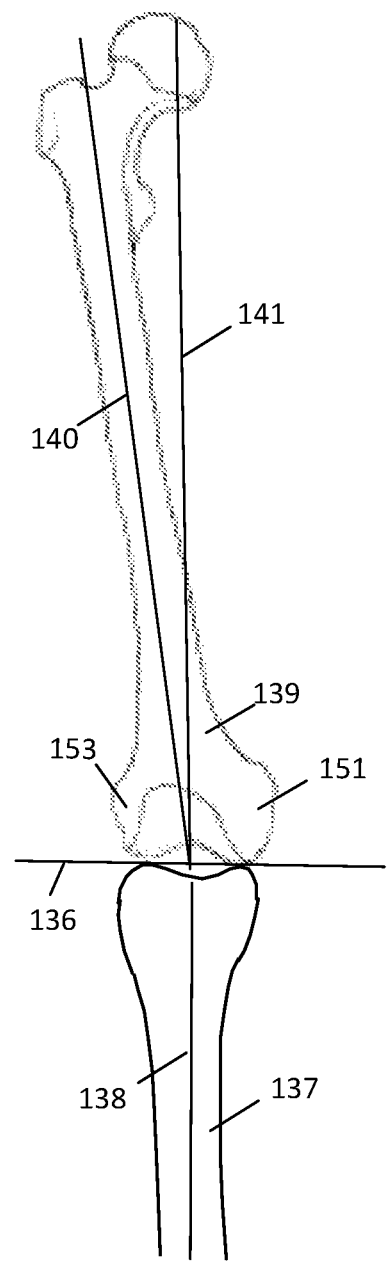
FIG. 7 illustrates an anterior view of a femur and tibia.

The alignment of the implant can be based upon the anatomical axis of the patient rather than a mechanical axis. With reference to FIG. 7, an anterior view of the knee joint is illustrated. The distal surfaces of the femur 137 can be a horizontal axis that is parallel to the rotational axis of the knee 136. Each patient's anatomical geometry can be different and the femur 139 can have various alignment configurations with the tibia 138. In the illustrated example, the geometric axis 141 of the tibia 138 can be defined by a line between the head at the proximal end of the femur 139 and the center of the knee. The geometric axis 141 can be perpendicular to the rotational axis of the knee 136 and aligned with the center axis of the tibia 138. As illustrated, the anatomic center axis 140 of the femur 139 is angled from the geometric center axis 141 of the tibia 138 and is not be perpendicular to the rotational axis of the knee 136 in the illustrated example. However, in other embodiments (not illustrated) the surgeon may configure the patient's leg with the anatomical axis 140 of the femur 139 in a perpendicular orientation relative to the rotational axis 136 of the knee and aligned with the center axis 138 of the tibia 137.

Figure 8:
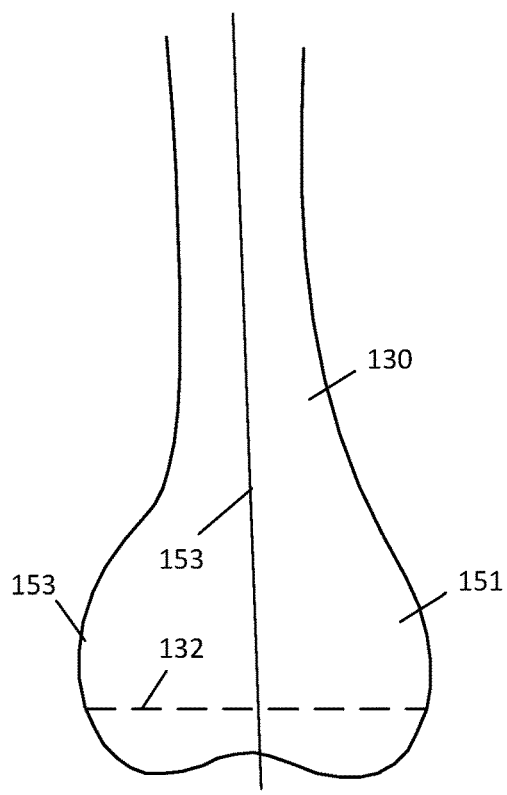
FIG. 8 illustrates an anterior view of a distal portion of a femur.
Figure 9:
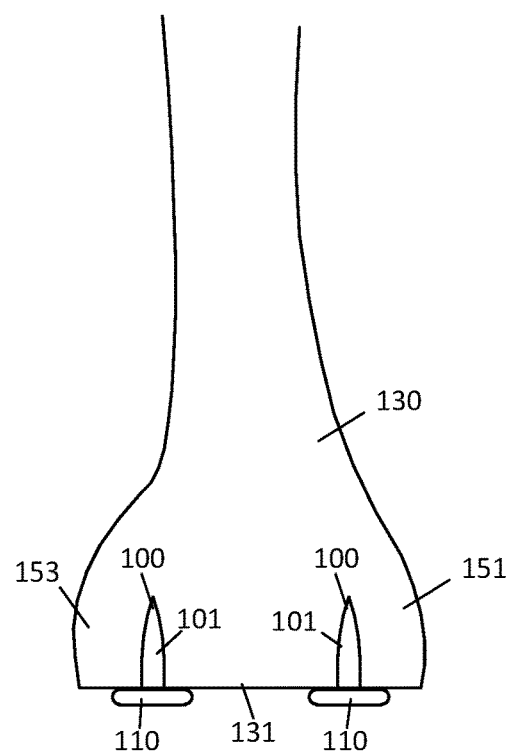
FIG. 9 illustrates an anterior view of a femur with a distal resection surface with PMMA tack inserts.

FIGS. 8-11 illustrate anterior view of a femur bone 130 and bone implant 107. With reference to FIG. 8, the bone 130 is illustrated with a lateral condyle of the femur (LFC) 153 and a medial condyle of the femur (MFC) 151. The resection cut markings 132 extends through portions of both the lateral condyle 153 and the medial condyle 151. The resection cut markings 132 may not be perpendicular to the center axis of the femur 153. FIG. 9 illustrates the bone 130 after being cut with a resection surface 131 and with hybrid bone inserts 100 placed in the resection surface 131 on the LFC 153 and MFC 151. The hybrid bone inserts 100 have been fully inserted into the bone 130 so that a first surface 111 of the caps 110 are in direct physical contact with the resection surface 131 of the bone 130. The implant 107 is placed on the bone 130 and in direct physical contact with the second surfaces 113 of the caps 110.

Figure 10:
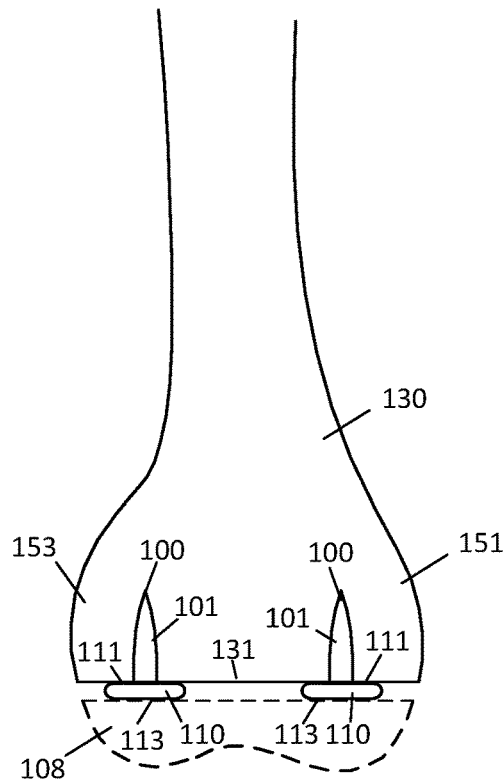
FIG. 10 illustrates an anterior view of a femur with a distal resection surface with PMMA tack inserts with a trial implant.
Figure 11:
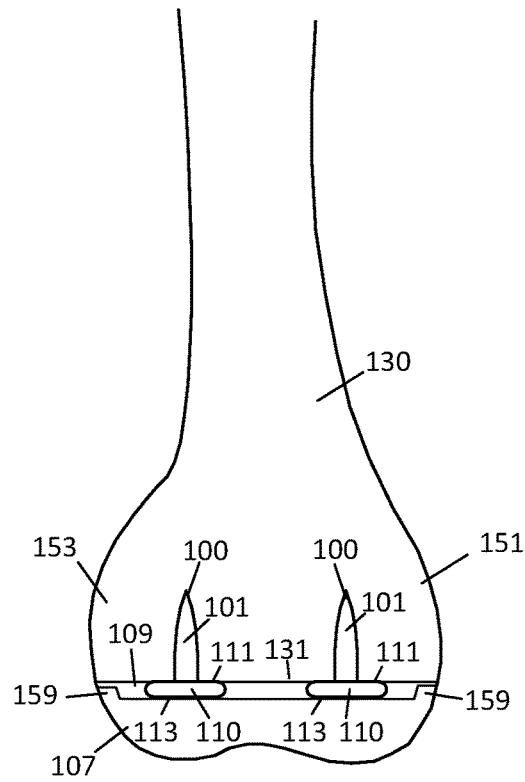
FIG. 11 illustrates an anterior view of a femur with a distal resection surface with PMMA tack inserts bonded to a final implant.

With reference to FIG. 10, the surgeon can check the offset of the implant 107 relative to the bone 130 and determine if the offset is correct. Checking the offset can include length and angular offset measurements of the implant 107 relative to the bone 130. Checking can also be performed for functional performance with use of trial implants and range of motion of the joint with assessment of stability and motion. If changes need to be made, the hybrid bone inserts 100 can be removed and replaced with another insert that has a cap 110 having a different thickness or a different angle between the first surfaces 111 and the second surfaces 113. The position of the implant can be checked with a trial implant 108 and various mechanical tests can be performed to determine if the implant will be properly positioned by the hybrid bone inserts 100. With reference to FIG. 11, once the proper inserts are found to properly position the implant, liquid PMMA 109 can be applied to the hybrid bone inserts 100, resection surface 131 of the bone 130 and the implant 107. The liquid PMMA can cure to bond the implant 107 to the bone 130 and hybrid bone inserts 100. In the illustrated embodiment, the implant 107 can include a raised edge 159 which can extend around the outer perimeter of the implant 107. The raised edge 159 can function to help retain the liquid PMMA cement 109 within the space between the bone 130 and the implant 107. The height of the raised edge 159 can be less than the thickness of the hybrid bone inserts 100 so that the implant 107 will contact the hybrid bone inserts 100 but the raised edge 159 will not contact the bone 130.

Figure 101:
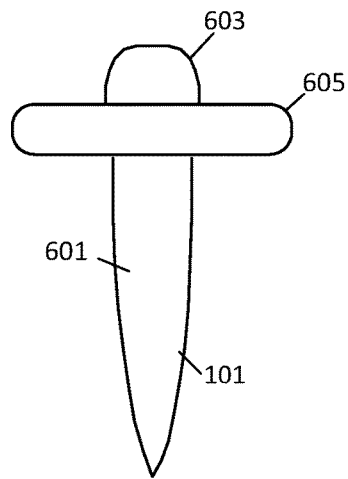
FIG. 101 illustrates a side view of a tack insert having two layer cap.
Figure 102:
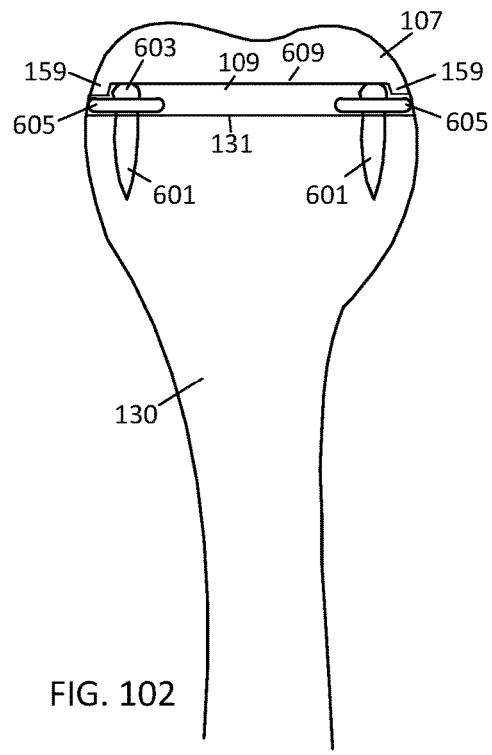
FIG. 102 illustrates a view of a bone with a resection surface with PMMA tack inserts bonded to a final implant.

In some embodiments, the raised edge of the implant can engage features of the tack inserts. For example, with reference to FIG. 101 an embodiment of a hybrid bone tack insert 601 is illustrated which has a stem 101 without PMMA and a stepped cap with a lower cap 605 and an upper cap 603 which have cured PMMA surface. In the illustrated embodiment, the lower cap 605 can have a smaller outer diameter than the upper cap 603. In other embodiments, the lower cap 605 can have an exposed surface that is not covered by the upper cap 603. With reference to FIG. 102, as discussed above with reference to FIG. 11, the implant 107 can have a raised edge 159 which can be on an edge of the implant 107 bonding surface 609. In an embodiment, the stems 101 of the hybrid bone tack inserts 601 can be pressed into a resection surface 131 of the bone 130. The hybrid bone tack inserts 601 can be trialed with a trial implant. If the hybrid bone tack inserts 601 provide the proper implant 107 offset, liquid PMMA cement 109 can be applied to the bonding surface 609, the internal raised edge 159 surfaces, the PMMA portion of the hybrid bone tack inserts 601 and the resection surface 131 of the bone 130. The implant 107 can be placed on the hybrid bone tack inserts 601 with the raised edges 159 adjacent to the lower caps 605 and the bonding surface 609 adjacent to the upper caps 603. In an embodiment, the offset of the upper cap 603 from the lower cap 605 can be the same or similar to the height of the raised edge 159 from the bonding surface 609. Be raised edge 159 can also be place in close proximity to the outer side surfaces of the upper caps 603. Thus, the raised caps 603 can function as indexes to help place the implant 107 in the proper aligned position on the resection surface 131 of the bone 130.

FIGS. 12-15 illustrate adjusting the cap thicknesses of the inserts to properly offset the implant. With reference to FIG. 12, the proper predetermined length offset of the implant 107 relative to the bone 130 can be represented by line 181. However, in the illustrated embodiment, the measured, calculated or trialed with a trial implant 108 to determine that the offset line 183 is substantially shorter than the proper offset line 181. The offset line 183 can be determined during a trial process of the inserts 100 where a trial implant is placed on the hybrid inserts 100 and the stability and range of motion can be tested. If these trial tests fail, the surgeon can make corrective adjustments to the hybrid inserts 100 to alter the offset so the final implant will match the offset line 183. With reference to FIG. 13, the length of the offset between the bone 130 and the implant 107 has been altered by replacing the hybrid inserts 100 with replacement hybrid inserts 185 having thicker caps 186. With the replacement inserts 185, the offset of the final implant 107 matches the proper predetermined length offset line 181. If the offset position of the implant needs to be shortened, the hybrid inserts 100 can be replaced with hybrid inserts 100 having thinner caps. In this embodiment, the angle of the resection surface 131 was correct, so the thicker caps 186 of the hybrid inserts 185 can have the same thickness so that the angle of the implant 107 is not changed relative to the bone 130. Liquid PMMA 109 can be applied to the exposed areas of the bone 130, PMMA portions of the replacement hybrid inserts 185 and the final implant 107. The liquid PMMA 109 can cure to chemically bond to the PMMA portions of the bone inserts 183 and mechanically bond the implant 107 to the bone 130.

With reference to FIG. 14, an embodiment is illustrated where the hybrid inserts 100 and the measured, calculated or determined offset line 183 is at a different angle than the proper offset line 181 during trialing. The offset angle of the trial implant 108 relative to the bone 130 can be changed and corrected by using hybrid inserts 100 having different thickness caps 110. With reference to FIG. 15, the original hybrid inserts 100 have been removed and replaced with a first insert 187 which has a thick cap 188 in the LFC and a second insert 189 which has a thicker cap 190 in the MFC. These replacement inserts 187, 189 can cause the final implant 107 offset to be properly angled and positioned and match the correct predetermined offset line 181. FIGS. 14 and 15 illustrate one embodiment of an angular correction. However, if the surgeon needs to angle the implant 107 more towards the medial side, the hybrid insert 100 placed in the MFC 151 can have a thinner cap 110 than the cap 110 on the hybrid insert 100 placed in the LFC 153.

With reference to FIGS. 13 and 15, once the surgeon determines that the hybrid inserts 100 will provide the proper offset of the implant 107 relative to the bone 130 by a trial process, a liquid PMMA cement 109 can be applied to the exposed PMMA surfaces of the hybrid inserts 100 outside the bone 130, the exposed resection surface 131 of the bone 130 and the bonding surfaces of the implant 107. The liquid PMMA cement 109 may also injected or placed in the spaces between the bone 130 and the implant 107 around the cap 110. The liquid PMMA cement 109 cannot be placed in contact areas between the bone 130 and the hybrid inserts 100. The liquid PMMA cement will harden into a solid and chemically bond to the cured PMMA cap 188, 190 portions of the insert 100 and mechanically bond the bone 130 to the implant 107. The stems 101 can have bone ingrowth and ongrowth surfaces which provide interdigitation surfaces with the bone. Once cured and fully hardened and bone has grown into the stems 101 of the hybrid inserts 100, the implant 107 will be rigidly attached to the bone 130.

Figure 16:
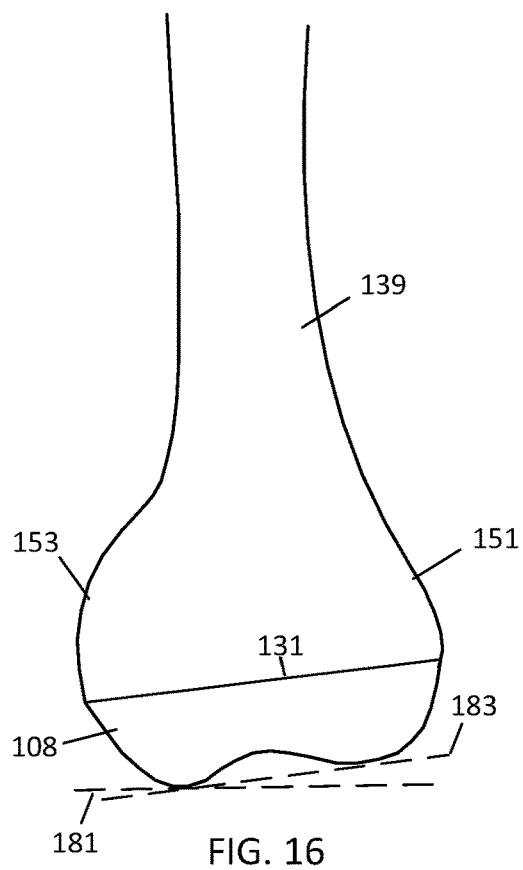
FIG. 16 illustrates an anterior view of a femur with a distal resection surface with a trial implant.
Figure 17:
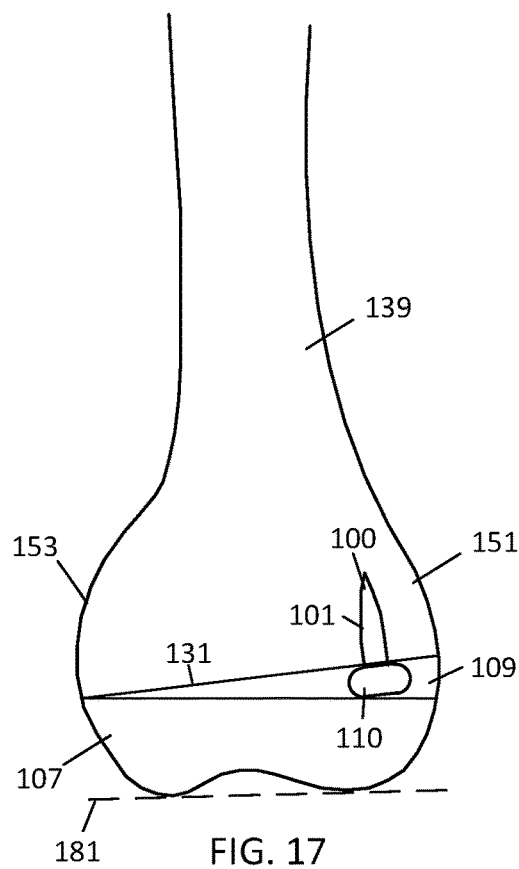
FIG. 17 illustrates an anterior view of a femur with a distal resection surface with a PMMA tack insert bonded to a final implant.
Figure 18:
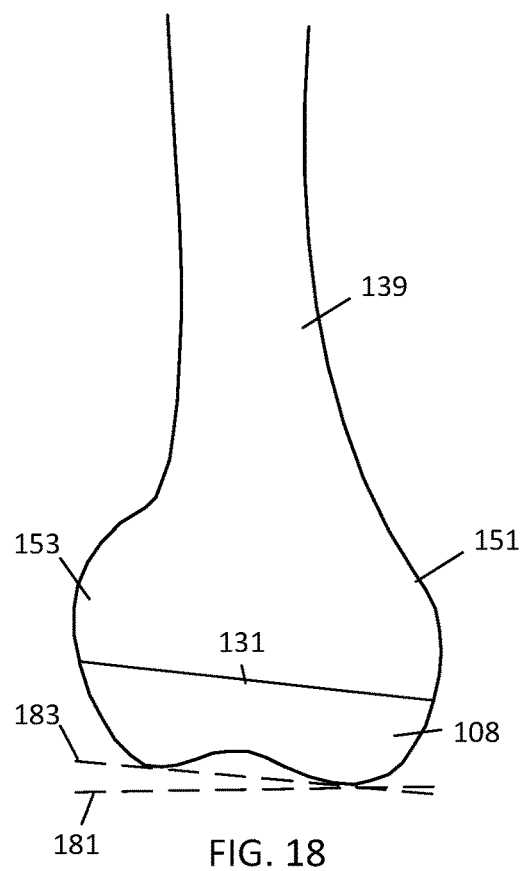
FIG. 18 illustrates an anterior view of a femur with a distal resection surface with a trial implant.
Figure 19:
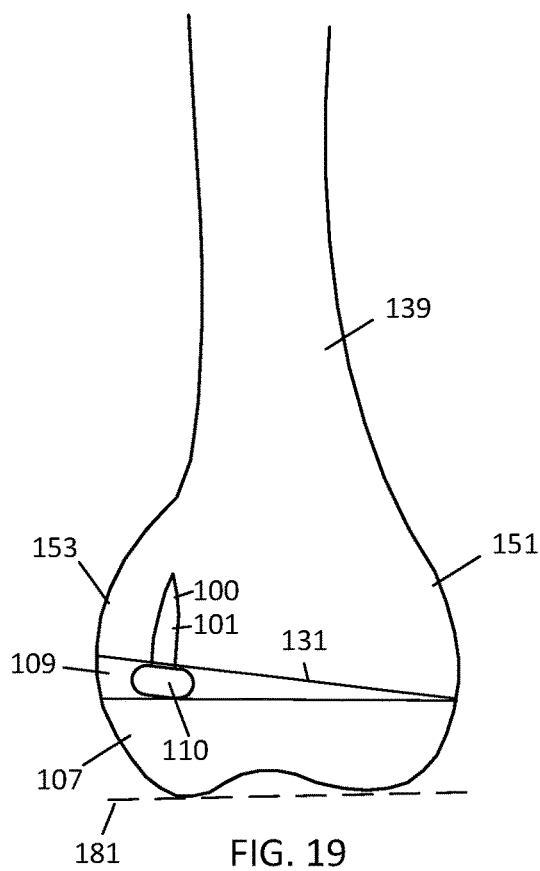
FIG. 19 illustrates an anterior view of a femur with a distal resection surface with a PMMA tack insert bonded to a final implant.

FIGS. 11-15 illustrate embodiments where two hybrid inserts are used to make corrections to the implant offset relative to the femur. However, in other embodiments is can be possible to make angular corrections to the offset of the implant with a single implant. FIG. 16 illustrates a femur 139 with a resection surface 131. A trial implant 108 can be placed on the resection surface 131 and the surgeon can perform a trial process and determine that the measured offset line 183 does not match the correct offset line 181 and material needs to be added to the MFC 151 side of the resection surface 131. With reference to FIG. 17, a stem 101 of the hybrid tack insert 100 is inserted into the MFC 151 side of the resection surface 131 and the trial process can be repeated. If the trial process is passed, liquid PMMA 109 can be applied to the resection surface 131, hybrid tack insert 100 and the implant 107 to mechanically bond the implant 107 to the femur 139. With reference to FIG. 18, a trial implant 108 is attached to the resection surface 131 and the trial process can determine that material needs to be added to the LFC 153 side of the resection surface. With reference to FIG. 19, a hybrid tack insert 100 is inserted into the LFC 153 side of the resection surface 131 to correct the offset of the implant 107. When the trial testing has been passed, liquid PMMA 109 can be applied to the resection surface 131, the exposed PMMA portions of the hybrid tack insert 100 and the implant 107 to mechanically bond the implant 107 to the femur 139.

Figure 20:
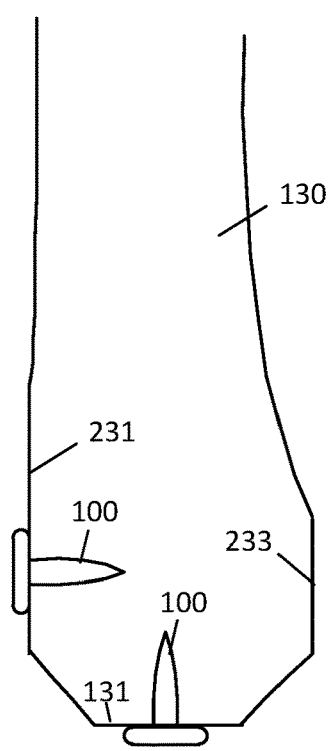
FIG. 20 illustrates a side view of a bone with PMMA tack inserts in anterior and distal resection surfaces.
Figure 21:
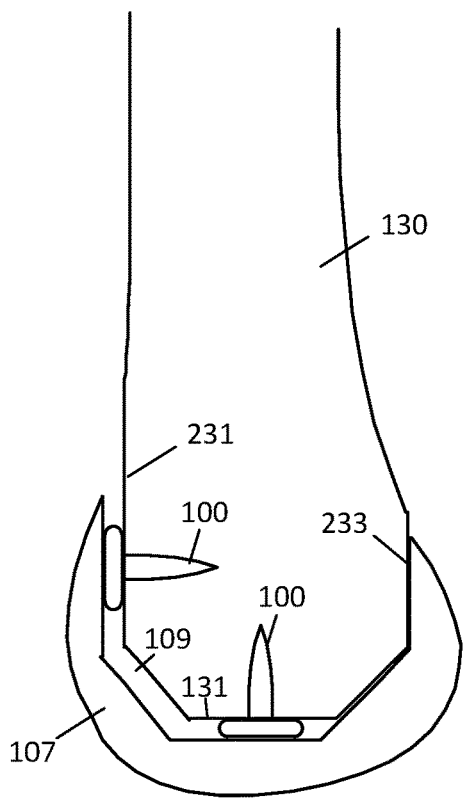
FIG. 21 illustrates a side view of a bone with PMMA tack inserts in anterior and distal resection surfaces bonded to a final insert.
Figure 22:
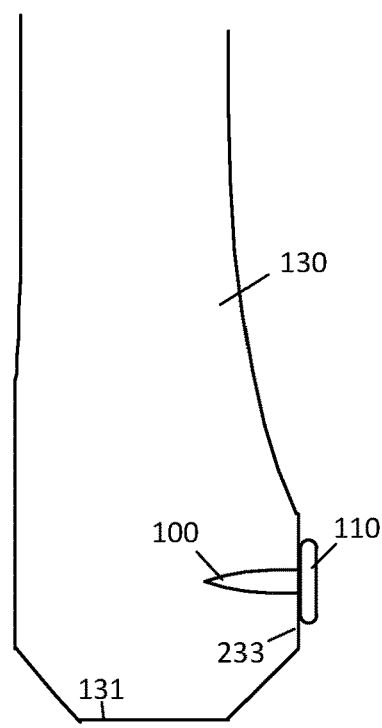
FIG. 22 illustrates a side view of a bone with a PMMA tack insert in a posterior resection surface.
Figure 23:
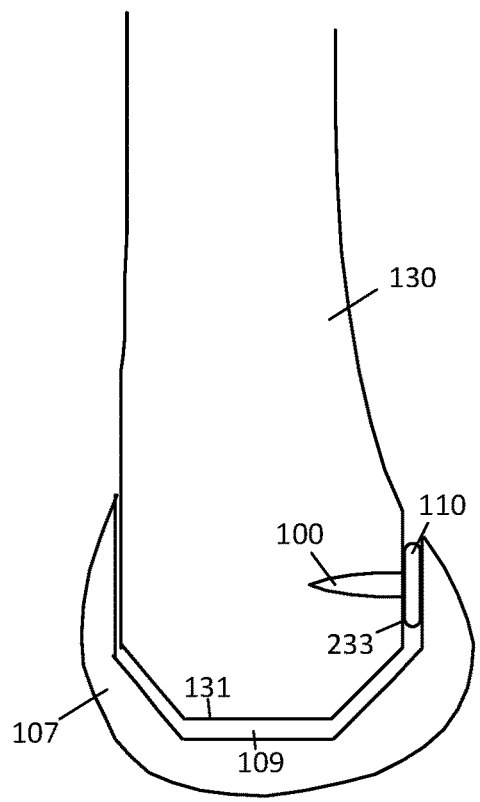
FIG. 23 illustrates a side view of a bone with a PMMA tack insert in a posterior resection surface bonded to a final insert.

With reference to FIGS. 20-23, side views of a bone 130 having multiple resection surfaces 131 are illustrated. In some embodiments, the hybrid tack inserts 100 can be placed on multiple resection surfaces 131 which are not in the same plane. The hybrid tack inserts 100 can allow the surgeon to move the implant 107 towards the anterior or posterior sides of the bone 130. With reference to FIG. 20, one or more hybrid tack inserts 100 are placed in an anterior resection surface 231 and a distal surface 131 that can be perpendicular to a center axis of the bone 130 With reference to FIG. 21, the implant 107 position relative to the bone 130 can be adjusted towards the anterior surface by placing hybrid tack inserts 100 in an anterior resection surface 231. With reference to FIG. 22, one or more hybrid tack inserts 100 are placed in a posterior resection surface 233 that can be substantially parallel to a center axis of the bone 130. With reference to FIG. 23, the implant 107 is moved towards the posterior surface relative to the bone 130 by using hybrid inserts 100 that have different offsets in the posterior surfaces 233. By having hybrid inserts 100 in multiple resection surfaces the surgeon can have more precise control of the position of the implant 107 relative to the bone 130 to match the predetermined required offset distances, relative positions and angles in three dimensional space. Placement of hybrid inserts 100 in the posterior resection surface 233 will allow the surgeon to securely increase the size of a femoral component to reduce a selective flexion gap imbalance.

The present invention illustrates how an implant can be offset relative to a bone in different directions in three-dimensional space. In an embodiment, the bone can be aligned with an X, Y, and Z coordinate system with the center axis of the bone aligned with the Z-axis. The anterior surface can face the X-axis and the joint at the distal end of the bone can rotate about the Y-axis. With reference to an X, Y, Z coordinate system, FIGS. 9-13 illustrate how bone inserts can be used to offset the implant from the bone in the Z direction and FIGS. 20-23 can illustrate how hybrid bone inserts 100 can be used to offset the implant from the bone in the X direction. In these illustrations the implant 107 can have a "U" shape so that the surgeon can move the implant manually in the Y direction. The hybrid bone inserts 100 can used to control the rotation of the implant 107 relative to the bone 130 about the X axis, Y axis and Z axis. More specifically, FIGS. 16-19 illustrate how the hybrid bone inserts 100 are used to adjust the rotation of the implant about the X-axis. Similarly, the hybrid bone inserts 100 illustrated in FIGS. 20-23 can be used to control the rotation of the implant 107 about the Y-axis. FIGS. 110-113 illustrate how the hybrid bone inserts 100 can be used to control the offset rotation of the implant about the Z-axis.

Figure 97:
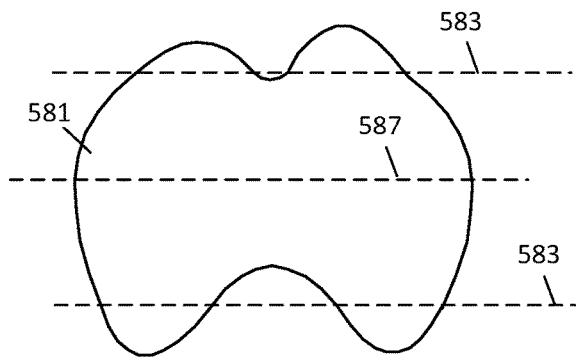
FIG. 97 illustrates a bottom view of a distal end of a bone.
Figure 98:
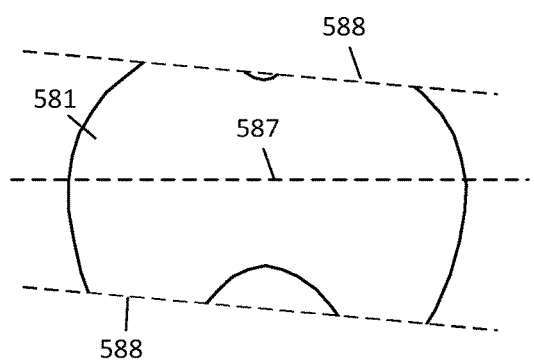
FIGS. 98-99 illustrate bottom views of a distal end of a bone after resectioning.
Figure 99:
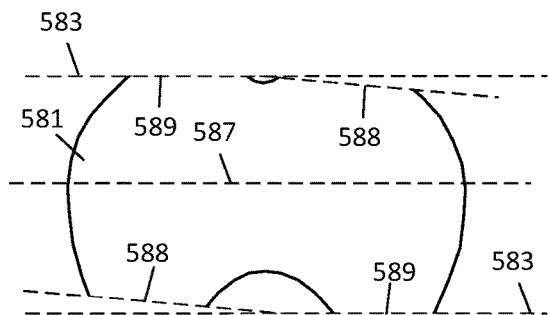
Figure 100:
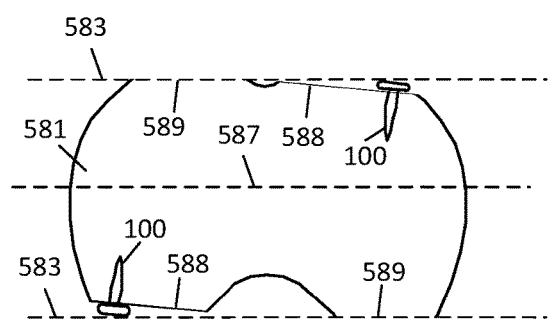
FIG. 100 illustrates a bottom view of a distal end of a bone with tack inserts.

FIG. 97 illustrates a bottom view of an embodiment of a bone 581 that can be marked with resection lines 583 which indicate the portions of the bone 581 that will be cut. The implant can be attached to the bone 581 at resection surfaces and the resection lines 583 can be parallel to a joint line 585 which can define an axis of rotation 587. With reference to FIG. 98, an error can be made during resectioning of the bone 581 and the resection surfaces 588 may not be parallel to the axis of rotation 587. Attaching the implant to this defective resection surfaces 588 would result in misalignment of the implant about the Z-axis relative to the bone 581. With reference to FIG. 99, in order to correct this problem, an additional resection cut or cuts 588 may be necessary. However, once the additional resection cuts 589 are made, the resection surfaces 588 may need to be built up to provide a proper planar surface for positioning the implant in a correction position and rotation relative to the bone. With reference to FIG. 100, hybrid tack inserts 100 can be placed in the resection surfaces 588 of the bone 581 can provide the proper Z axis rotation offset so that the implant can be parallel to the axis of rotation 587. As discussed, trialing can be performed on the hybrid inserts 100 using a trail implant until proper offset inserts are found. Once the properly sized inserts are found, liquid PMMA can be applied to the bone, exposed areas of the bone inserts and the implant. The implant can be placed against the bone and hybrid bone inserts. The liquid PMMA can cure forming a chemical bond with the PMMA portions of the bone inserts and form a mechanical bond between the bone 581 and the implant.

In embodiments, the cured PMMA portions of the hybrid bone inserts 100 and/or the liquid PMMA cement 109 may have a radiopaque additive which can be detected by x-rays. The bone implant and bone can be x-rayed to determine if the hybrid bone inserts 100 are properly positioned in the bone 130 and determine if the liquid PMMA cement has been properly placed on all of the required surfaces and spaces between the bone 130 and the implant 107 to insure the implant 107 will be properly bonded to the bone 130. If errors are detected, additional PMMA cement 109 can be applied where needed.

Figure 24:
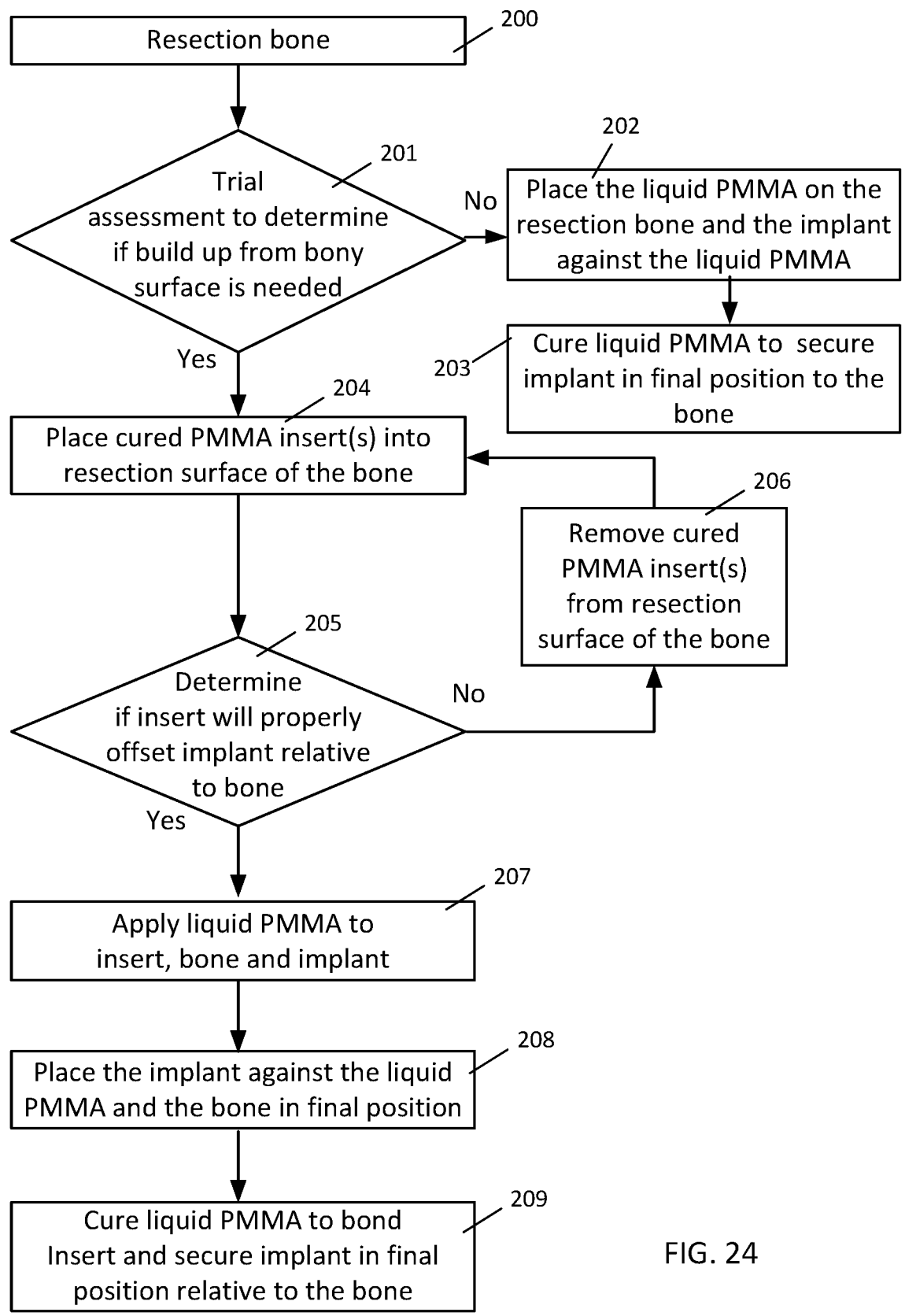
FIGS. 24-26 illustrate flow charts for adjusting PMMA inserts and bonding a final implant to a bone.
Figure 25:
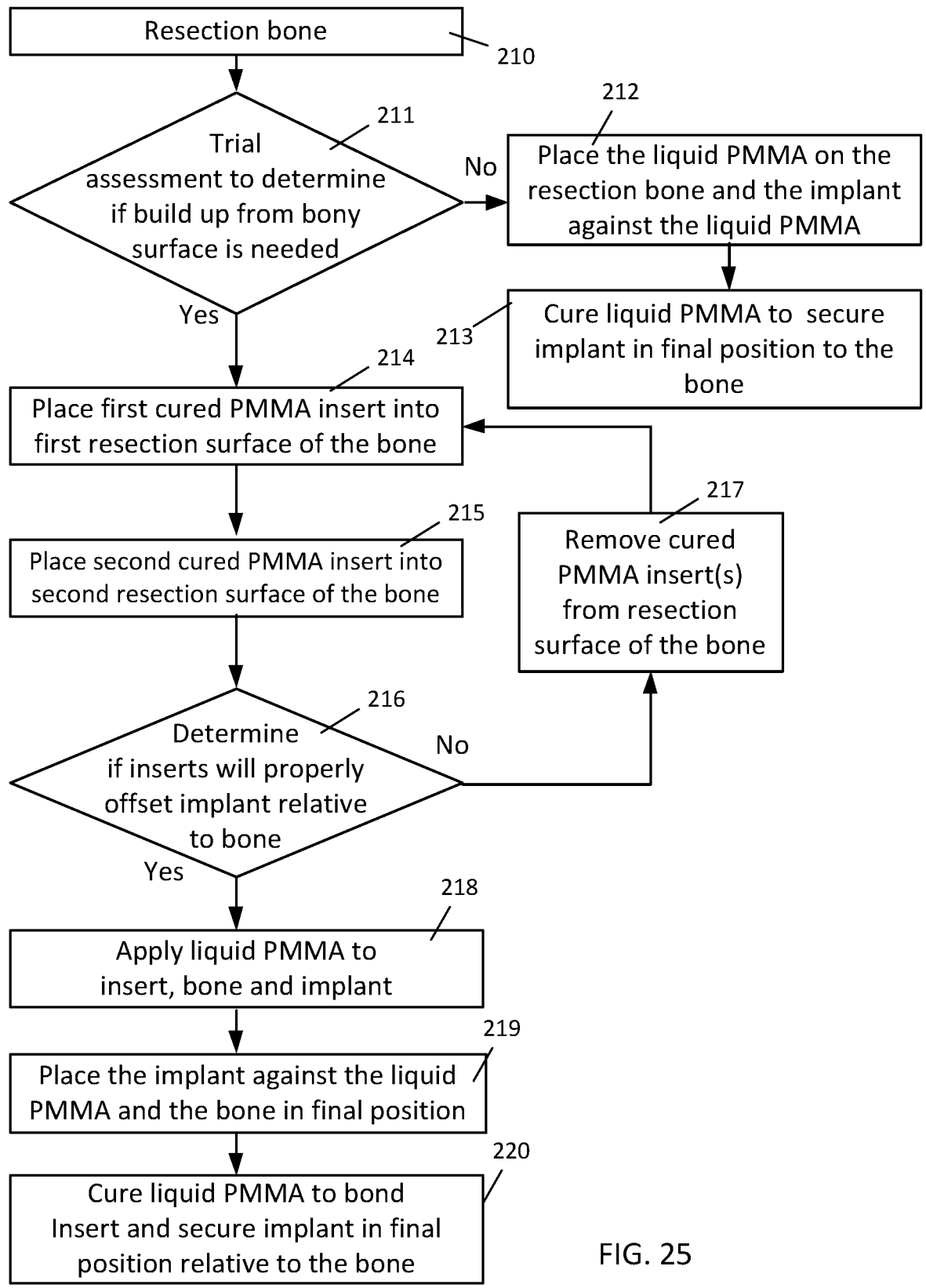
Figure 26:
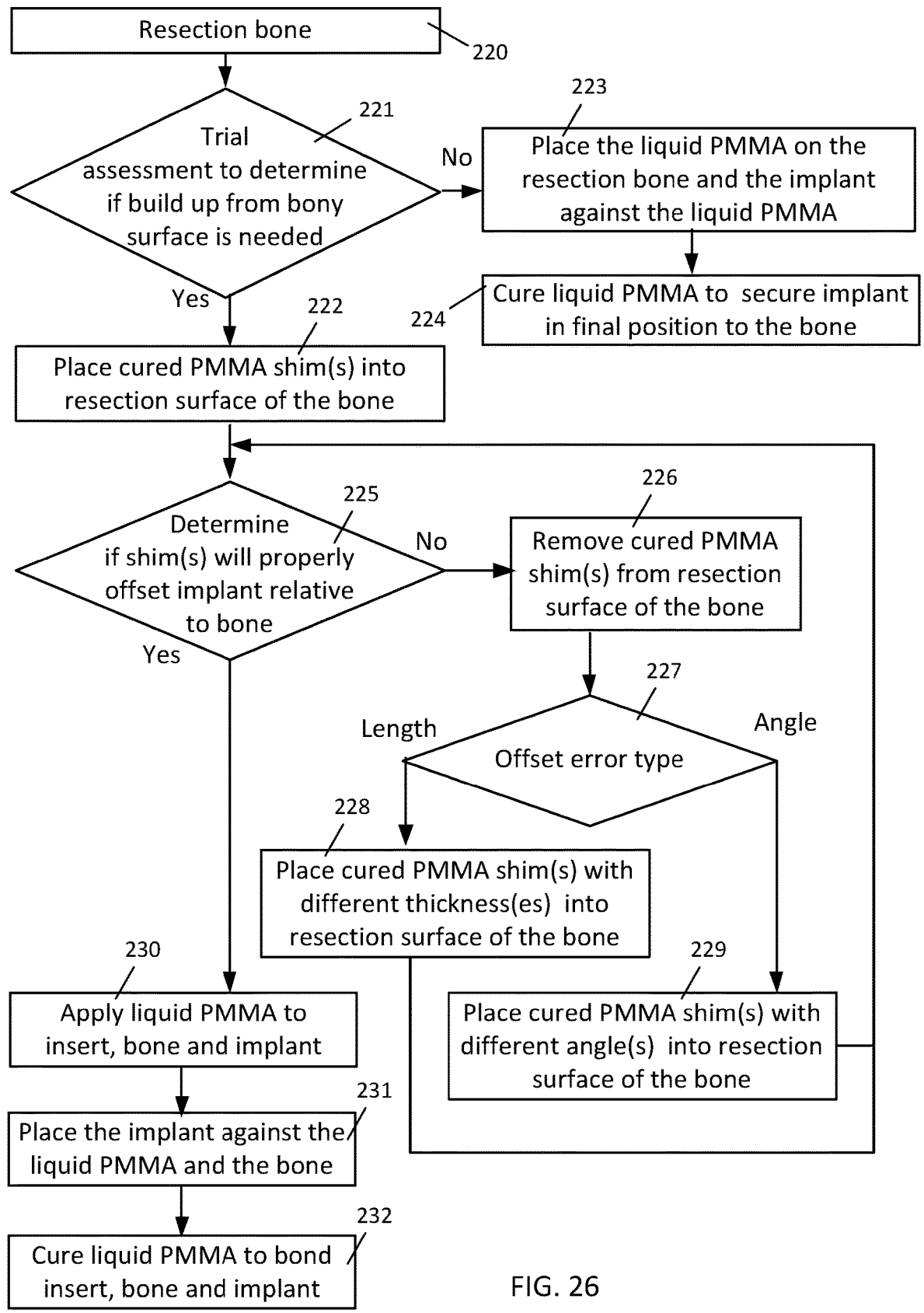

FIGS. 24-26 illustrate example flow charts describing the steps used to attach implants to a resectioned bone. With reference to the flowchart in FIG. 24, a bone is first resectioned 200. Trialing is then performed to determine if the implant will be properly positioned relative to the bone or if build up from the bony surface is needed 201. The trialing can be a test of the resection to determine if the position is correct. The trialing can depend upon the type of joint being repaired and can involve joint motion testing. The trialing will be described in more detail later. If the resection bone is proper and no build up from the bony surface is needed, liquid PMMA can be placed on the resection bone and the implant can be placed on the liquid PMMA and the bone 202. The liquid PMMA can then cure to secure the implant in the final position on the bone 203. If build up of the bony surface is needed, one or more hybrid inserts are placed into a resection surface of the bone 204. The surgeon can then determine if the one or more hybrid bone inserts will provide the proper offset 205. In some embodiments, a surgeon can use a tool such as a gauge to check the offset of the implant relative to the bone. In other embodiments, the implant can be placed against the hybrid inserts to determine the offset of the implant relative to the bone. The implant placed against the insert can be trialed for range of motion and stability to determine clinical adequacy of the correction of the implant relative to the bone. Alternatively, any other measuring method can be used to determine the offsets of the hybrid inserts. If an offset error is determined, the hybrid bone inserts can be removed from the resection surface of the bone 206 and hybrid bone inserts that provide different offsets are inserted into the resection surface of the bone 204.

In an embodiment, the surgeon can have a number of hybrid bone inserts that have different offset sizes. For example, the different hybrid bone inserts can be sized in 1 mm or other dimensional increments. In use, the user can insert the stem of the hybrid inserts and determine that the offset is the wrong length and then find a proper length offset hybrid insert based upon trial and error. In an embodiment, a surgeon can use a kit of paired hybrid inserts that can include various length offsets. In an embodiment, the hybrid inserts can be clearly marked so that the surgeon will know the different offsets of the different hybrid insert sizes which can improve the efficiency of the described procedures. The offsets of the hybrid inserts in a kit can range from 1 mm-15 mm in 1 mm increments or any other suitable range of distances and increments. So there can be 15 or more hybrid inserts each having a different offset distance. For example, the hybrid inserts can have dot markings that indicate the offset distance with each dot indicating an additional 1 mm offset. In other embodiments, the hybrid inserts can be numerically marked or color coded based upon the offset distance.

If the hybrid inserts provide the proper implant offset relative to the bone, liquid PMMA cement can be applied to the hybrid inserts, bone and implant 207. The implant is placed against the liquid PMMA which fills all gaps between the resection surface of the bone and the implant 208. In some embodiments, the liquid PMMA can be applied with a tool such as a brush or spatula to the contact surfaces of the stem sections with the hybrid insert and the implant. Liquid PMMA can also be injected with a tool such as a liquid PMMA injection gun through a nozzle into a gap between the resection surface of the bone and the implant to fill this space. Thus, the liquid PMMA can be applied to the hybrid inserts, bone and implant in various different ways. The liquid PMMA fills this space, cures and hardens to bond to the cured PMMA portions of the hybrid bone inserts on the first and second resection surfaces. The bonding of the liquid PMMA to the cured PMMA portions of the hybrid bone inserts create a high strength mechanical connection between the bone and the implant 209.

The use of hybrid inserts provides several benefits. The hybrid inserts provide a means for correcting resection errors when excess bone material has been removed. The physical strength of the PMMA connection to the bone is also improved because the stem portions of the hybrid inserts penetrate into the bone to provide ongrowth and ingrowth surfaces resulting in a stronger connection than that provided by liquid PMMA without the cured PMMA and bone interdigitation surfaces of the hybrid bone inserts. The chemical composition of the cured PMMA portions of the bone inserts and the liquid PMMA cement can be identical or substantially similar. When the liquid PMMA cures around the cured PMMA portions of the hybrid bone inserts, the solid structure formed is substantially homogeneous and the mechanical properties such as tensile, compression and shear strengths are uniform or nearly uniform across the cured liquid PMMA and cured PMMA portions of the hybrid bone inserts.

In joint arthroplasty, liquid PMMA cement rarely penetrates more than several millimeters into boney surfaces. The stem portions of the bone inserts can easily penetrate much further into the bone. When liquid PMMA cement is applied to the PMMA portions of the bone insert, the resulting construct can create a greater strength mechanical bond between the bone and the bone implant than the mechanical bond of the bone to the bone implant with only PMMA cement without the PMMA and bone ingrowth stem hybrid inserts.

With reference to FIG. 26, a flowchart for coupling an implant to a bone with hybrid inserts on multiple resection surfaces. In this embodiment, the bone is resectioned forming multiple resection surfaces 210. Trialing is then performed to determine if the implant will be properly positioned relative to the bone or if build up from the bony resection surfaces is needed 211. If the resection bone surfaces are properly positioned and no build up from the bony surface is needed, liquid PMMA can be placed on the resection bone and the implant can be placed on the liquid PMMA and the bone 212. The liquid PMMA can then cure to secure the implant in the final position on the bone 213. In build up is needed to the resection surfaces, a first hybrid bone insert is placed in a first resection surface of the bone 214 and a second hybrid bone insert is placed in a second resection surface of the bone 215. The surgeon can then determine if the first and second hybrid inserts will properly position the implant offset relative to the bone 216. If the offset is incorrect, the hybrid inserts that need to be replaced are removed from the bone 217 and replacement first and/or second hybrid inserts are placed into the bone. If the hybrid inserts provide the proper implant offset relative to the bone, liquid PMMA cement can be applied to the PMMA portions of the hybrid inserts, bone and implant 218. The implant is placed against the liquid PMMA which can fill all gaps between the resection surface of the bone and the implant 219. The liquid PMMA cures and hardens to bond to the cured PMMA portions of the bone inserts on the first and second resection surfaces. This creates a high strength PMMA structure and secures the implant to the bone 220.

As discussed above, the inventive method can be used to make length and angular adjustments to bones, such as knee implants bonded to femur bones. FIG. 26 illustrates a flow chart describing a process for making length and/or angular corrections to the implant offset relative to the bone. The bone is resectioned 220 as described. In an embodiment, the resection surfaces can be an MFC resection surface and an LFC resection surface. Trialing is then performed to determine if the implant will be properly positioned relative to the bone or if build up from the bony resection surfaces is needed 221. If the resection bone surfaces are properly positioned and no build up from the bony surface is needed, liquid PMMA can be placed on the resection bone and the implant can be placed on the liquid PMMA and the bone 223. The hybrid bone inserts are then placed into the resection surfaces of the bone 224.

If build up is needed on the resection surfaces, the surgeon can insert implants and trial the implants to determine if the implant will properly offset the implant in length and angle relative to the bone 225. If there is an offset error, one or more of the hybrid bone inserts can be removed from the resection surface 226. The surgeon can determine if the error is in length and/or angle 227. If the implant offset length is incorrect, hybrid bone inserts can be placed in the resection surfaces of the bone to correct the offset length 228. The change in offset can be controlled by using different thickness MFC and LFC hybrid inserts that can have the same offset change, i.e. both MFC and LFC hybrid inserts can be shorter or longer than the original inserts to maintain the same offset angle. If the offset angle is in error, replacement hybrid inserts having different thicknesses can be inserted into the resection surfaces of the bone 229. Once the hybrid inserts that provide the proper angular and length offset are found, liquid PMMA can be applied to the PMMA portions of the hybrid inserts, bone and implant 230. The implant can be placed against the liquid PMMA and the bone 231. The liquid PMMA can also fill the voids or gaps between the inserts, bone and implant. The liquid PMMA can cure to bond to the cured PMMA portions of the bone inserts and form a high strength structure to secure the implant to the bone 232.

As discussed, the inserts can have various different configurations. For example, in different embodiments the hybrid inserts can be tacks, rods, shims and/or any other suitable insert structure. Each of these insert configurations can have different component features and details of some possible implants will be described below.

The tack can have a general geometry of a cap, a stem that is coupled to the cap and a stem taper section at the distal end. Examples of different hybrid bone tack insert embodiments are illustrated in FIGS. 27-41. The illustrated hybrid bone tack inserts have a stem 101 and a cap 110. The cap 110 can include a Poly(methyl methacrylate) (PMMA) pre-cured cement outer surface that can chemically bond to the liquid PMMA cement. The stem 101 can include a structure material and/or coating that improves bone ingrowth and ongrowth. For example, in an embodiment the stems 101 may be made of titanium or talium which promote bone ingrowth and on growth. The stem 101 can also be structurally configured to have macrostructural fenestrations. In other embodiments, the second sections can be completely covered with ingrowth surfaces or partially covered with ingrowth surfaces.

In some embodiments, the second stem portion of a hybrid bone insert can have a porosity of about 60-70% or preferably 65% and pore sizes of about 50-900 µm or preferably 500-700 µm, can be manufactured by various processes including 3D printing, selective laser melting (SLM) or other suitable fabrication methods. In an embodiment, the stem portion of the hybrid bone insert can have a diamond lattice that can be adapted as the bask stem structure. In some embodiments, the stem portions of the hybrid bone inserts can also be coated with materials that can increase bone ingrowth. For example, in an embodiment the stem portions of the hybrid bone inserts can be treated with strontium (Sr) to increase bone quality and formation around osseointegrating implants. In other embodiments, the hybrid bone insert stems can be coated with Ti6Al4V beads and treated by anodic oxidation in $H_3PO_4$ for enhanced bone ingrowth or ongrown bioactivity. In other embodiments, any other surface features and coatings of the stem can be used to promote bone ingrowth or ongrown.

Figure 27:
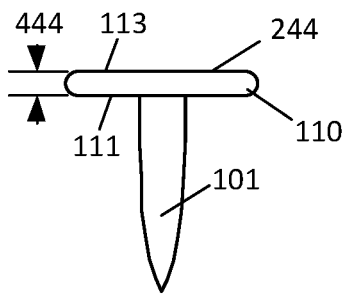

With reference to FIG. 27, in a basic embodiment, a hybrid tack insert 244 can include a cap 110 and a stem 101 in direct physical contact with the cap 110. The stem 101 can be an elongated rod having an end and a tapered body that forms a sharp distal tip. A proximal end of the stem 101 is coupled to the cap 110. The center axis of the stem 101 can be perpendicular to a plane defined by the first surface 111 and/or second surface 113 of the cap 110. The stem 101 can have various different shapes including a rounded tapered tip, a sharp tip and a sharp tip that can gradually increase in cross section size to a wider diameter at the neck portion. The stem 101 can have a thin cross section that is inserted into the bone and the cap 110 can function as a mechanical stop so that when, the stem 101 is pressed into the bone and the first surface 111 of the cap 110 contacts the external surface of the bone. As discussed, an implant can be placed against the second surface 113 of the cap 110. Thus, the offset distance of the hybrid tack insert 244 can be defined by the distance 444 between the first surface 111 and the second surface 113 of the cap 110.

Figure 28:
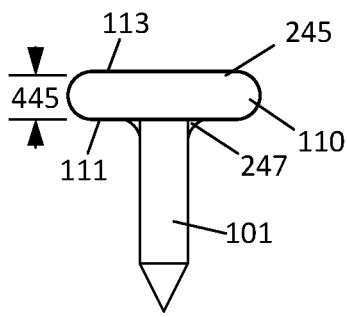
Figure 29:
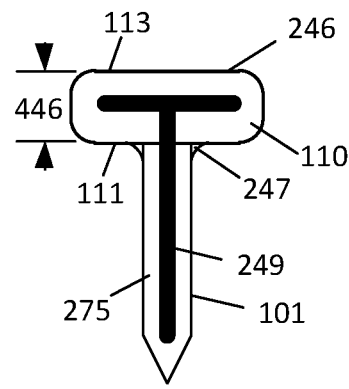
Figure 30:
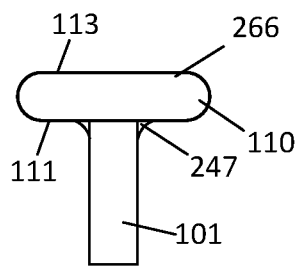

With reference to FIG. 28, another hybrid tack insert 245 is illustrated which has a thicker cap 110 having a longer distance 445 between the first surface 111 and the second surface 113 and FIG. 29 illustrates a hybrid tack insert 246 having a still longer distance 446 between the first surface 111 and the second surface 113 of the cap 110. Thus, the hybrid tack insert 246 in FIG. 28 provides a longer length implant offset than the hybrid tack insert 245 in FIG. 27 which provides a longer length implant offset than the hybrid tack insert 244 in FIG. 27. In an embodiment, a plurality of hybrid tack inserts can be available during a bone surgery to provide the required offset. For example, the hybrid tack inserts can have different cap thicknesses in 1 mm increments. Thus, during a surgical procedure, the surgeon can perform trialing using different hybrid tack inserts so that the proper tack thickness can be determined. If the hybrid tack inserts are available in 1 mm increments, the implant will be able to be positioned within 1 mm of the correct implant offset distance from the bone. The trialing process will be described later in this application.

The shapes of the stems 101 can include a tapered section which creates a compression zone when inserted into the bone and a uniform cross section zone. In FIG. 27, the stem 101 can be tapered along the entire length which compress against the bone during the insertion of the stem 101. With reference to FIGS. 27 and 28, the stem 101 can include a conical section at the distal end that forms a sharp tip and a uniform cylindrical section along the middle and proximal portions of the stem 101. During the insertion process, the tapered sections of the stem 101 can press outward against the inner diameter of the hole in the bone compressing the bone outward as the cross section diameter of the tapered section enters the bone. This compression of the bone by the stem 101 can create a seal that can prevent fluids such as liquid PMMA from flowing through this seal contact area between the stem 101 and the bone. Once the tapered section has been pressed into the bone, the cylindrical section will not further compress against the bone during the insertion.

In some embodiments, it can be important for the tack to seal out the PMMA liquid from the hole formed in the bone by the tack insert so that bone ingrowth and ongrowth can occur. With reference to FIG. 28, the diameter of the stem 101 connection adjacent to the cap 110 of the tack insert 245 can be wider than the outer diameter of the rest of the stem 101. More specifically, the junction between the stem 101 and the cap 110 can also include a radial expansion 247 which effectively expands the cross section of the stem 101 at the junction with the cap 110. The radial expansion 247 can be straight chamfer or a curved fillet between the stem 101 and the cap 110. When the tack insert 245 is inserted into the bone, the wider cross section will expand outward at the radial expansion 247 to create a physical seal with the bone. When the tack insert 245 is fully inserted into the bone hole, the wider diameter at the radial expansion 247 can have a tight fit with the upper edge of the hole when the tack is fully inserted. This tight fit seal can prevent liquid PMMA cement in the bone from entering the bone. The direct contact of the bone with the stem 101 which can then form a strong bone ingrowth bond between the hybrid tack insert 245 and the bone.

The hybrid inserts can be a composite construction that includes cured PMMA in the stem section and bone ingrowth or ongrowth materials combination with a different substrate material(s). With reference to FIG. 29, the hybrid tack insert 246 can include a tack shaped substrate 249 which can be any non-PMMA material. For the example, the substrate 249 can be a metal such as stainless steel, titanium or any other suitable metal material. The outer stem 101 material surrounding the substrate 249 can be made of a material that promotes bone ingrowth and/or on growth such as titanium, tantalum or other suitable materials. The composite material implants can be useful when higher strength tack inserts 246 are necessary. For example, the shear strength of the hybrid insert can be improved by using a metal or polymer substrate. The cap 110 can at least partially surrounded by cured PMMA 275. This construction can be achieved in various ways. For example, the tack insert 246 can be fabricated by placing the substrate 249 in a mold and that is then filled with liquid PMMA cement which is cured to form the hybrid insert 246. In other embodiments, the substrates 249 can be coated with the liquid PMMA which can cure to form the cured PMMA 275 around the substrates 249. The stem 101 portion of the insert 246 can be coated 275 with a bone ingrowth material such as strontium (Sr) to increase bone quality and formation around osseointegrating implants. In other embodiments, the hybrid bone insert stems 101 can have a coating 275 Ti6Al4V beads and treated by anodic oxidation in $H_3PO_4$ for enhanced ingrowth or ongrown bioactivity.

As discussed, the hybrid tack inserts can be inserted into the bone and the surgeon can perform trialing of the hybrid inserts using a trial implant to determine if the implant will be positioned with the correct offset and angle from the bone surface. If corrections need to be made, the surgeon must remove the hybrid tack implant(s) from the bone. In order to allow easier removal, the caps 110 can have over hang portions around the outer diameters which allow the surgeon to grasp the caps 110 and pull the hybrid tack inserts out from the bone. In FIGS. 27-29, the overhang features of the caps 110 are between the outer diameters and the first surfaces 111 of the caps 110. The surgeon can manually grasp these surfaces to pull the hybrid tack implant out of the bone. Alternatively, the surgeon may use a tool that can be placed between the bone and the over hang portions of the cap 110 to apply a removal force to the hybrid tack inserts and pull the hybrid tack inserts from the bone.

Figure 31:
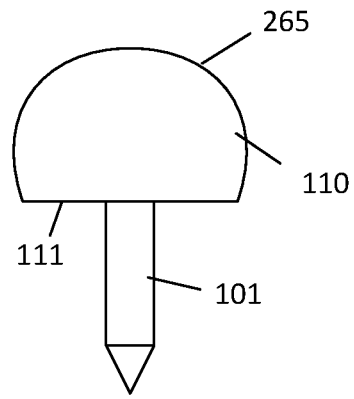

In different embodiments, the shape, thickness and geometry of the caps of the hybrid tack inserts can have any suitable geometry. For example, the caps can have an oval, circular, rectangular, triangular or any other cross section shape. The cross section can also be variable from the top to the bottom surfaces. For example, with reference to FIG. 30, an embodiment of a hybrid tack insert 266 can include a stem 101 can have a blunt distal end. With reference to FIG. 31, a hybrid tack insert 265 is illustrated having cap 110 with a spherical outer shape and a planar first surface 111 adjacent to the stem 101. The stem 101 can be inserted into bone and the first surface 111 can function as a stop against the outer surface of the bone. The spherical surface can provide a point of contact offset from the bone at any angle relative to the hybrid tack insert 265.

In other embodiments, the outer surface of the caps or heads can have relief or flow channels for excess PMMA liquids. The caps may also include, recesses, slots, grooves, holes and other features that can improve the binding with the surrounding or adjacent liquid PMMA cement. The cap can include a plurality of holes that extend from one side to an opposite side of the cap. The cap can have a plurality of slots in the side surfaces of the cap. Alternatively, the cap can have grooves or recesses formed in the lower and side surfaces. In all of these embodiments, the surrounding or adjacent liquid cement can flow into these cap surface features and harden. These features increase the surface area and provide additional structures that can capture and prevent the hardened PMMA from separating. The caps may also include holes that extend through the cap or recesses that the excess liquid PMMA cement can flow into and harden so that it does not flow out of the contact areas of the tack insert with the bone.

The bonding of the hybrid tack inserts to the bone and implant can be improved with greater interdigitation between the liquid PMMA cement, the PMMA portions of the hybrid inserts, the implant and the bone. The cap geometries can be designed to maximize liquid PMMA cement penetration and increase the contact area between the cured PMMA areas of the hybrid insert and the liquid PMMA cement for improved interdigitation. In the tack insert embodiments illustrated in FIGS. 32-34, the surrounding or adjacent liquid cement can flow into these cap surface features and harden. These features increase the surface area and provide additional structures that can capture and prevent the hardened PMMA from separating. The caps may also include holes that extend through the cap or recesses that the excess PMMA liquid can flow into and harden so that it does not flow out of the tack area.

Figure 32:
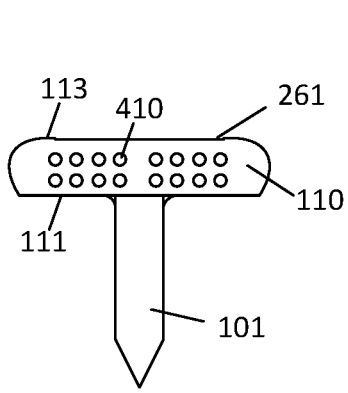
Figure 33:
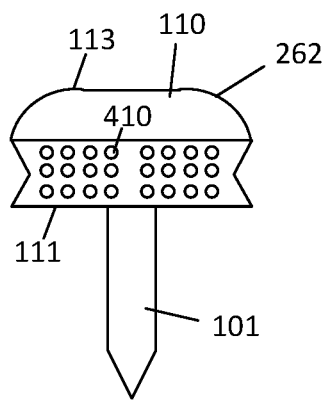
Figure 34:
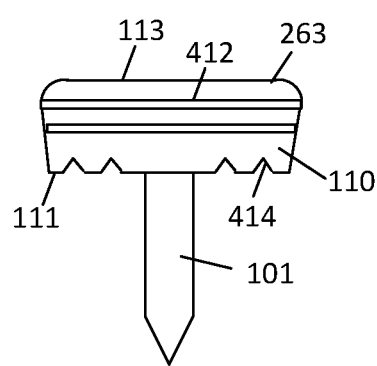

With reference to FIG. 32, a hybrid tack insert 261 can include a cap 110 having a plurality of holes 410 that extend from one side to an opposite side of the cap 110 or only partially into the cap 110. With reference to FIG. 33, a hybrid tack insert 262 can include a cap 110 having a more complex geometry. The cap 110 can which can have an "hour glass" shape which increases the contact surface area and also improves liquid PMMA cement penetration and bonding strength. The cap 110 can also include a plurality of holes 410 that extend from one side to an opposite side of the cap 110 or only partially into the cap 110. The outer diameter of the cap 110 can include a concave surface which can allow a surgeon to grasp and remove the hybrid tack insert 262. The cap 110 can be thicker to provide a greater offset of the hybrid implant relative to the bone. With reference to FIG. 34, in another illustrated example, a hybrid tack insert 263 can include a cap 110 can have a plurality of slots in the side surfaces of the cap. The cap 110 can also have recesses 414 such as grooves or other features formed in the first surface 111 of the cap 110. The outer diameter of the cap 110 can create an over hang that can allow the surgeon to grasp and remove the hybrid tack insert 263.

With reference to FIGS. 35-37, another embodiment of a hybrid tack insert 264 is illustrated. In this embodiment, the cap 110 can have a concave first surface 111 and a convex 113 upper surface. FIG. 35 illustrates a side view with the stem 101 extending away from the first surface 111 of the cap 110. The cap 110 may only contact the bone at several outer bone contact points of the cap 110. FIG. 36 illustrates a top view of the hybrid tack insert 264 which more clearly shows the shape of the cap 110 which can have several outer points and concave regions between the outer points. In this embodiment the cap 110 is not circular. With reference to FIG. 37, the hybrid tack insert 264 is illustrated after the stem 101 has been placed in a bone 130 with the cap 110 only contacting the bone 130 at a few points. In this embodiment, the liquid PMMA can flow between the cap 110 and the bone 130 to improve the bonding of the hybrid tack insert 264 to the bone 130.

In other embodiments, the hybrid tack inserts can be designed to provide various other features which may be useful for different types of surgical procedures. With reference to FIGS. 38 and 39, the stems 101 of the hybrid tack inserts can be designed to promote bone ingrowth and ongrowth and prevent removal from the bone once inserted. With reference to FIG. 38, the hybrid tack insert 267 can have a stem 101 with angled barbed protrusions 259 which are angled away from the tip of the stem 101. The angled protrusions 259 can increase the contact area with the cured PMMA and the liquid PMMA cement. When the stem 101 of the hybrid insert tack 267 is inserted into the bone, the angled protrusions 259 on the stem 101 and the tip of the stem 101 can compress against the stem 101 during insertion by the inner surfaces of the bone hole. However, when the stem 101 is pulled in a direction out of the bone, the outer ends of the angled protrusions 259 will contact the inner diameter of the bone holes and resist removal of the tack insert 267 from the bone.

With reference to FIG. 39, another embodiment of a hybrid tack insert 268 is illustrated with a tapered stem 101 that has angled protrusions 259 which will allow insertion but resist removal from the bone. As discussed, the stem 101 can have a construction and coatings which promote bone ingrowth and ongrowth bioactivity. The cap 110 can include lower recesses 414 such as grooves or other features formed in the cap 110 which can improve interdigitation with the bone due to ingrowth. In the embodiments illustrated in FIGS. 38 and 39, the surgeon may determine the proper offset with other tack inserts and once the proper insert offset is known, the anti removal tack insert having the proper offset can be placed in the bone.

In different embodiments, the inventive hybrid insert can include a self-tapping screw configuration. With reference to FIG. 40, the stem 101 of the hybrid insert 264 can have helical threads 258. In this embodiment, the hybrid insert 264 can be rotated about a center axis of the stem 101 so the threads engage the inner diameter of a drilled bone hole or alternatively, the hybrid insert 264 can create the hole in the bone. The hybrid insert 264 can be driven into the bone by rotating the helical threads 258 until the cap 110 contacts the outer surface of the bone. The cap 110 of the hybrid insert 264 can have surface features that allow tools to engage the cap 110 so that a torque can be applied to rotate the stem 101. With reference to FIG. 41, a top view of a cap 110 of the hybrid insert 264 is illustrated which includes a hexagonal cross section recess 416 which can correspond to a hex wrench. The hex wrench can be inserted into the hex recess 416 and a torque can be applied to the wrench to rotate the hybrid insert 264. The threads 258 can engage the inner surface of the hole in the bone and drive the track insert 264 into the bone. The wrench can continue to rotate the hybrid insert 264 until the cap 110 contacts the outer surface of the bone. The surgeon can trial the offset of the hybrid insert 264 and if an adjustment needs to be made, the hybrid insert 264 can be removed by rotating the cap 110 in the opposite direction and the hybrid insert 264 can be replaced with a different hybrid insert having a different offset.

In other embodiments of the present invention, multiple hybrid rod inserts can be inserted into the bone surface. The hybrid rod inserts can include a cured PMMA portion and a stem portion made of a bone ingrowth/ongrowth material such as titanium or tantalum which has surface features and/or coatings which promote bone ingrowth and ongrowth. The stem portions of the hybrid rod inserts can be pressed into the bone and the bone can grow into and onto the inserted portions of the hybrid rod insert. Liquid PMMA cement can be applied to the exposed PMMA surfaces of the hybrid rod insert. The implant can be placed on the liquid PMMA cement. The PMMA cement can harden and cure to chemically bond to the PMMA portions of the hybrid rod inserts and mechanically bond the implant to the bone. The hybrid rod inserts can be inserted into the bone at variable different angles which can further improve the strength of the bone bonding connection interface. In different embodiments, the hybrid rod inserts can include various geometric features such as: tapered, threaded, posts, anchor constructs, etc. This system can provide improved bone ingrowth and ongrowth interdigitation. The bonding surface of the implant can include fenestrations, grooves, roughness, etc. that can provide additional bonding surfaces for the bone ingrowth and ongrowth interdigitation.

Figures 42, 43, 44:
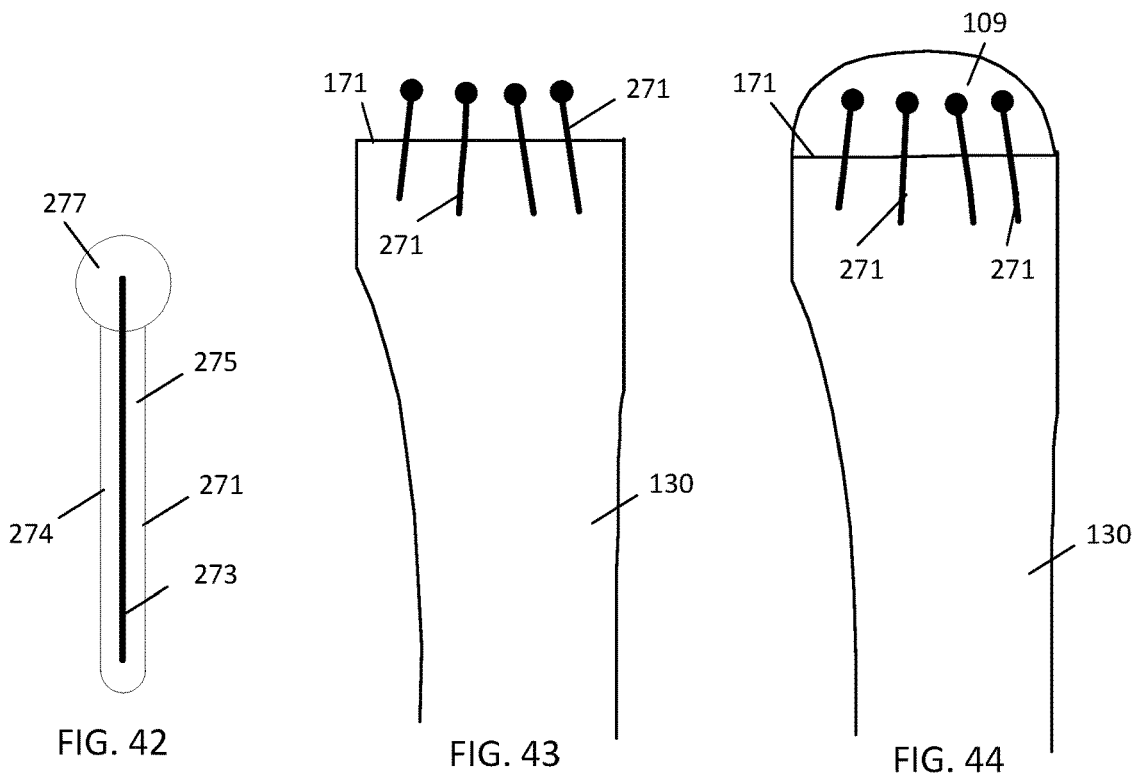
FIG. 42 illustrates a side view of a PMMA rod insert.
FIG. 43 illustrates a side view of a resectioned bone with PMMA rod inserts.
FIG. 44 illustrates a side view of a resectioned bone with PMMA rod inserts and liquid PMMA cement.

With reference to FIG. 42, an embodiment of a hybrid rod insert 271 can include a stem 274 with bone interdigitation features and a head 277 covered with cured PMMA 278. In some embodiments, the hybrid rod inserts 271 can be composite structures for higher strength. Composite rod insert structures 271 can include a core substrate 273 made of materials such as stainless, titanium, polymer, ceramic, metal, and plastic which can have higher compression, tensile and shear strengths. The head 277 can then be covered with a PMMA material 278 which can completely or partially surround the head 277. The stem 274 can be made or coated with a bone ingrowth/ongrowth material 275 such as titanium or tantalum. In an embodiment the stem portions of the hybrid rod insert can be treated with strontium (Sr) to increase bone quality and formation around osseointegrating implants. In other embodiments, the hybrid rod insert stems can be coated with Ti6Al4V beads and treated by anodic oxidation in $H_3PO_4$ for enhanced bone ingrowth or ongrown bioactivity. In different embodiments, the PMMA material 278 and bone ingrowth/ongrowth material 275 can be molded around the core substrate 273 structures or applied to the core substrate 273 structures as coatings.

The hybrid rod inserts 271 can come in various shapes and have various different structural features for example, the hybrid rod insert structures can include: a stem alone or possibly both a stem 274 and a PMMA head 277. In the illustrated example, the rod insert 271 can include elongated stems with a spherical shaped head 277 made or covered with PMMA at one end of the stem 274. The head 277 can provide a larger surface area so that the stem 274 portion can be physically pushed into the hole in the bone or a bony surface so that the rebar rod inserts 271 function like a pushpin as previously described in the hybrid tack insert embodiments.

In other embodiments, the stem can be: solid, cannulated, fenestrated and the outer surface can be smooth, textured, threaded, grooved or have any other surface features. These surface features can provide improved grip to the cement and other adhesives. If the rebar device includes a head, the head can provide additional functional features. For example, if the stem portion is threaded, the head can have features that can allow a torque to be applied to the stem that can rotate the rebar device and drive the rebar device into the bone. For example, the upper surface of the head can have slots that can engage an end of a screw driver. Alternatively, the outer edges of the head can have surfaces that are parallel to the center rotational axis of the stem which can allow a wrench to apply a torque force to the head and stem.

With reference to FIG. 43, a plurality of hybrid rod inserts 271 are inserted into an exposed attachment surface 171 (surface not labeled) of the bone 130. The exposed surface 171 can be a resectioned surface as described above. However, in other embodiments, the exposed surface 171 of the bone can be an exposed bony surface which can be at least one of the following types of bone: a metaphyseal bone, a cancellous bone, a trabecular bone, a porous bone, or a sclerotic bone. The exposed surface 171 can be drilled or alternatively, the hybrid rod inserts 271 can be pressed directly into the exposed surface 171. The angles of the hybrid rod inserts 271 within the bone 130 can be variable so that the hybrid rod inserts 271 may not be parallel to each other. However, in other embodiments, the hybrid rod inserts 271 can be perpendicular to the exposed surface 171 and parallel to each other.

Figures 45, 46:
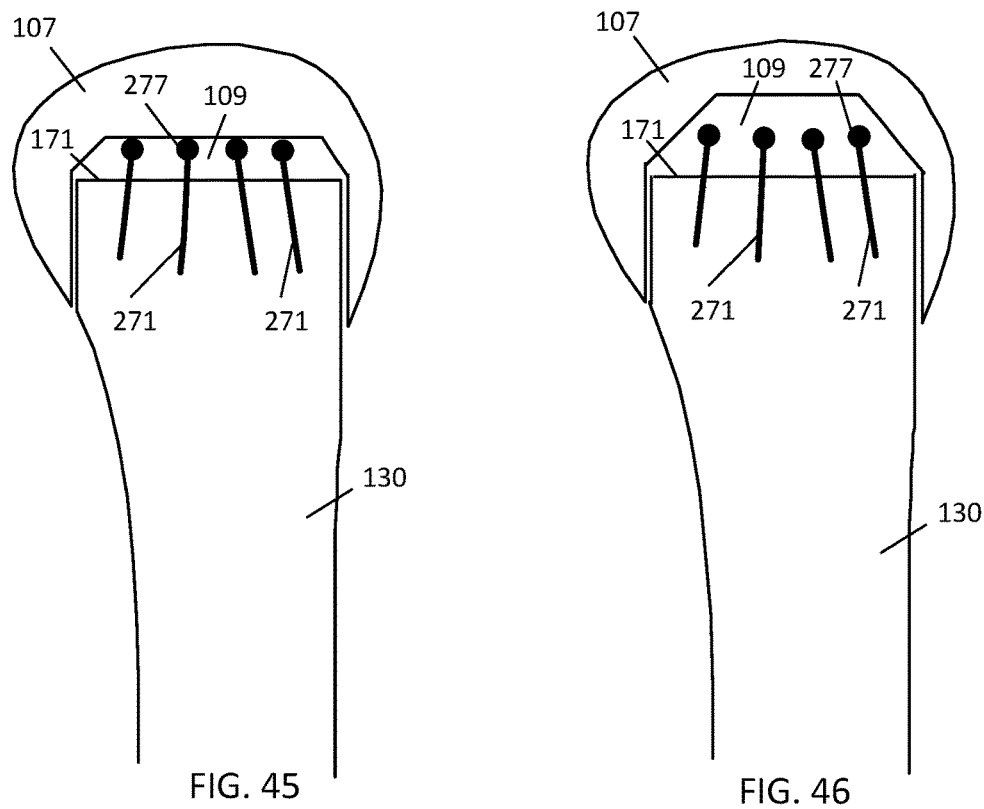
FIGS. 45 and 46 illustrate side views of resectioned bones with PMMA rod inserts and PMMA cement bonded to final implants.

With reference to FIG. 44, a liquid PMMA 109 can be applied to the exposed portions of the hybrid rod inserts 271 and the exposed surface 171. The liquid PMMA 109 may not flow into the holes formed in the bone 130 so that bone ingrowth or ongrowth with the inserted stem portion of the hybrid rod inserts 271 can occur. The liquid PMMA 109 can have sufficient viscosity to be manually pliable. It can be desirable to remove all air bubbles in the liquid PMMA 109 to maximize the strength of the PMMA when it cures. The implant 107 is placed on the liquid PMMA 109 which can fill the contact areas between the implant 107 and the bone 130. With reference to FIG. 45, the inner surfaces of the implant 107 may be in direct physical contact with the heads 277 of the hybrid rod inserts 271. With reference to FIG. 46, the implant 107 may not contact the hybrid rod inserts 271. The position and offset of the implant 107 relative to the bone 130 can be adjusted while the PMMA 109 is in liquid form. Because the implant 107 does not come into physical contact with the hybrid rod inserts 271, the implant 107 can be manually positioned. Once properly positioned, the implant 107 can be held in a stationary position relative to the bone 130 until the PMMA cures to bond the implant 107 to the bone 130 and hybrid inserts 271.

Figure 47:
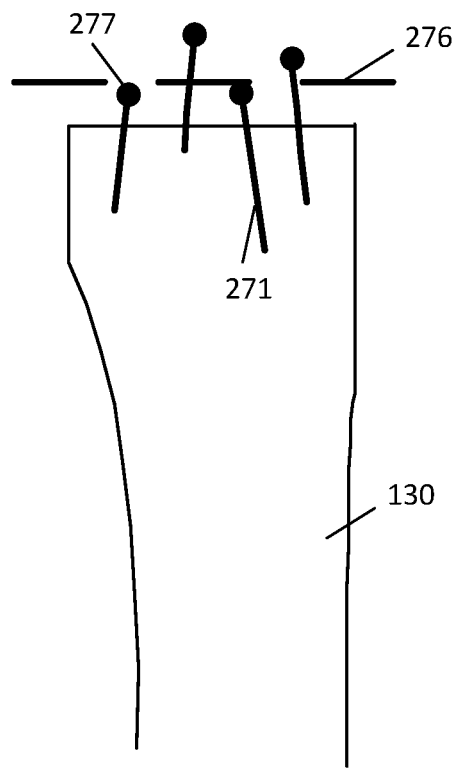
FIGS. 47 and 48 illustrate side views of resectioned bones with PMMA rod inserts.
Figure 48:
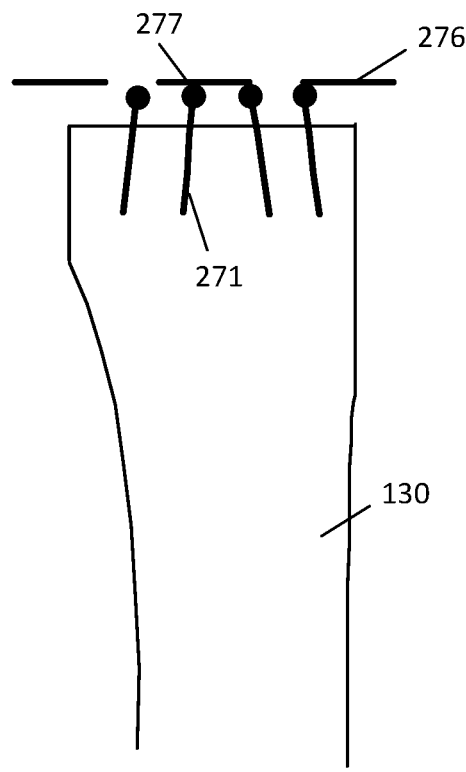
Figure 49:
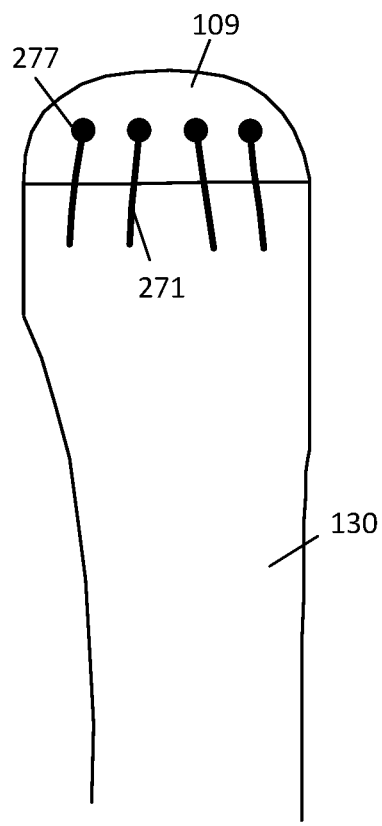
FIG. 49 illustrates a side view of a resectioned bone with PMMA rod inserts and liquid PMMA cement.
Figure 50:
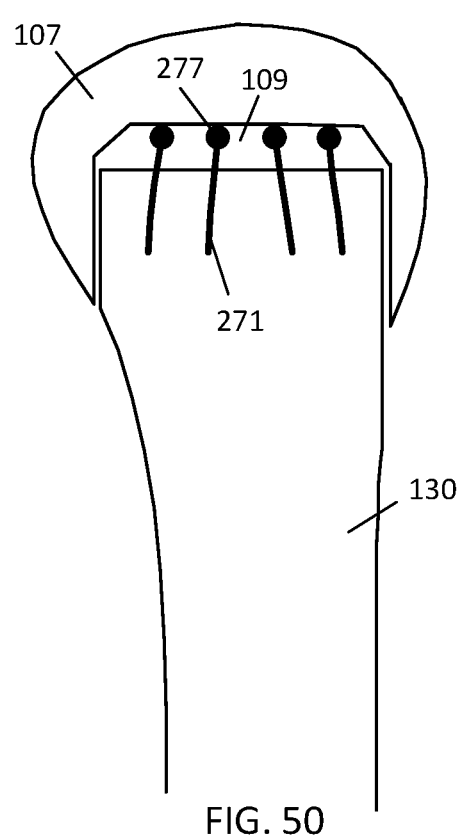
FIG. 50 illustrates a side view of a resectioned bone with PMMA rod inserts and liquid PMMA cement bonded to a final implant.

In other embodiments, the hybrid rod inserts 271 can be adjusted to control the offset of the implant relative to the bone. With reference to FIG. 47, the bone 130 is illustrated with a plurality of hybrid rod inserts 271 and a required offset plane line 276 is illustrated. Some of the hybrid rod inserts 271 extend beyond the offset plane line 276 while other hybrid rod inserts 271 can be below the offset plane line 276. With reference to FIG. 48, the hybrid rod inserts 271 that do not match the offset plant line 276 have been replaced with hybrid rod inserts 271 that match the offset plane line 276. Alternatively, the hybrid rod inserts 271 can be pressed farther into the bone to match the offset plane line 276. In the illustrated embodiment, the hybrid rod inserts 271 have PMMA heads 277 which can be aligned with the offset line 276 and contact the implant 107. With reference to FIG. 49, once the hybrid inserts 271 are properly positioned relative to the offset plane line 276, liquid PMMA cement 109 is placed on the exposed portions of the hybrid rod inserts 271 and the exposed attachment surface 171 of the bone 130. With reference to FIG. 50, the implant 107 is placed on the bone 130 with the implant 107 in direct physical contact with the heads 477 of the hybrid rod inserts 271.

Figure 51:
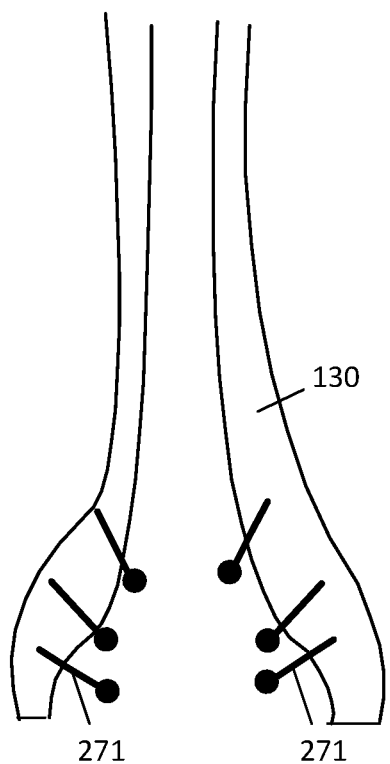
FIG. 51 illustrates a bone with PMMA rod inserts inserted into internal surfaces.
Figure 52:
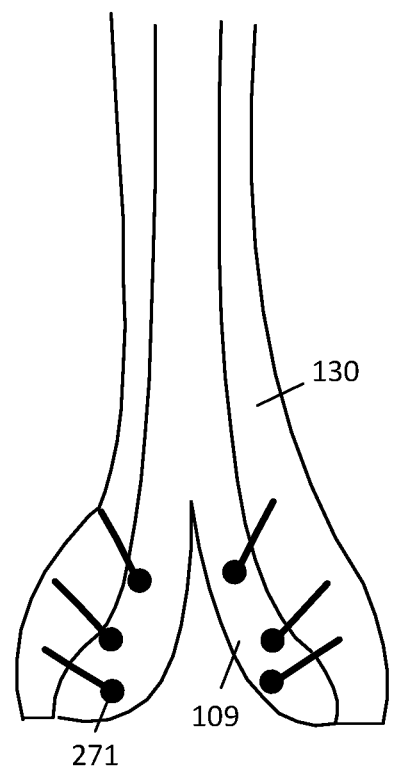
FIG. 52 illustrates a bone with PMMA rod inserts in internal bone surfaces and liquid PMMA cement.
Figure 53:
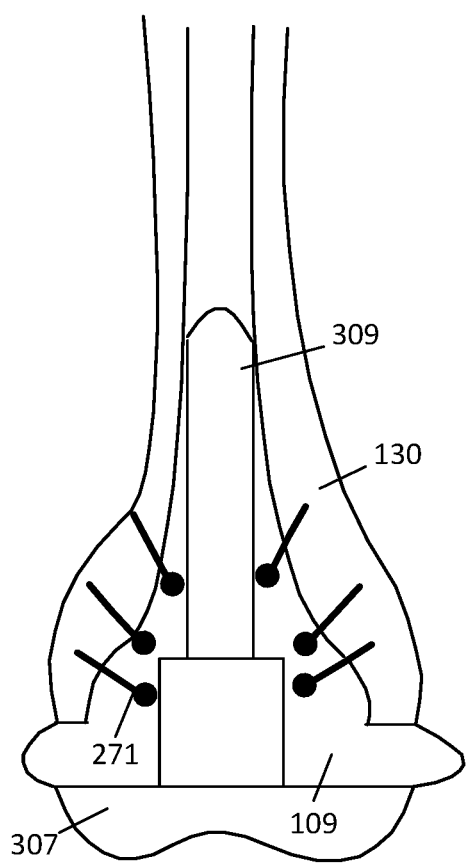
FIG. 53 illustrates a bone with PMMA rod inserts in internal bone surfaces and a final implant inserted into the liquid PMMA cement.
Figure 54:
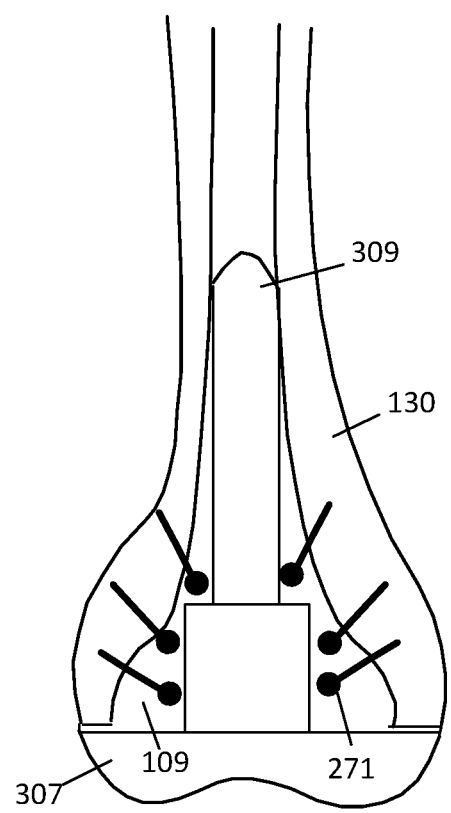
FIG. 54 illustrates a bone with PMMA rod inserts in internal bone surfaces and a final implant bonded to the bone with the liquid PMMA cement.

In other embodiments, hybrid rod inserts 271 can be used to improve the bonding of an implant 307 that extends into the bone 130. In this embodiment, the implant 307 may include an elongated portion 309 that is inserted into the bone 130 and is partially surrounded by the bone 130. With reference to FIG. 51, a bone 130 cross section is illustrated. An end of the bone has been resected and a plurality of hybrid rod inserts 271 placed on inner surfaces of the bone 130. In an embodiment, the hybrid rod insert 271 positions can be checked or trialed to determine if they are properly positioned within the bone 130. If any changes are required, the hybrid rod inserts 271 can replaced or adjusted. With reference to FIG. 52, once the hybrid rod inserts 271 are correctly positioned, liquid PMMA 109 can be applied to the exposed surfaces of the bone 130 and exposed areas of the hybrid rod inserts 271. Liquid PMMA 109 should not be placed in the bone hole between the hybrid rod inserts 271 and the bone so that ingrowth and ongrowth between the bone and hybrid rod inserts 271 can occur. With reference to FIG. 53, the elongated portion 309 of the implant 307 is inserted into the bone 130 between the hybrid rod inserts 271 which can guide the elongated portion 309 into the bone 130. With reference to FIG. 54, the implant 307 has been fully inserted into the bone 130 and the liquid PMMA 109 can cure to bond the implant 307 to the bone 130 and hybrid rod inserts 271.

Figure 55:
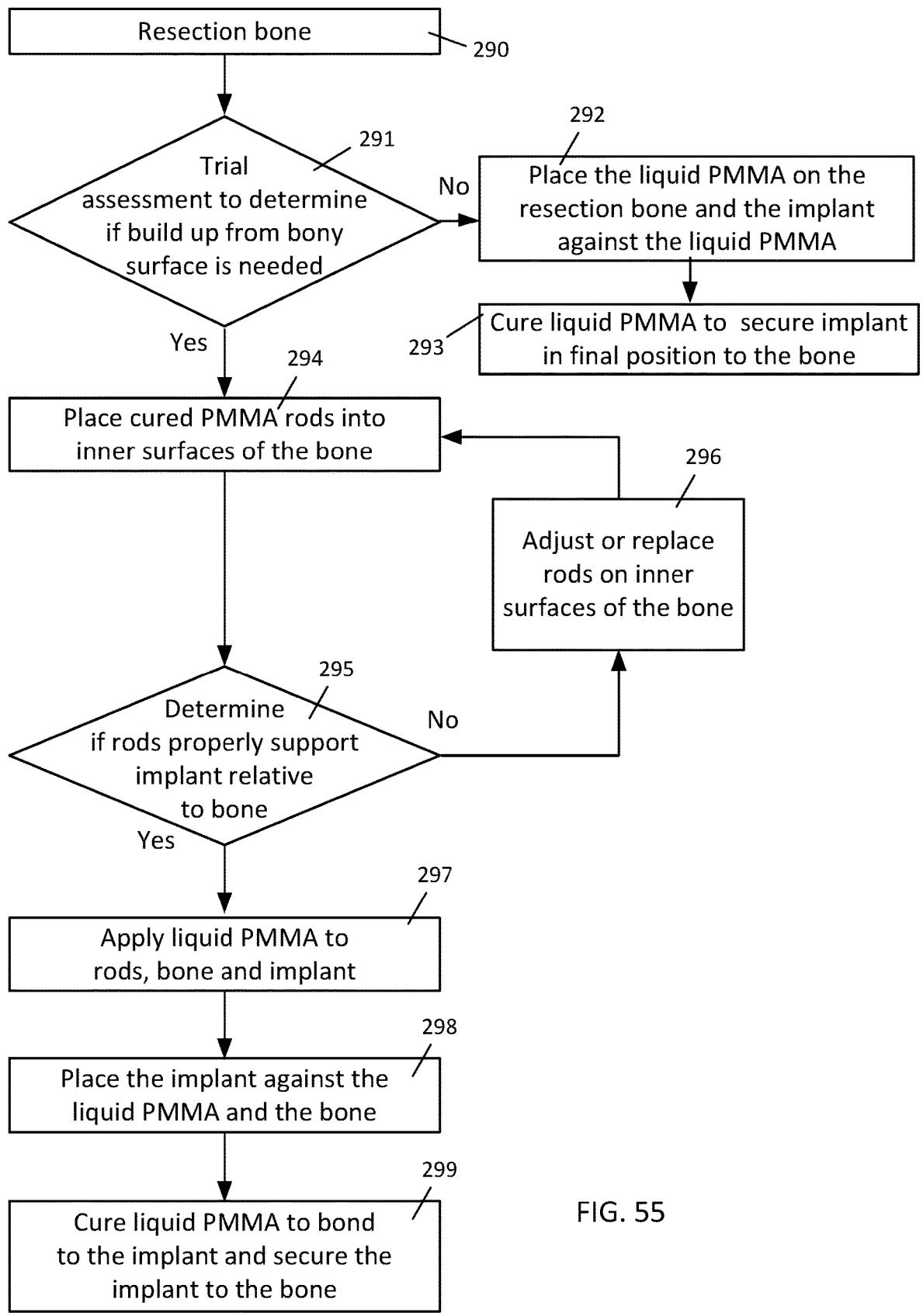
FIG. 55 illustrates a flow chart of for adjusting PMMA rod inserts and bonding a final implant to a bone.

With reference to FIG. 55, a flow chart is illustrated describing the process steps for bonding implants to the bone using the rod inserts. A bone can be resectioned 290. Trialing is then performed to determine if the implant will be properly positioned relative to the bone or if build up from the bony surface is needed 291. If the resection bone is proper and no build up from the bony surface is needed, liquid PMMA can be placed on the resection bone and the implant can be placed on the liquid PMMA and the bone 292. If build up from the bony surface is required, the surgeon can then place hybrid rod inserts into the inner surfaces of the bone 294. The hybrid rod inserts can be trialed to determine if the rod inserts are properly positioned to support the implant offset relative to the bone 295. If the hybrid rod inserts are not properly positioned, the surgeon can adjust or replace the hybrid rod inserts on the inner surfaces of the bone 296. Once the hybrid rod inserts are properly positioned, liquid PMMA cement can be applied to the exposed areas of the hybrid rod inserts and bone 297. The surgeon can then place the implant against the liquid PMMA and the bone 298. The liquid PMMA cement can be cured to bond to the rod inserts and the implant can be secured to the bone 299. Liquid PMMA should not be placed in the bone hole between the hybrid rod inserts 271 and the bone so that ingrowth and ongrowth between the bone and hybrid rod inserts can occur.

Figure 56:
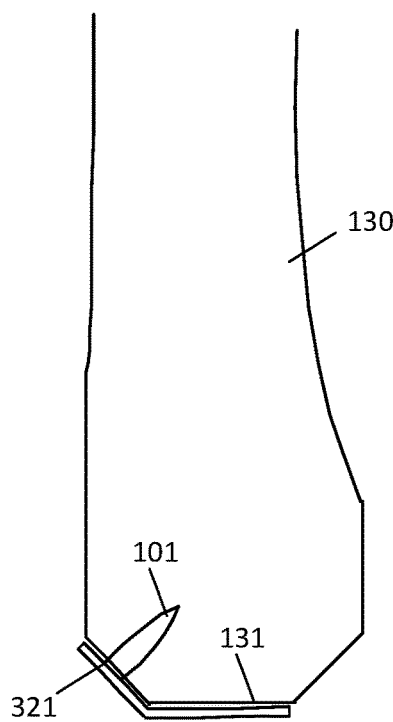
FIG. 56 illustrates a bone with a shim on anterior and distal surfaces.
Figure 57:
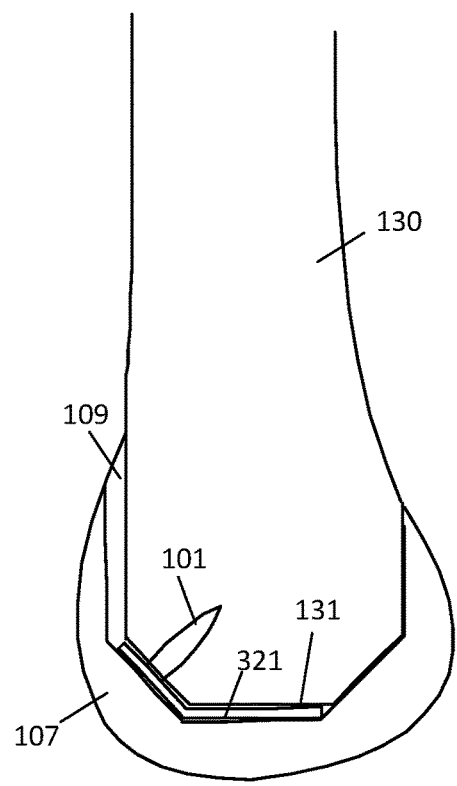
FIG. 57 illustrates a bone with a shim on anterior and distal surfaces bonded to a final implant.

In other embodiments, the planar and/or angular hybrid shim inserts can be used to adjust the implant offset relative to the bone. Hybrid shim inserts can include a planar or an angled shim structure which is made of cured PMMA and coupled to a stem made of a material with surface features that promote bone ingrowth and/or ongrowth. Only the stem portion of the hybrid shim inserts may be inserted into the bone. The shims can be placed over one or more bony surfaces with the stem pressed into the one or more bony surfaces. With reference to FIG. 56, in an embodiment a hybrid shim insert 321 having a stem 101 can include a structure material and/or coating that improves bone ingrowth and ongrowth. For example, in an embodiment the stems 101 may be made of titanium or talium which promote bone ingrowth and on growth. The stem 101 can also be structurally configured to have macrostructural fenestrations. In other embodiments, the second sections can be completely covered with ingrowth surfaces or partially covered with ingrowth surfaces. The stem 101 does not include PMMA and can be pressed into an anterior resection surface 131 of a bone 130. The surgeon can do a trial off of the hybrid shim insert 321 using a trial implant (not shown). Based upon the trial results, the surgeon can determine if the hybrid shim insert 321 is the proper thickness or if the hybrid shim insert 321 needs to be replaced. If necessary, the hybrid shim insert 321 can be removed and replaced with a hybrid shim insert having a different thickness that provides a proper implant offset and angle. With reference to FIG. 57, once the proper size hybrid shim insert 321 is successfully trialed, liquid PMMA cement 109 can be applied to the implant 107, the cured PMMA portions of the hybrid shim insert 321 and the resection surfaces 131 of the bone 130. The liquid PMMA cement 109 can fill all of the spaces between the bone 130 and the implant 107 and cure to chemically bond to the cured PMMA portion of the hybrid shim insert 321 and mechanically bond the implant 107 to the bone 130. The liquid PMMA may not contact the stem 101 which can have interdigitation surfaces and coatings which promote bone ingrowth or bone ongrowth as described above.

Figure 58:
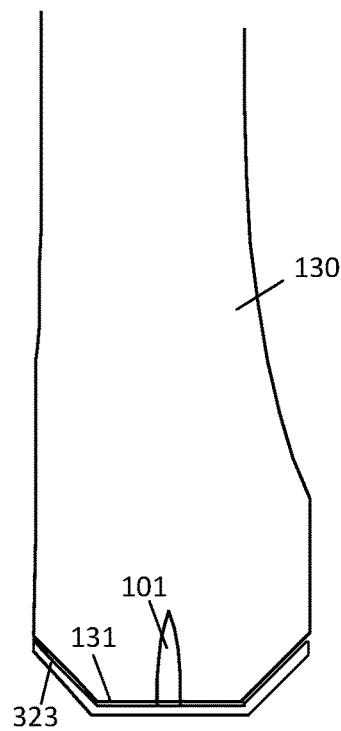
FIG. 58 illustrates a bone with a shim on anterior, distal and posterior surfaces.
Figure 59:
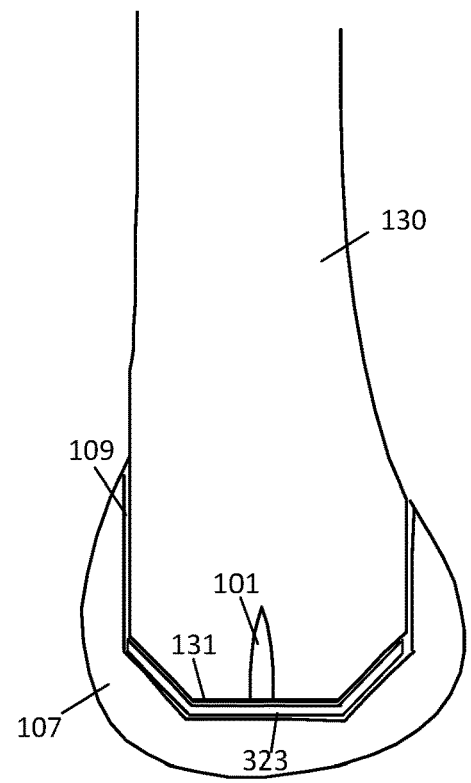
FIG. 59 illustrates a bone with a shim on anterior, distal and posterior surfaces bonded to a final implant.

With reference to FIG. 58 in other embodiments, a hybrid shim insert 323 can be designed to cover other bony surfaces 131 of the bone 130. In this example, the hybrid shim insert 323 can cover the anterior, distal and posterior bony surfaces 131 of the bone 130. The stem 101 can include a structure material and/or coating that improves bone ingrowth and ongrowth. In this embodiment the stem 101 has been pressed into the distal bony surface 131. The surgeon can use a trial implant to perform trial testing on the shim 323 to determine if the hybrid shim insert 323 is the proper thickness to provide the proper implant offset or if the hybrid shim insert 323 needs to be replaced with a different sized shim. With reference to FIG. 59, once the proper hybrid shim insert 323 is found, the liquid PMMA cement 109 can be applied to the implant 107, cured PMMA portions of the hybrid shim insert 323 and (anterior, distal and posterior) resection surfaces 131 of the bone 130. The liquid PMMA cement 109 can fill all of the spaces between the bone 130 and the implant 107 and cure to chemically bond to the PMMA portions of the hybrid shim insert 323 and mechanically bond the implant 107 to the bone 130.

Figure 60:
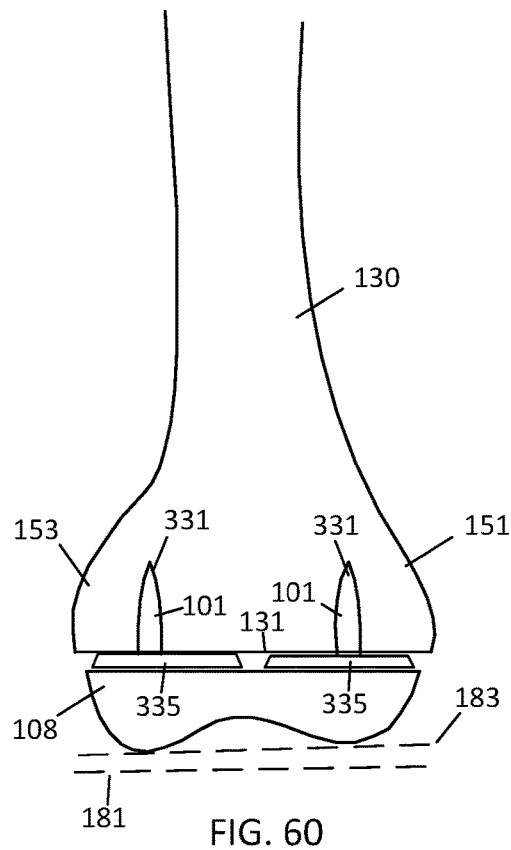
FIG. 60 illustrates an anterior view of a bone with PMMA shim inserts with a trial implant.
Figure 61:
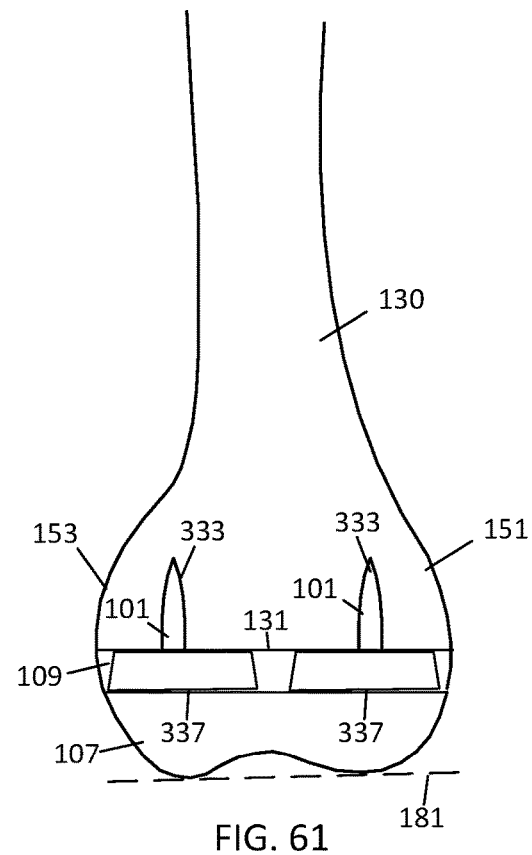
FIG. 61 illustrates an anterior view of a bone with PMMA shim inserts with a final implant.

The hybrid shim insert can be used to correct length and angular offset of the implant relative to the bone. As discussed, the surgeon can test the offset of the inserts by performing trialing processing with a trial implant placed on the inserts. The trialing can include range of motion measurements for joints and tension testing. With reference to FIG. 60, the proper predetermined length offset of the implant relative to the bone 130 can be represented by line 181. However, in the illustrated embodiment, the offset line 183 provided by the hybrid shim insert 335 and the trial implant 108 is substantially shorter than the proper offset line 181. Based upon the trialing, the surgeon can determine that thicker implant hybrid shim inserts are needed. With reference to FIG. 61, the length of the offset between the bone 130 and the implant 107 has been increased by removing the original hybrid shim insert (335) and replacing them with thicker hybrid shim insert 337 so the offset of the final implant 107 matches the proper predetermined length offset line 181. In other embodiments, if the offset position of the implant 107 needs to be shortened, the inserts can be replaced with thinner shims. In this embodiment, the angle of the resection surface 131 was correct, so the hybrid shim insert 337 can have the same thickness so that the angle of the implant 107 is not changed relative to the bone 130. Liquid PMMA 109 can be applied to the bone 130, hybrid shim insert 337 and implant 107 to chemically bond the PMMA cement 109 to the PMMA portions of the hybrid shim insert 337 and mechanically bond the implant 107 to the bone 130. Over time, the bone can ingrow and ongrow onto the stem 333 as described above.

Figure 62:
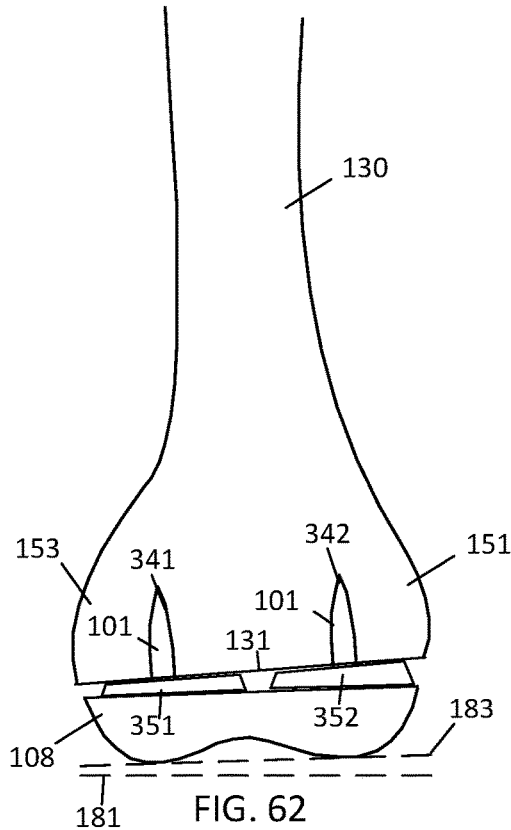
FIG. 62 illustrates an anterior view of a bone with PMMA shim inserts with a trial implant.
Figure 63:
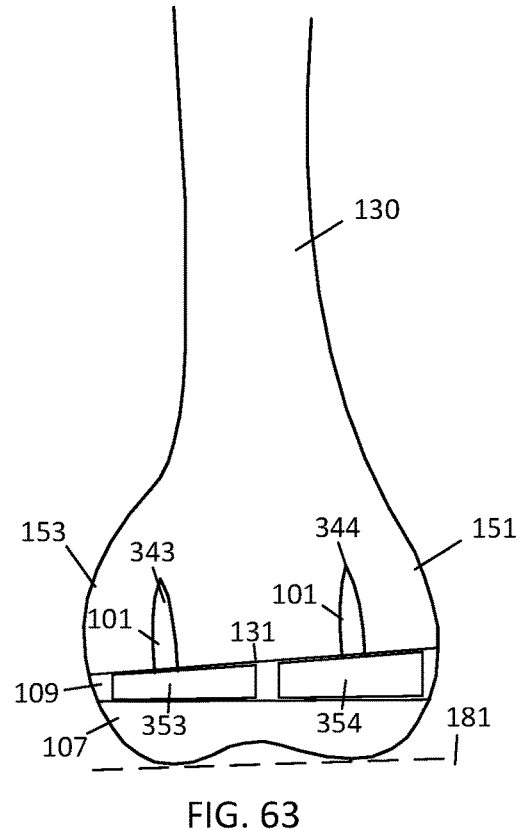
FIG. 63 illustrates an anterior view of a bone with PMMA shim inserts with a final implant.

It can also be possible to correct angular offset errors of the resection bony surfaces. For example, with reference to FIG. 62, hybrid shim inserts 351 and 352 are placed in the resection surface 131 of the bone. The hybrid shim inserts 351 are trialed using a trial implant 108 and the surgeon may determine that the hybrid shim inserts 351 result in a different offset angle 183 than the proper offset line 181. The offset angle of the implant 107 relative to the bone 130 can be corrected by replacing the hybrid shim inserts 351 and 352 with hybrid shim inserts 353 and 354 that have different thicknesses and angles. With reference to FIG. 63, the replacement hybrid shim inserts 353 and 354 can correct the offset position of the final implant 107 to the angle and position that match the correct predetermined offset line 181. Alternatively, if the surgeon needs to angle the implant 107 more towards the medial side, the hybrid shim inserts placed in the MFC 151 can be thinner than the hybrid shim inserts in the LFC 153.

In an embodiment, when a bone is resected, jigs can be used to create specific cuts in the bone resulting in specific shapes and angles of resection bony surfaces. The resectioned bone can be trialed with a trial implant to determine if the resection surfaces are correct based upon range of motion, laxity and stability testing. If the bone is resectioned perfectly and the trial testing is successful, the hybrid shim inserts can be mechanically bonded to the resectioned bone with liquid PMMA cement. However, if there are any errors in the resectioning and the bony surfaces needs to be built up to correctly offset the implant, hybrid shim inserts can be used to make these corrections. In an embodiment, a set of hybrid shim inserts can be manufactured specifically to match the angles and shapes of the implant and bony surfaces. The hybrid shim inserts can be made at various thicknesses and angles to allow a surgeon to make any necessary corrections to properly position the implant during surgery. FIGS. 64-71 illustrate examples of hybrid shim inserts which can be used to make length and angle corrections to the bony surfaces where the implant will be mounted.

Figure 64:
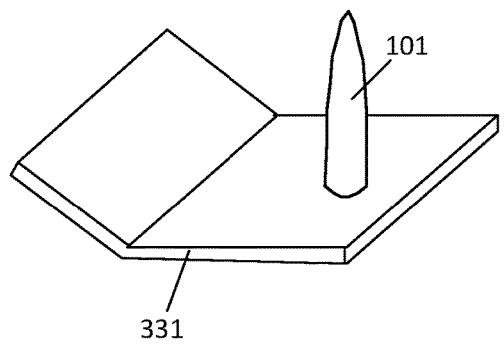
FIGS. 64-71 illustrate perspective views of different embodiments of PMMA shims.
Figure 65:
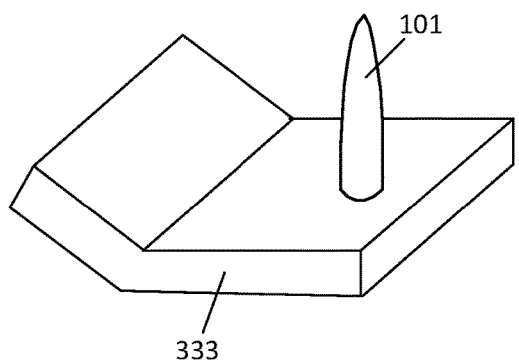
Figure 66:
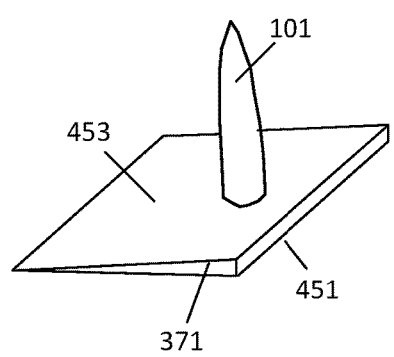
Figure 67:
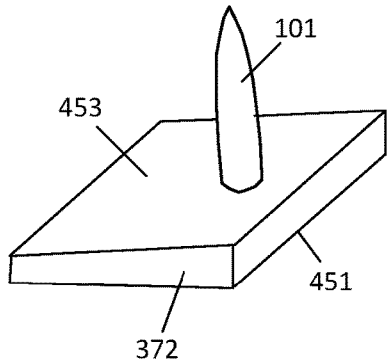
Figure 68:
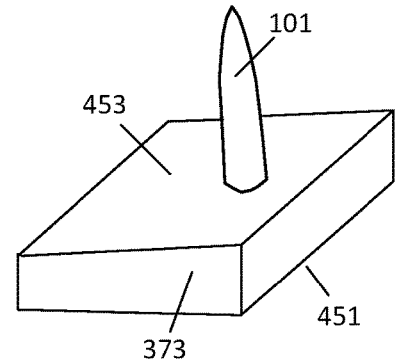

FIGS. 64 and 65 illustrate hybrid shim inserts 331, 333 that can cover multiple resection surfaces. The stem 101 with bone ingrowth and ongrowth surfaces can be inserted into the bony surface and the shim can cover two adjacent resection surfaces. The surgeon may determine that the offset needs to be increased. If a little offset is needed, the thinner PMMA sections 331 of the hybrid shim insert illustrated in FIG. 64 can be used and if a longer offset is needed, the thicker PMMA section shim 333 hybrid shim insert illustrated in FIG. 65 can be used. For example in an embodiment, the trial implant can be tested on the resectioned bone. The stem 101 of the shim 331 can be attached by pressing the stem 101 into the bone. The stem 101 does not have PMMA and the surface features and coatings of the stem 101 promote bone ingrowth and ongrowth over time. Different thickness hybrid shim inserts can be trialed until the proper size PMMA shims are found.

With reference to FIGS. 66-71, embodiments of angled hybrid shim inserts 371, 372, 373 are illustrated. The hybrid shim inserts 371, 372, 373 can each have the same relative angle between the first surface 451 and the second surface 453. However, the angled hybrid shim inserts 371, 372, 373 have different thicknesses. As discussed, a trial implant can be tested on the resection surfaces of the bone and the surgeon can perform a trial assessment of the hybrid shim inserts. If surgeon determines that hybrid shim inserts are needed, the surgeon can select one of the hybrid shim inserts 371, 372, 373. The selected hybrid shim inserts can be trialed and if the hybrid shim insert passes the trial assessment, liquid PMMA cement can be applied to the PMMA portions of the hybrid shim inserts, bone and implant to chemically bond to the PMMA portions of the shim(s) and mechanically bond the implant to the bone. The stem 101 can include a structure material and/or coating that improves bone ingrowth and ongrowth. For example, in an embodiment the stems 101 may be made of titanium or talium which promote bone ingrowth and on growth. The stem 101 can also be structurally configured to have macrostructural fenestrations. In other embodiments, the second sections can be completely covered with ingrowth surfaces or partially covered with ingrowth surfaces.

Figure 69:
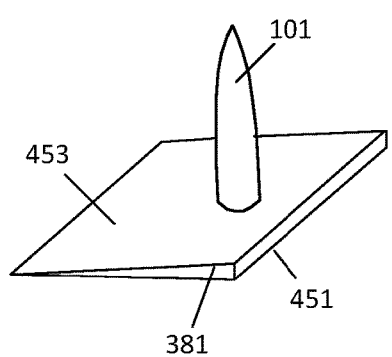
Figure 70:
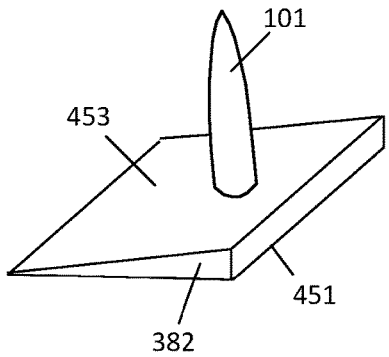
Figure 71:
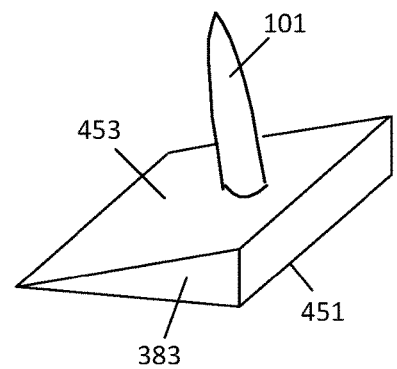

With reference to FIGS. 69-71, embodiments of angled hybrid shim inserts 381, 382, 383 are illustrated. The hybrid shim inserts 381, 382, 383 can each have a different angle between the first surface 451 and the second surface 453. A trial implant can be tested on the resection surfaces of the bone and the surgeon can perform a trial assessment of the shim. If surgeon determines that an angled hybrid shim insert is needed, the surgeon can select one of the hybrid shim inserts 381, 382, 383. The selected hybrid shim insert can be trialed and if the hybrid shim insert passes the trial assessment, liquid PMMA cement can be applied to the PMMA portions of the hybrid shim inserts, bone and implant to chemically bond to the PMMA portions of the shim and mechanically bond the implant to the bone. The stem 101 can include a structure material and/or coating that improves bone ingrowth and ongrowth as described above.

Figure 72:
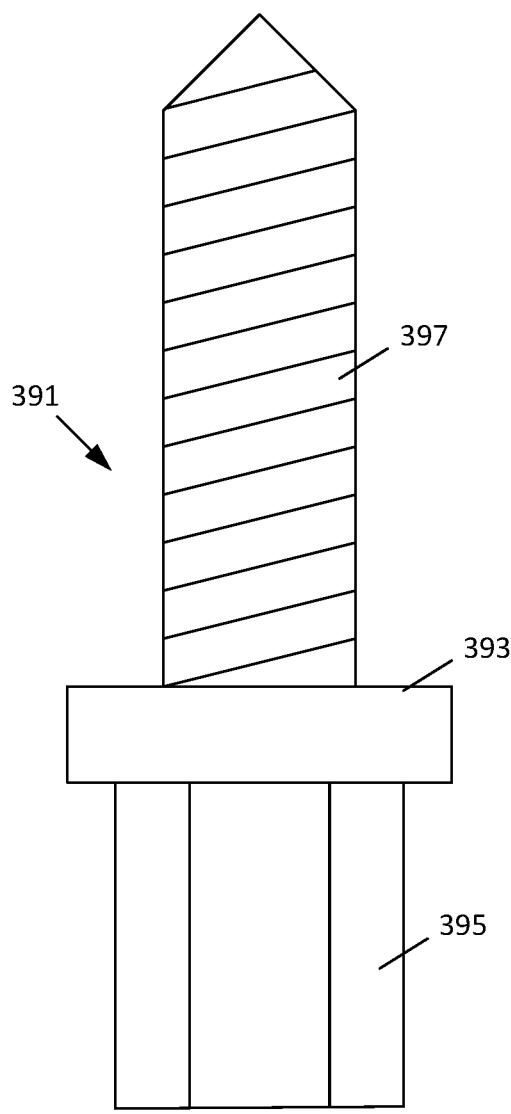
FIG. 72 illustrates a side view of an embodiment of a bone drill.
Figure 73:
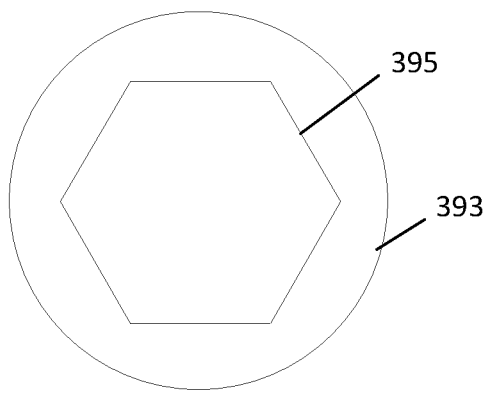
FIG. 73 illustrates a top view of an embodiment of a bone drill.
Figure 74:
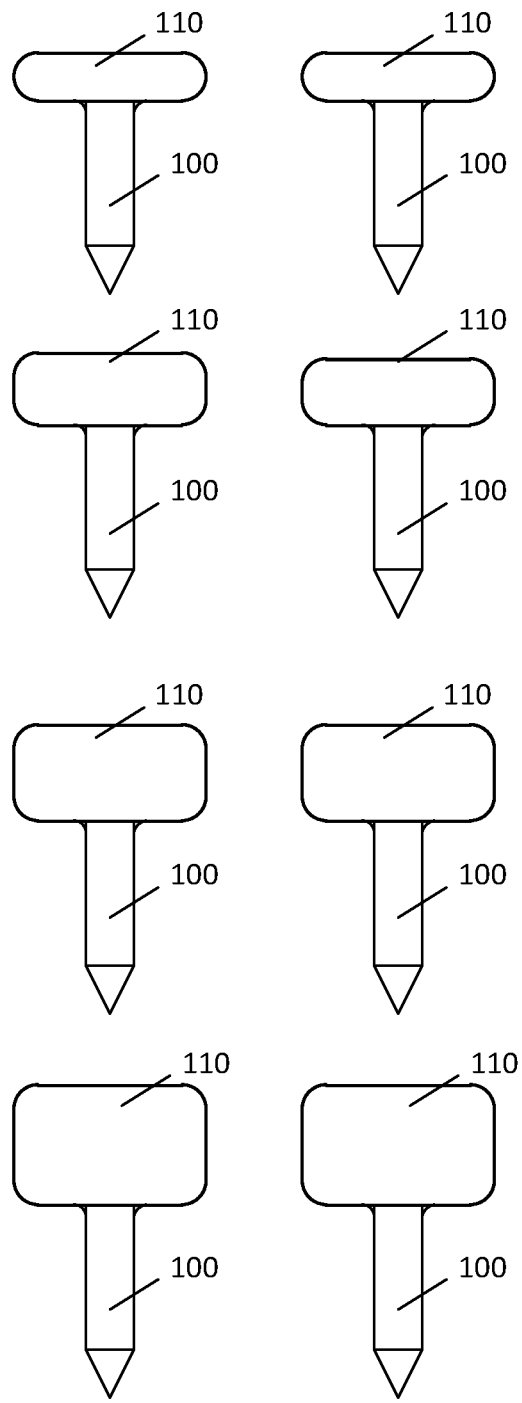
FIG. 74 illustrates a set of PMMA tack inserts used in an augmentation kit.

In different embodiments the described hybrid insert system can be provided to doctors in the form of a PMMA/bone ingrowth hybrid insert kit which can include any combination of components. The kit may also include a stepped drill bit which can be used to form holes for the elongated rod portions of the hybrid inserts. The drill bit can include a sharp cutting portion and a smooth step that has a larger diameter. When a bone is drilled, the sharp cutting portion will form the holes but the drill bit will stop removing bone material when the smooth step edge contacts the outer surface of the bone. The drill bit can produce uniform diameter and depth holes in bones. For example with reference to FIGS. 72 and 73, in an embodiment the stepped bone drill 391 which includes a helical cutting portion 397 and a stop step 393. A drive portion 395 of the bone drill 391 opposite the cutting portion 397 can have a hexagonal cross section which can be attached to a drill mechanism. With reference to FIG. 74, a hybrid insert kit can include a plurality of hybrid tack inserts 100 that can have many different head thicknesses. In an embodiment, the hybrid tack inserts 100 may have different thicknesses which vary by 1 mm increments, such as 1 mm, 2 mm, 3 mm, etc. The hybrid insert kit can provide 2 to 4 hybrid tack inserts per head thickness size. In this illustrated example, the PMMA heads of the hybrid tack inserts can be flat planar meaning that the planes defined by the upper and lower surfaces of the heads can be parallel.

With reference to FIGS. 75-77, in other embodiments the hybrid tack inserts 471 can have a modular design which have a stem 101 with bone ingrowth/ongrowth surfaces and a cap 473 having PMMA outer surfaces. The bone offset or cap thickness of the hybrid tack inserts 471 can be adjusted in thickness by increased by adding PMMA spacer 475 to the top of the PMMA cap 473. In an embodiment, the stem 101 can have surface features such as pores or fenestrations and may also have coatings which promote bone ingrowth or ongrowth without PMMA. The caps 473 and spacers 471 can be have cured PMMA surfaces and include recesses 477 and the cap inserts 471 can include coupling features 479.

If the cap 473 thickness of the hybrid tack insert 471 does not provide a sufficient offset, one or more PMMA spacers 475 can be attached to the top surface of the cap 473. FIG. 75 illustrates the hybrid tack insert 471 and separated spacers 475. The coupling features 479 on the spacers 475 can be placed in the recesses 477 to increase the assembly cap offset. With reference to FIG. 76, two spacers 475 have been attached to the cap 473 of the tack insert 471 with the coupling features 479 inserted into the recesses 477. The cap 473 and the spacers 475 can include concave surfaces which can allow the surgeon to easily grasp the cap 473 and spacers 475 and adjust the offset of the cap 473 and spacers 475. With reference to FIG. 77, the hybrid tack insert 471 with spacers 475 is inserted into the bone 130 and a trial implant 481 is placed against the upper PMMA spacer 475 to perform trial assessment. If the hybrid tack insert 471 with spacers 475 provide the correct implant offset, liquid PMMA can be applied to the hybrid tack insert 471 and spacers 475 assembly and the bone and implant. The liquid PMMA can cure and chemically bond to the PMMA portions of the hybrid inserts 471 and create a mechanical bond between the bone implant and the bone.

In an embodiment with reference to FIG. 78, an insert kit can include a tool 483 having a fork mechanism 485 that can engage the concave surfaces on the outer diameters of the cap and the cap attachments 475. The tool 483 can be used to easily couple or separate the cap attachments 475 as necessary based upon the trialing assessment.

With reference to FIG. 79, an embodiment of a hybrid threaded insert 501 is illustrated. The insert 501 can have a cap 510 made of cured PMMA that can be rotated with a tool to drive the threaded stem 503 into a bone. The threaded stem 503 can be made of a material with surface features and/or coating that improves bone ingrowth and does not include any exposed PMMA surfaces. The threaded stem 503 can also have visual markings which can allow the surgeon to know the offset of the hybrid insert 501. In this example, the visual markings 505 on the threaded stem 501 are a plurality of lines which can be spaced at uniform distances. With reference to FIG. 80, the threaded insert 501 has been screwed into a bone to a depth that matches a first offset line 511. The surgeon can place a trial implant against the upper surface of the cap and perform trialing. If there is an error, the surgeon can make adjustments to the offset of the hybrid insert 501 by rotating in one direction to drive the threaded insert 501 further into the bone or in the opposite direction to move the insert 501 further out of the bone. With reference to FIG. 81, the surgeon may rotate the hybrid threaded insert 501 so that the outer surface of the bone is on the second offset line 512 and the described trialing process can be repeated. Once the proper hybrid insert 501 position is found, liquid PMMA cement can be applied to the insert, the bone and the implant. The liquid PMMA can cure forming a chemical bond with the PMMA cap 510 of the hybrid insert 501 and forming a mechanical bond between the bone and the implant. The cured liquid PMMA will also prevent the hybrid threaded insert 501 from rotating which will effectively lock the hybrid threaded insert 501 in the desired offset position. The liquid PMMA may not flow between the threaded portion of the stem and the inner diameter of the bone hole so that the bone ingrowth and ongrowth can occur.

Figure 82:
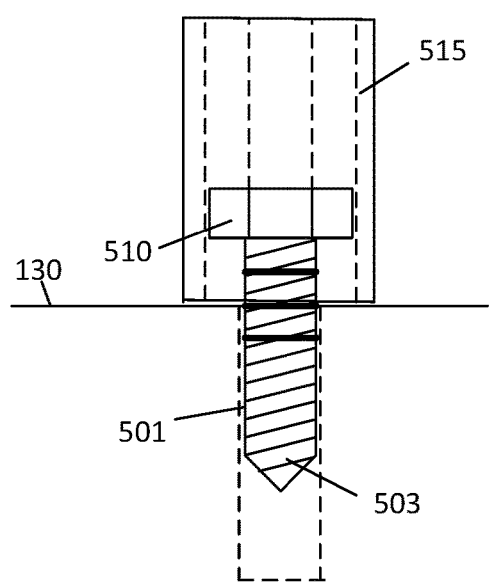
FIGS. 82-83 illustrate side views of an embodiment of a threaded PMMA insert rotated by an insertion tool in a bone.
Figure 83:
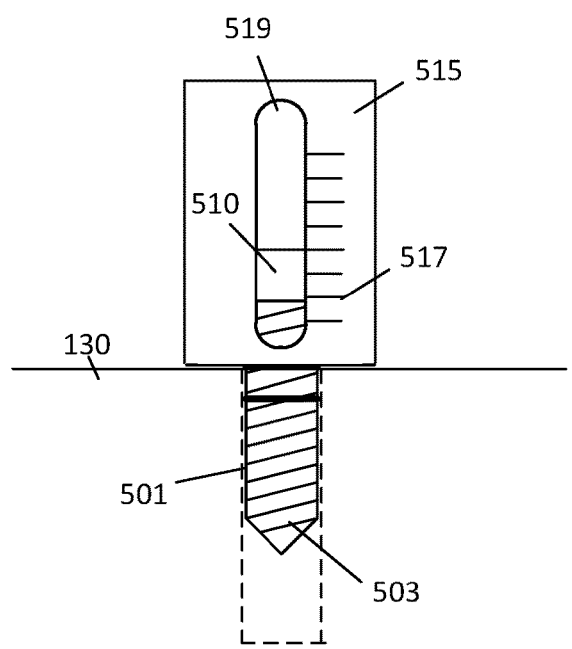

With reference to FIG. 82 a side view of a hybrid insert 501 with the cap 510 in a rotational tool 515 is illustrated. In this example, the tool 515 may have a hexagonally shaped inner surface which fits over the hexagonal cap 510. The tool 515 can be rotated to rotate the hybrid insert 501 and drive it into the bone 130. With reference to FIG. 83, a side view of the rotational tool 515 is illustrated with a side window 519 and an offset visual scale 517. As the tool 515 rotates, the surgeon can monitor the position of the cap 510 and determine the offset of the cap 510 from the surface of the bone 130. Once the hybrid insert 501 is rotated to the desired offset, the tool 515 can be removed and a trial implant can be placed on the cap 510 of the hybrid insert 501. Trialing can be performed on the hybrid insert 501 and adjustments to the hybrid insert 501 can be made. Once the hybrid insert 501 is rotated to the desired offset, liquid PMMA cement can be applied to exposed portions of the hybrid insert 501 and bone to prevent further rotation of the threaded hybrid insert 501.

Figure 84:
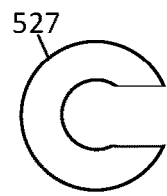
FIG. 84 illustrates a top view of a PMMA spacer.
Figure 85:
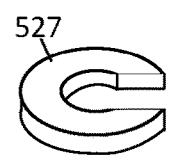
FIG. 85 illustrates a perspective view of a PMMA spacer.
Figure 86:
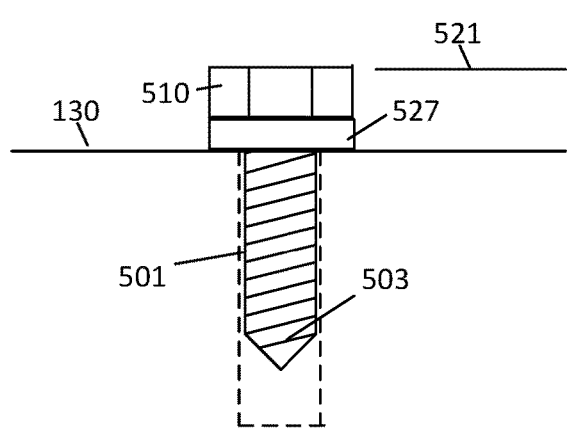
FIG. 86 illustrates a side view of an embodiment of a threaded PMMA insert and a PMMA spacer.
Figure 87:
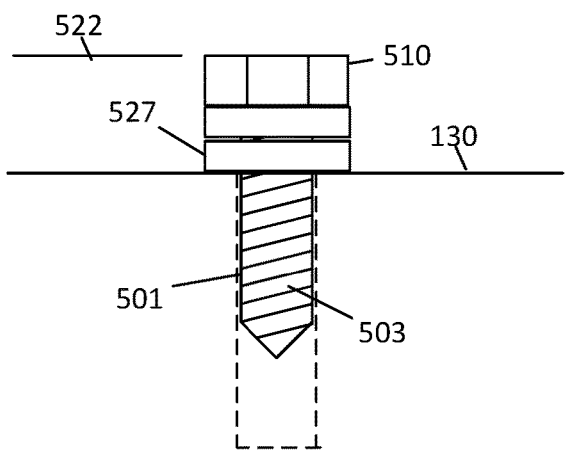
FIG. 87 illustrates a side view of an embodiment of a threaded PMMA insert and multiple PMMA spacers.

With reference to FIG. 84 a top view of a PMMA spacer 527 and in FIG. 85 a perspective view of a PMMA spacer 527 are illustrated. The spacers 527 can have a "C" shaped structure that can fit around the stem portion 501 of the hybrid threaded insert 527 and have uniform thicknesses. The surgeon can have a plurality of the spacers 527 available. With reference to FIG. 86, if the offset of the hybrid insert 527 needs to be increased, the hybrid insert 527 can be rotated to move the cap 510 away from the bone 130. A spacer 527 can then be placed around the stem 503 and between the bone 130 and the cap 510. The hybrid insert 501 can then be rotated to compress the spacer between the cap 510 and the bone 130. The offset 521 will be equal to the thickness of the spacer 527 and the cap 510 thickness. Trialing can be performed until the proper offset of the hybrid insert 501 is determined. With reference to FIG. 87, if additional offset is needed, an additional spacer(s) 527 can be used. The hybrid insert 501 can be rotated to move the cap 510 to fit another spacer 527 on the stem 503. The offset 522 will be equal to the thickness of two spacers 527 and the cap 510 thickness. Once the proper offset is found, the tool 515 can be removed, liquid PMMA can be applied to the bone 130, the spacers 527, the exposed portions of the hybrid insert 510 and the implant. The liquid PMMA can cure to form a chemical bond with the spacers 527 and the exposed portions of the hybrid insert 510. The cured PMMA portions of the hybrid insert 510 will also form a mechanical bond between the implant (not shown) and the bone 130. As discussed, the stem 501 can include a structure material and/or coating that improves bone ingrowth and ongrowth and not include any PMMA as described above.

Figure 88:
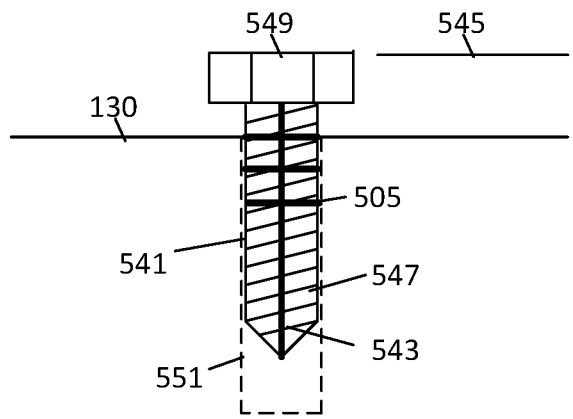
FIG. 88 illustrates a side view of a threaded and expandable PMMA insert in a bone.
Figure 89:
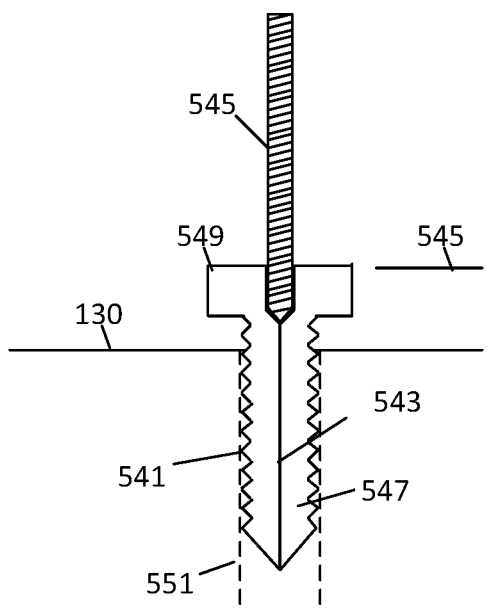
FIGS. 89-90 illustrate side views of a threaded and expandable PMMA insert in a bone with an expansion screw.
Figure 90:
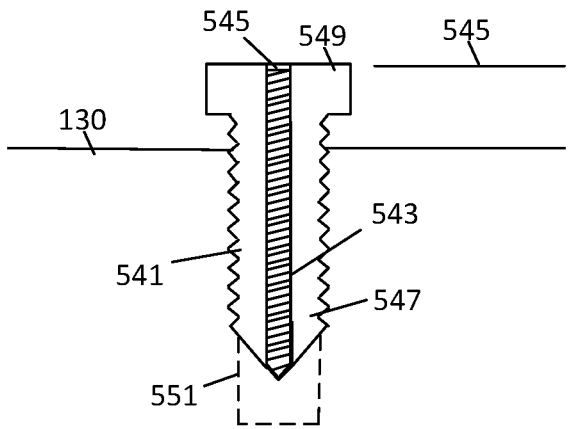

Another embodiment of a threaded hybrid insert 541 is illustrated in FIGS. 88-90. With reference to FIG. 88 a stem of the threaded hybrid insert 541 can be threaded into a hole 551 in a bone 130. The stem 501 can be made of a material and have features and coatings that promote bone ingrowth and ongrowth. The stem 501 does not include any PMMA surfaces. In an embodiment, the PMMA cap 549 can have a hexagonal shape which can be rotated with a wrench or other tool. The stem 547 can include a slot 543 which can allow the stem to expand outward. The threaded insert 541 can have offset markings 505. The hybrid insert 541 can be rotated to a desired offset position and in this example, the first offset marking 505 can be aligned with the outer surface of the bone 130. With reference to FIG. 89, when the hybrid insert 541 is adjusted to the desired offset position, a expansion screw 545 can be threaded into the hybrid insert 541. The expansion screw 545 can have an internal hexagonal driver surface that can be rotated with a hex driver. With reference to FIG. 90, the expansion screw 545 can be threaded into the hybrid insert 541 and the stem 547 can be split at the slot 543 and pressed into the inner diameter surfaces of the hole 551.

Figure 91:
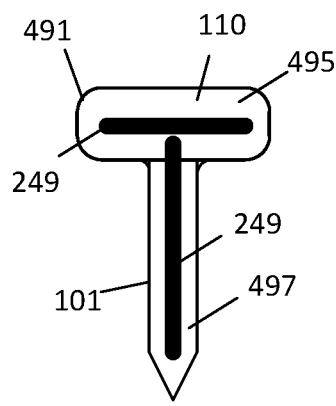
FIGS. 91-93 illustrate side views of embodiments of modular composite PMMA tack inserts.
Figure 92:
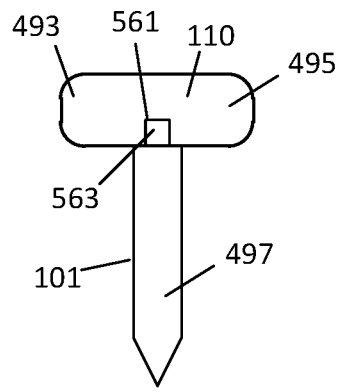
Figure 93:
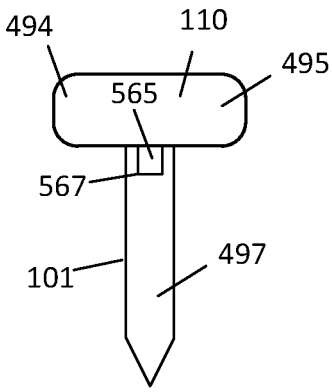

In other embodiments, the hybrid tack inserts can have modular constructions. For example, in an embodiment the hybrid tack inserts can include bone ingrowth/ongrowth feature and coating stems and PMMA caps which can be assembled to create the hybrid tack inserts. With reference to FIGS. 91-93, examples of hybrid tack inserts that are modular designs fabricated with cured PMMA caps are illustrated. With reference to FIG. 91, a hybrid tack insert 491 can include a substrate 249 which can be an elongated rod made of a metal or non-PMMA polymer within a stem 101 and a bone ingrowth/ongrowth 497 outer material. The cap 110 can be made with a PMMA material 495 covering the substrate 249. The proximal end of the substrate 249 in the stem 101 can be pressed into a hole in the cap 110 and the stem 101 can be bonded to the cap 110 with liquid PMMA cement or any other suitable structural coupling. It can be more cost efficient to fabricate separate PMMA caps 110 and non-PMMA stems 101 and then assembly these components to create the hybrid tack inserts 491. These assembly modular hybrid inserts 491 can then be used as described above.

In yet another embodiment as shown in FIG. 92, a hybrid modular tack insert 493 can include the cap 110 component made of PMMA 495 and a stem 101 component made of a bone ingrowth material 497. The cap 110 can have a hole 561 and the stem 101 can have a corresponding feature 563 that can be mechanically connected to the hole 561. A liquid PMMA cement can be used to chemically bond the stem 101 to the hole in the lower surface of the cap 110. When the hybrid tack insert 493 is pressed into the bone and liquid PMMA cement is applied, the cap 110 will be chemically bonded to the cured PMMA cement.

In FIG. 93, a hybrid tack insert 494 can also include the cap 110 component made of PMMA 495 and a stem 101 component made of a bone ingrowth/ongrowth material 497. The cap 110 can include a feature 565 on a lower surface which is chemically and or mechanically bonded to a hole 567 in the upper surface of the stem 101 with liquid PMMA cement. Again, when the hybrid tack insert 494 is pressed into the bone and liquid PMMA cement is applied, the cap 110 will be chemically bonded to liquid PMMA as it cures as described above.

As discussed, the inventive hybrid insert apparatus and method can be used for various types of bone implants such as total knee arthroplasty. In an embodiment, the hybrid insert can be applied to bond the implant to the bone with the following surgical approach technique. An incision is made, the joint is exposed through one of several standard approaches through medial retinaculum and proximal extension. The surgeon can perform soft tissue releases and remove boney osteophytes. The surgeon then can prepare the patella, femur and tibia. The order of preparation of components can vary with the preference of the surgeon. In one common technique, the patella can be exposed and the thickness of the patella can be measured. The patella can then be cut and the knee can be sized for the implant. A drill guide can be applied to the patella and the patella can be prepared for the patella implant. A trial implant can be applied to the patella to check the fit of the final implant.

Figure 94:
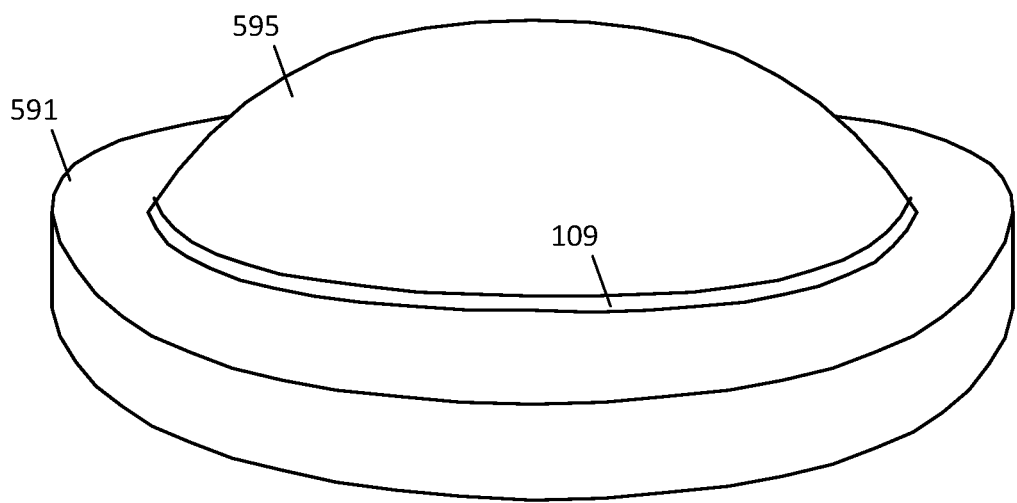
FIG. 94 illustrates a perspective view of a patella bone with a patella implant.
Figure 95:
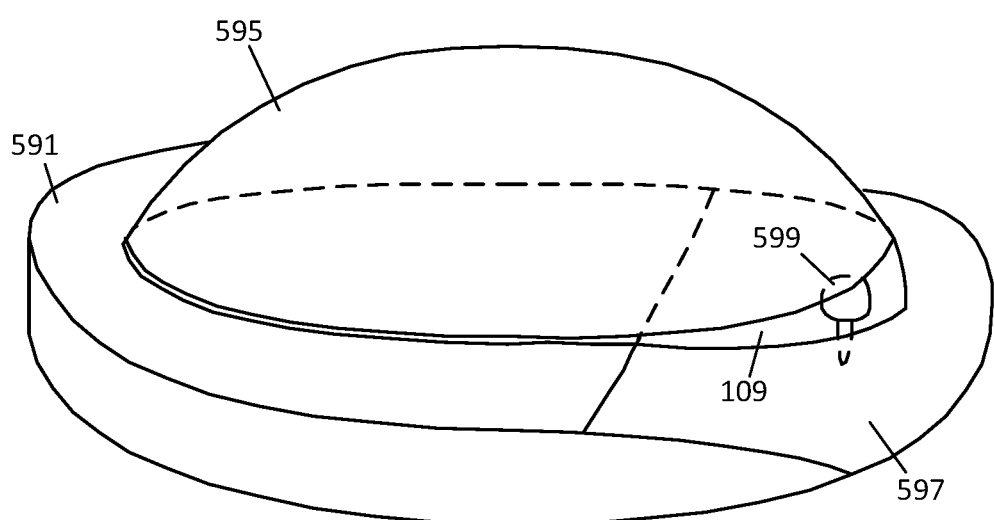
FIG. 95 illustrates a perspective view of a patella bone with a tack insert and a patella implant.
Figure 96:
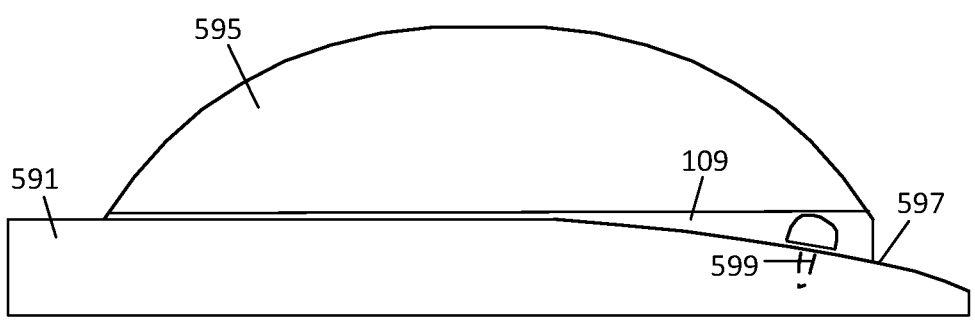
FIG. 96 illustrates a side view of a patella bone with a tack insert and a patella implant.

With reference to FIG. 94, a perspective view of a patella bone 591 is illustrated with a patella implant 595 secured to the patella bone 591 with liquid PMMA cement 109 is illustrated. As discussed, the patella bone 591 can be cut creating a planar resection surface. The patella implant 595 can have a convex outer surface and a planar lower surface that is secured to the resection surface of the patella bone 591. A perspective view of a patella bone 591, insert 599 and a patella implant 595 are illustrated with reference to FIG. 95. With reference to FIG. 96, a side view of the patella bone 591, insert 599 and a patella implant 595 are illustrated. In some patients, the patella bone 591 can have a damaged area 597 that needs to be built up and the resection of the patella bone 591 may not result in a planar surface upon which the patella implant 595 can be secured. In these situations, the described hybrid inserts can be used to properly secure the patella implant 595 to the patella bone 591. In the illustrated embodiment, a hybrid insert 599 can be placed in the damaged area 597 with the stem of the hybrid insert 599 which can have bone ingrowth features and coatings but does not include PMMA is pressed into the damaged area 597 of the patella bone 591 and a PMMA cap of the hybrid insert 599 in physical contact with the damaged area 597 and the patella implant 599. The surgeon can perform trialing on the hybrid patella insert 599 with a patella trial implant as described. When the proper insert 599 is found, liquid PMMA cement 109 can be applied to the patella implant 595, the patella bone 591 and the exposed portions of the hybrid insert 599 but not the interface between the stem and the bone so that bone ingrowth can occur. The patella implant 595 can be placed on the patella bone 591 and the hybrid insert 599 which can provide physical support for the bone implant 595. The liquid PMMA cement 109 can cure to chemically bond to the exposed PMMA portions of the hybrid insert 599 and create a mechanical bond between the patella implant 595 and the patella bone 591.

The trial implant is then removed and the femur is exposed, usually with two z type retractors. The distal femur is then drilled with an entry hole. An intramedullary rod and cutting guide can be applied to the distal femur. The guide can be adjusted for proper varus/valgus angle and to provide the proper amount of femoral bone resection. The cutting guide is then secured to the femur, usually with drill pins. The intramedullary rod and alignment jig are removed before cutting distal femur with oscillating bone saw. The femur can then be measured to determine the best bone implant size. The surgeon can then use the trial implant to determine the proper rotation of implant. The femur can be drilled to establish the joint rotation. A cutting guide can be used for making bone cuts with a bone saw. The cutting jig and bone fragments can then be removed from the surgical area.

The surgeon can then expose the tibia which can be done with medial, lateral and posterior retractors. The surgeon can then debride the meniscus and soft tissues. An extramedullary cutting guide can be applied to the anterior tibia. The guide can then be properly adjusted for: 1) amount of resection 2) posterior slope and 3) varus/valgus angle. The cutting guide can be secured to the tibia with pins. The tibia can be cut with an oscillating saw using the cutting guide. The cutting guide and bone fragments can then be removed. The surgeon can assess flexion and extension gaps with spacer blocks and determine if the joint is ready for a trial assessment. If the cuts appear correct, the surgeon can then apply and position trial components. Femoral component is applied to the femur followed by the tibial component, a tibial plastic spacer tray and the patellar component.

With the trial implants in place, the surgeon can perform a trial assessment. Trial femoral, tibial and patellar implants can be tested to assess 1) tightness in extension and flexion and 2) medial and lateral soft tissue tension (looseness or tightness) throughout flexion and extension. The surgeon can assess the knee's range of motion and the stability of the knee throughout the range of motion. The tracking of the patella can also be assessed.

If range of motion demonstrates excess tightness or laxity, or if the knee is determined not to be adequately stable in any plane or any position, soft tissue balancing, recutting of bone or resizing of implants can be performed by the surgeon until proper range of motion and stability is achieved.

If the surgeon determines that augmentation of the bone is required or additional offset from the boney resected cuts, the surgeon can choose to use the hybrid insert(s) for correction. The hybrid inserts can be adjusted based upon the errors detected during trialing. With reference to Table 1 below, a listing of possible trial assessment imbalances are listed and the corresponding procedures for correcting the assessment defects.

TABLE 1

| Trial Assessment Imbalance | Possible Corrective Actions |
|---|---|
| Tight in extension | resecting more of the femur |
| | resecting the tibia with less slope |
| Tight in flexion only | Add tibial slope |
| | Reduce size of femoral component |
| Tight in flexion and Extension | Resect more tibia |
| Loose in Extension only | Recut tibia for more slope and add thickness of plastic insert |
| | Move Femoral Component distally with inserts |
| Loose in flexion only | Increase size of femoral component (support post surface with insert) |
| | Add thicker plastic insert, and resect more femur |
| Loose in Flexion and Extension | Use thicker plastic tibial insert. |
| Angular correction | Recut tibia |
| | Recut femur (cumbersome) |
| Excessive laxity medially | Tibia- More valgus cut and thicker poly with lateral release |
| | Make angular correction of femur with buildup using inserts |
| Excessive laxity laterally | Tibia- medial release, varus recut, thicker poly |
| | Femur- lateral distal buildup with inserts |

Choice of implants and proper preparation for placing final components is achieved when the knee demonstrates sufficient stability to varus and valgus stress throughout range of motion and the knee can move to full extension and full flexion, with good overall alignment of the limb.

The trial implant and any other trial devices can be removed. If hybrid inserts have been placed, the hybrid inserts can remain in place when the actual implant is bonded to the bone. The surgeon can irrigate the knee and remove soft tissue debris. At this stage, final preparation of the tibia is performed with drills and punches to set rotation and prepare for the stemmed component.

With the trialing complete, bone implants can be bonded to the tibia and/or femur. To bond the tibia implant, the tibia is exposed and the liquid PMMA cement is mixed. Liquid PMMA cement is applied and or pressurized to the tibial surface. The surgeon can impact the final tibial implant in place on the tibia, liquid PMMA and hybrid inserts. Once the final tibial implant is positioned, excess extruded PMMA cement is removed circumferentially about tibia and implant.

A similar process is used for bonding the femur implant. The bony surfaces of the femur are exposed. Pressurized liquid PMMA cement can be applied to the bony surfaces of the femur. The surgeon can then impact the final femoral implant in place on the femur, liquid PMMA and hybrid inserts. With the femoral implant properly positioned, the excess cement is circumferentially removed from the femur and implant. A tibial spacer can be placed and secured to the tibial component.

The patella can be exposed and liquid PMMA cement can be applied to the exposed patella. The final patellar implant component can be placed on the patella and the implant can be clamped to the patella. The excess cement can then be removed from the patella and patella implant.

After the liquid PMMA cement cures, the knee can be irrigated. The soft tissue around the knee can be closed and the skin can be closed. A dressing can be applied to the closed wound.

In the setting of revision total joint surgery, the surgeon can encounter deficiencies of any boney surface. The patella can be deficient and can provide only a shell of bone for fixation. Frequently, the surgeon is not able to cement a new patellar implant to the remaining bone. In the presence of deficiency, the surgeon can drill the patella and place one or more inserts that will support the patellar implant. The hybrid inserts are placed and secured to the patella. Liquid PMMA is applied to the undersurface of the patella and implant is applied to the cement, exposed PMMA surfaces of the hybrid insert and patella. Excess cement is removed that is outside of the interface between the implant and bone. Implant is held in position until the PMMA cement had cured.

In revision total joint arthroplasty of joints other than the knee, there is frequently need to create offset or separation between bone and implant while cementing. In acetabular revision of the hip, in situations when a cup remains will ingrown to the acetabulum but no liner is available for the cup shell, surgeons can cement a polyethylene liner into the cup. It is commonly difficulty to accurately control the offset of the plastic liner from the metal shell. A large percentage of cups contain screw holes in the dome of the cup. For these cups, the surgeon can place inserts into the holes that create offset. The surgeon is then able to apply liquid cement and place a standard liner into the acetabular cup while maintaining offset to establish an adequate cement mantle. The surgeon also has the option of applying inserts or rods into a revision acetabulum and then cementing the acetabular component. The presence of inserts or rods can increase the strength of the bone cement interface and assist in accurate placement of the cup.

In the setting of revision total joint arthroplasty, it is common to use porous metal augments to fill large bone deficiencies. These can be used commonly in the acetabulum, the tibia or the femur. Standard technique calls for the surgeon to apply cement at the interface of the augment and the arthroplasty implant. The cement is placed to avoid mechanical wear of metal abrading metal surfaces. In this setting the surgeon can drill the porous metal augment and apply a hybrid insert or inserts to establish accurate separation of the two metal components. The hybrid insert can also provide improved mechanical loading between the two components by allowing pressure to be applied across the hybrid insert while the liquid cement cures. In shoulder arthroplasty, deficiencies of the glenoid bone stock can affect placement of a glenoid component. The described hybrid inserts can be used to offset the glenoid component relative to the glenoid bone.

In different embodiments, the hybrid inserts can have various configurations. For example, in an embodiment, an insert can provide an offset between a bone and an implant. The hybrid insert can include an elongated stem made of a material such as titanium or tantalum and possibly coatings that has surface features that promote bone ingrowth/ongrowth. The hybrid insert can also include a cap made of the cured polymethyl methacrylate (PMMA) material in direct physical contact with the elongated stem wherein a distal surface of the cap is substantially perpendicular to the axis of the elongated stem. In some embodiments of the hybrid inserts can further comprise fenestrations formed in the PMMA cap. The hybrid inserts can also have grooves formed in the elongated stem or the cap. The stem of the hybrid inserts can further comprise helical threads formed on an outer surface of the elongated stem and the cap includes drive surfaces which can be coupled to a rotational insertion tool such as a wrench, screw driver or any other driver tool.

Embodiments of the hybrid inserts can comprise a portion made of or covered with cured PMMA and a stem made of a material that promotes bone ingrowth and/or ongrowth. In some embodiments the hybrid inserts can have a metal substrate such as titanium or tantalum with just the metal cap substrate encapsulated within the PMMA material. In some embodiments, the hybrid insert can include a polymer substrate. The ingrowth and/or ongrowth surface is on the outer surface of the stem which can have recessed pores or fenestrations which can allow the bone to grow into the surrounding bone. In an embodiment, the ingrowth groove surfaces in the stem can be 40-800 microns in width and depth.

Figure 103:
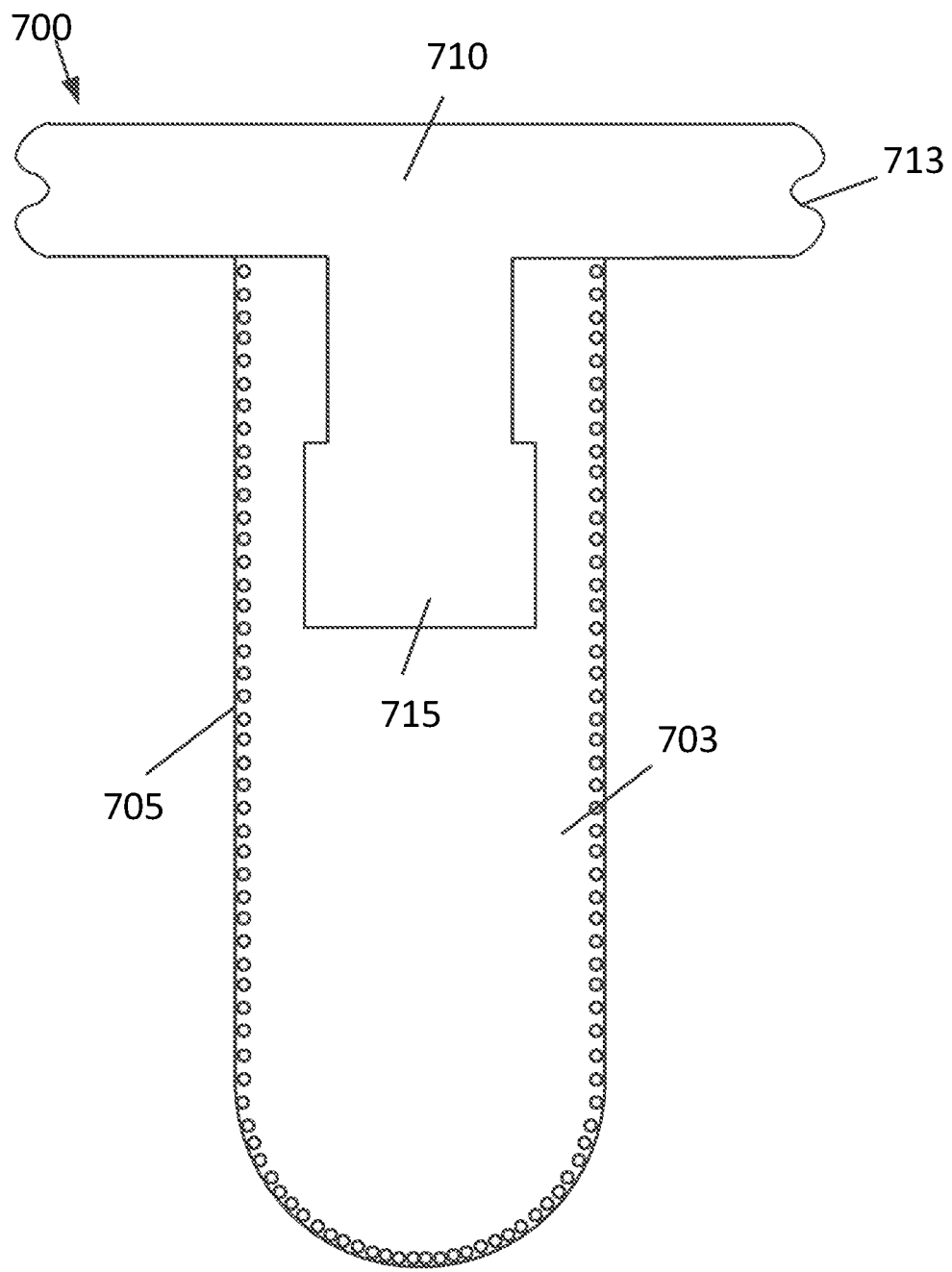
FIGS. 103-109 illustrate side views of embodiments of different hybrid inserts.

With reference to FIG. 103, an example of a hybrid insert 700 is illustrated which includes stem 703 having an ingrowth surface 705 and a cap 710 which is physically attached to the stem 703. The ingrowth surface 705 can be grooves, trabeculations or recessed holes, which are 40-800 microns in width and depth which promote bone ingrowth. In different embodiments, the ingrowth surfaces 705 can be formed by various different surface processing methods including, cutting, grit blasting, machining or any other suitable fabrication method on the stem 703 material which can be titanium, tantalum or any surface or material that will promote osteointegration. The cap 710 is made of a different material which promotes bonding to PMMA cement. When the hybrid insert 700 is used with a bone implant, the stem 703 can be inserted into the bone and over time the bone will grow into the ingrowth surfaces 705 which increases the strength of the bond between the bone and the hybrid insert 700. The cap 710 can be made of cured PMMA. After the hybrid insert 700 is placed in the bone, liquid PMMA cement is placed over the cap 710 and the bone and the implant is placed over the bone and cap 710. The cap 710 can provide a bonding surface for the liquid PMMA cement that can be rigidly secured to the bone.

In an embodiment, the stem 703 can be placed in a mold so that the liquid PMMA can be cured to form a cured PMMA cap 710 on the hybrid insert 700. The liquid PMMA can fill the interior volume 715 at the top of the stem 703 and when the liquid PMMA cures the cap 710 will be rigidly bonded to the stem 703. In an embodiment, the internal hollow interior volume 715 can have physical features, which can prevent the cured PMMA cap 710 from being removed from the stem 703. In the illustrated embodiment, the diameter of the hollow interior volume 715 adjacent to the cap 710 can be narrower than the diameter of the hollow portion deeper within the stem portion. During the PMMA molding process, the cured PMMA hardens can bond to the internal surfaces of the hollow interior volume 715 and the wider cross section prevents the cured PMMA from being removed.

The cap 710 can have a surface feature that allows the hybrid insert 700 to be extracted if the hybrid insert 700 needs to be removed from the bone. In this embodiment, the outer perimeter of the cap 710 can have a concave surface 713 which can function as an extraction surface using a fork tool such as the one illustrated in FIG. 78.

Figure 104:
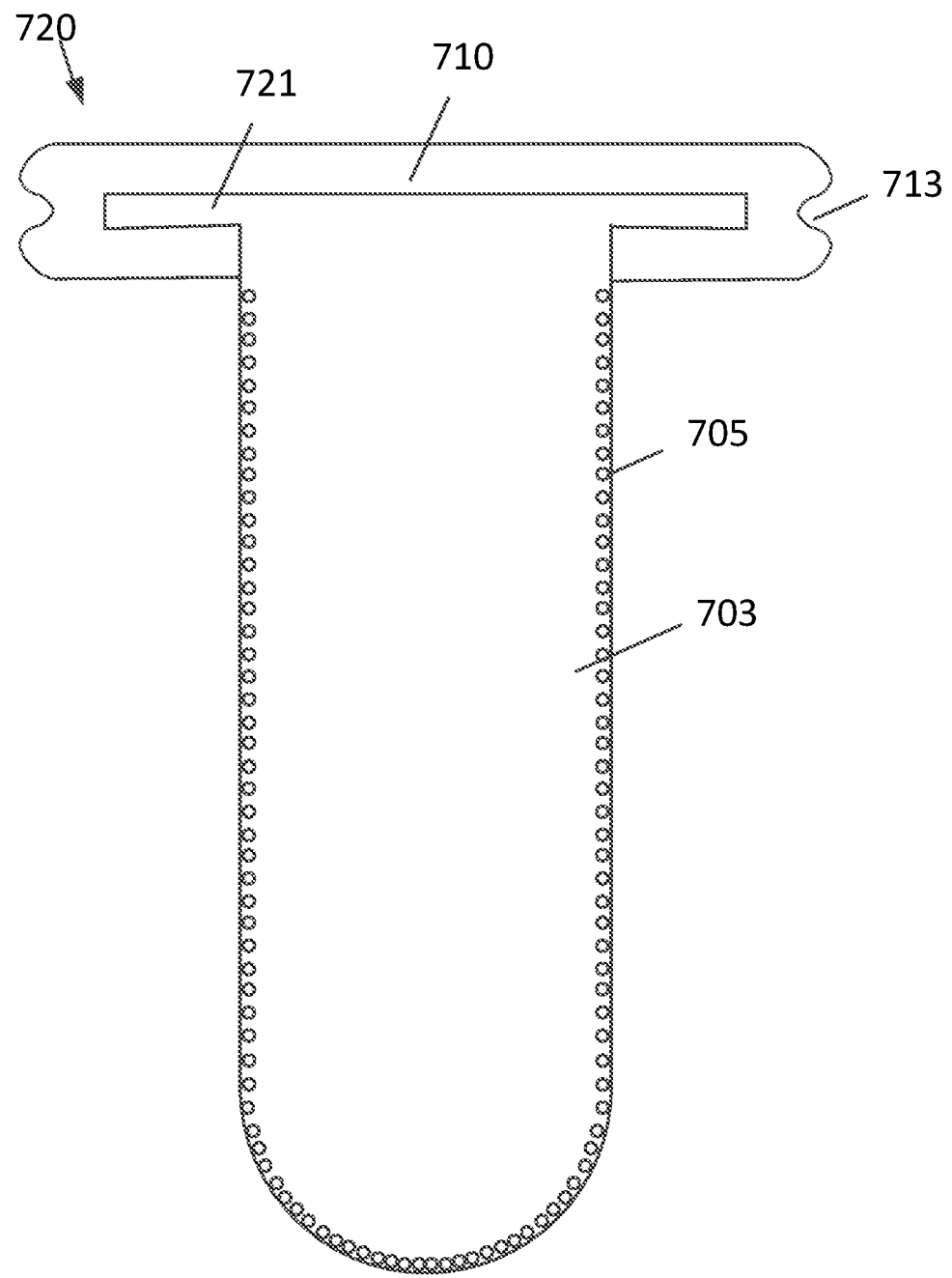

FIG. 104 illustrates another embodiment of a hybrid insert 720 the metal substrate material in the stem 703 can extend into the cap 710 portion of the hybrid tack insert 720. In this embodiment, a flange 721 is formed on an upper portion of the stem 703. The flange 721 can be placed in a mold and the PMMA cap 710 can be formed around the flange 721. The hybrid insert 720 can have the same ingrowth surface 705 and concave surface 713 in the outer perimeter of the cap 710 as described above with reference to FIG. 103.

Figure 105:
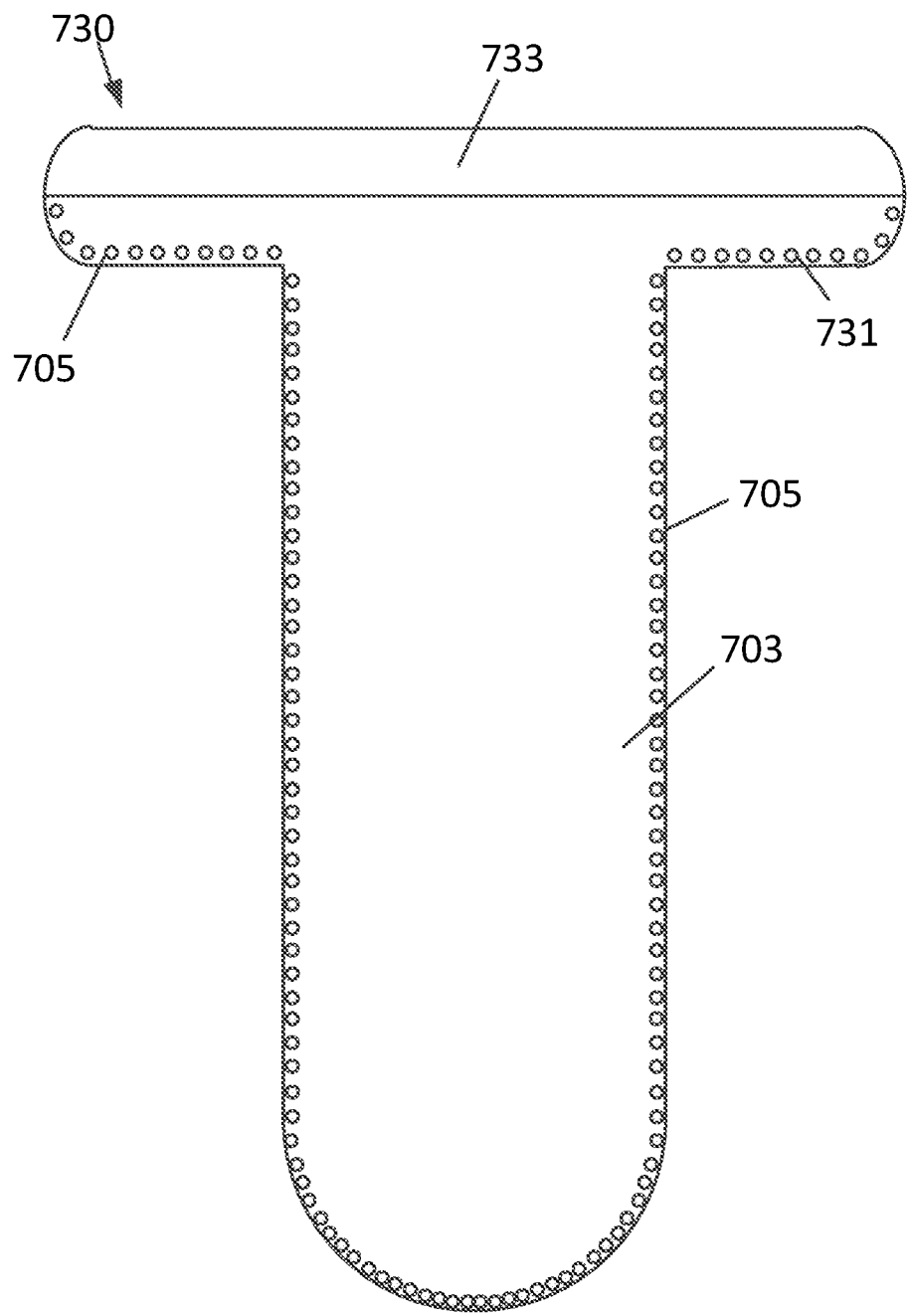

FIG. 105 illustrates an embodiment of a hybrid insert 730 that includes a stem 703 and a lower portion of the cap 731 that are formed from a metal substrate such as titanium or tantalum. An upper portion of the cap 733 can be made of cured PMMA. In an embodiment, the lower portion of the cap 731 can be placed in a mold and liquid PMMA can be placed in the mold over the lower portion of the cap 731 and allowed to cure. The hybrid insert 720 can have the same ingrowth surface 705 on the outer surfaces of the stem 703 and the bottom surfaces of the lower portion of the cap 731 as described above with reference to FIG. 103. Because the bottom surfaces of the lower portion of the cap 731 are in contact with the bone, ingrowth by the bone can occur which can further strengthen the bond of the hybrid insert 730 to the bone.

Figure 106:
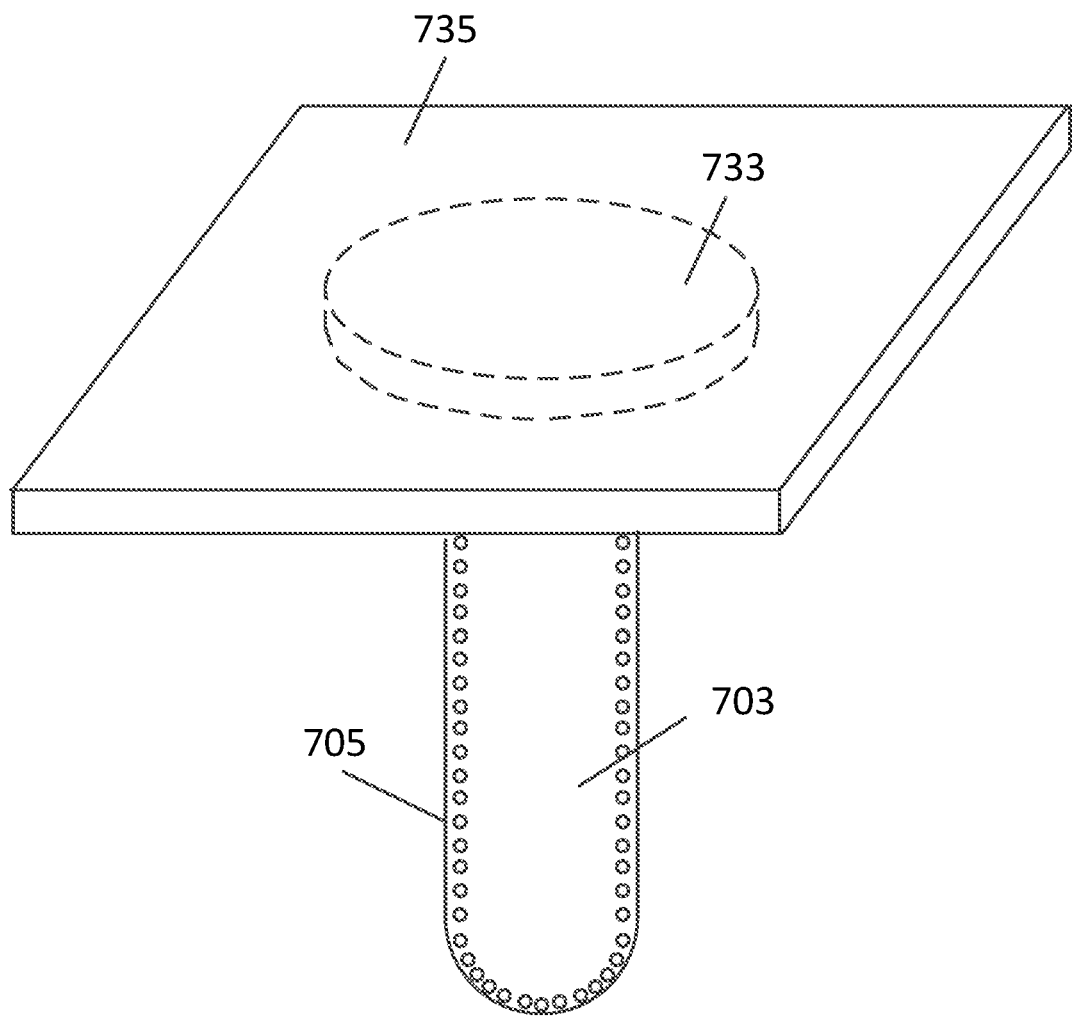

A second surface of the cap opposite the first surface is adapted for contact with a bone implant as discussed in the embodiments of the hybrid tack insert described above. In some embodiments the upper and lower surfaces of the cap can be planar and parallel. However, in other embodiments, the upper and lower surfaces of the cap, can be non-parallel and form an acute angle. The upper surface of the cap can be made from a sheet of cured PMMA, which can be adhesively bonded to the upper surface of the metal substrate. With reference to FIG. 106, a sheet of cured PMMA sheet material 735 can be adhesively bonded to the top cap portion of the metal substrate. The PMMA cured sheet material 735 can then be cut to a circular shape that matches the top cap portion of the metal substrate to form the hybrid insert 730 shown in FIG. 105. A bottom surface of the cap 710 can be adjacent to the surface of a bone 735 and the upper surface of the cured PMMA cap 733 can provide a rigid surface that the liquid PMMA can bond to. The upper surface of the cured PMMA cap 733 can also provide a support surface for positioning a bone implant. The stem 703 is inserted into the bone which can grow into the ingrowth surfaces 705 on the stem 703 and lower surface of the lower portion of the cap.

Figure 107:
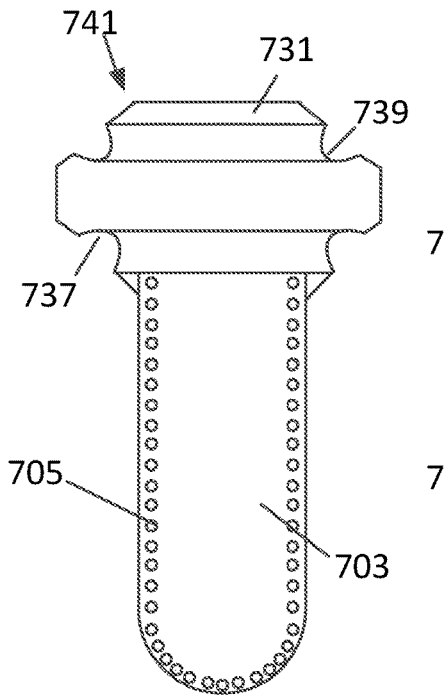
Figure 108:
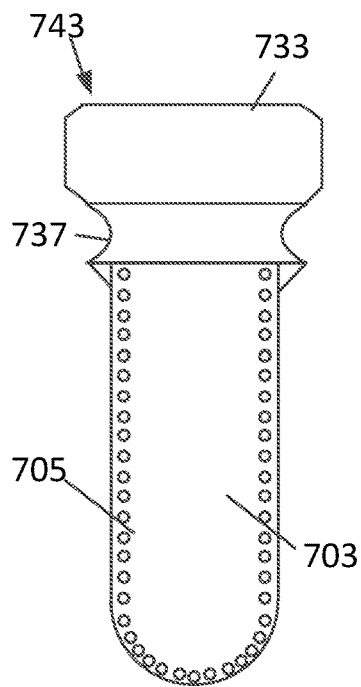
Figure 109:
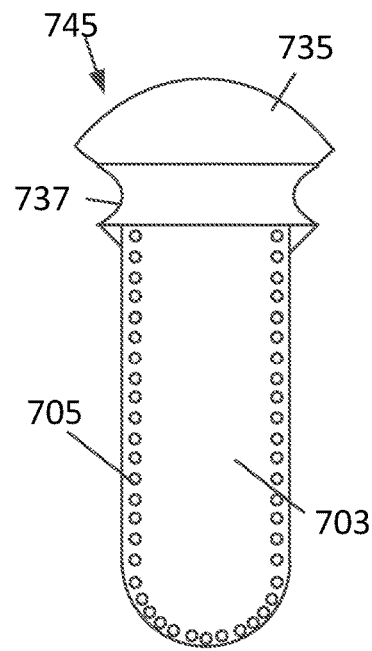

FIGS. 107-109 illustrate other embodiments of hybrid inserts that have the same stem 703 with ingrowth surfaces 705 but different cured PMMA caps. With reference to FIG. 107, an embodiment of a hybrid insert 741 is that has a cap 731 with lower recesses 737 and upper recesses 739 which can be used to extract the hybrid insert 741 from the bone. The cap 731 has a flat upper surface and vertical side surfaces, which can be used to position the implant on the bone. With reference to FIG. 108, an embodiment of a hybrid insert 743 is that has a cap 733 with lower recesses 737 which can be used to extract the hybrid insert 743 from the bone. The cap 733 has a flat upper surface and vertical side surfaces, which can be used to position the implant on the bone. With reference to FIG. 109, an embodiment of a hybrid insert 745 is that has a cap 735 with lower recesses 737 which can be used to extract the hybrid insert 745 from the bone. The cap 735 has a rounded upper surface, which can be used to position the implant on the bone.

Figure 110:
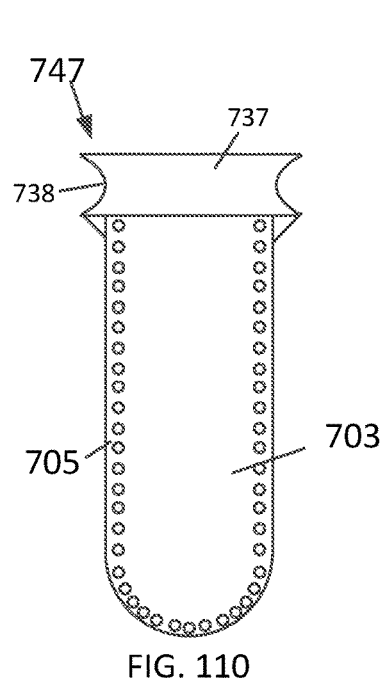
FIGS. 110-111 illustrate an embodiment of a modular hybrid insert.
Figure 111:
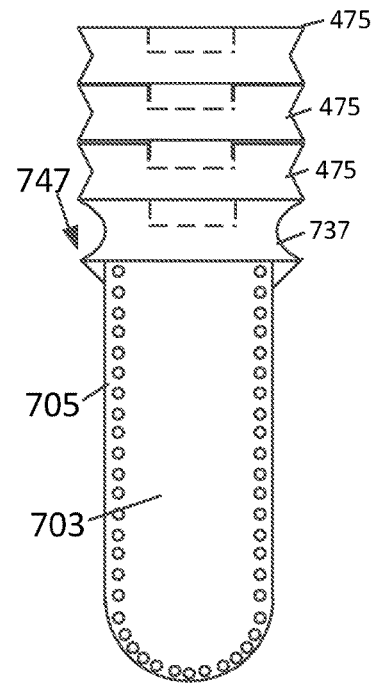

With reference to FIGS. 110 and 111, an embodiment of a modular hybrid insert 747 with PMMA spacers 475 is illustrated. The cap 737 has recesses 738 which can be used to extract the hybrid insert 745 from the bone. If the cap 737 thickness of the hybrid tack insert 747 does not provide a sufficient offset, one or more PMMA spacers 475 can be attached to the top surface of the cap 737, as described above with reference to FIGS. 75-77. FIG. 111 shows the modular hybrid insert 747 with three PMMA spacers 475 attached to the cap 738.

Figure 112:
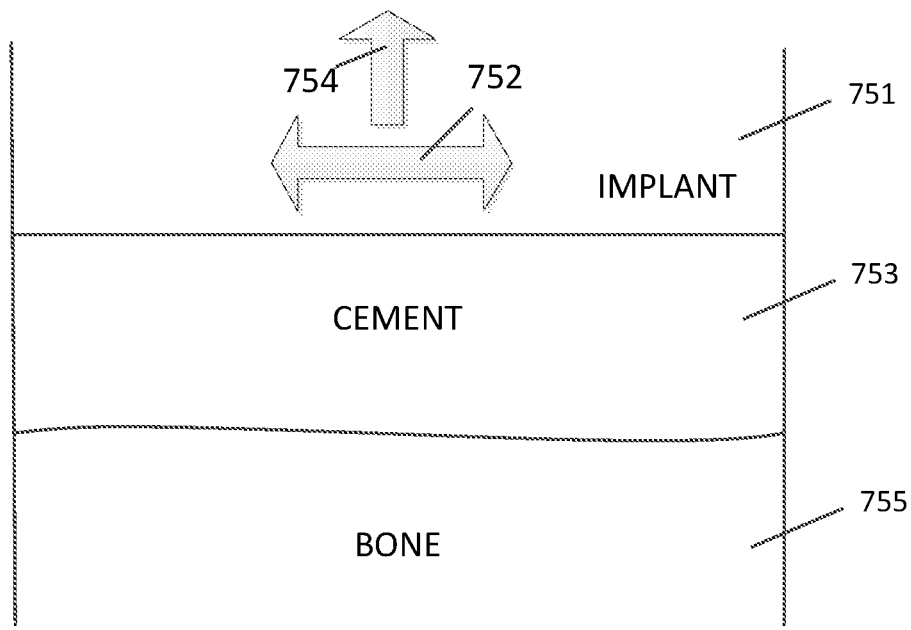
FIG. 112 illustrates an embodiment of a bone implant attached to bone with PMMA cement.
Figure 113:
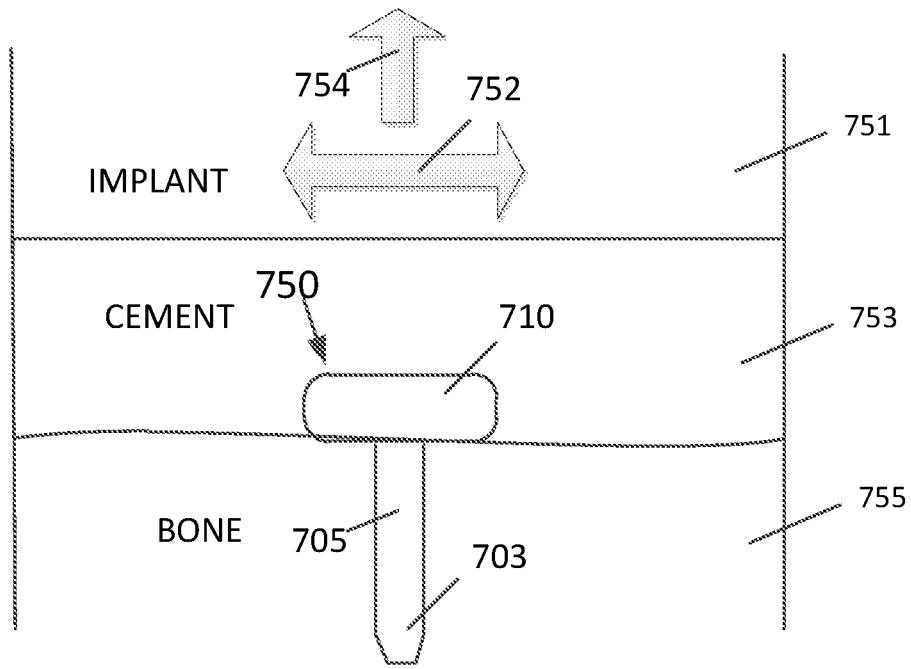
FIGS. 113 and 114 illustrate embodiments of bone implants attached to bone with PMMA cement and a hybrid insert.

With reference to FIG. 112, implants 751 have been attached to bones 755 with PMMA cement 753. A problem with this structure is that it can be weak in resistance to shear forces 752 and tension forces 754. In addition repetitive forces over prolonged periods of time can lead to bone remodeling at the interface of the cement and the bone which leads to loosening. If a shear force 752 or a tension force 754 is applied to the implant 751, the cement 753 may not have sufficient strength and adhesion to prevent a bonding failure. With reference to FIG. 113, a hybrid insert 750 has been used to improve the shear and tension strength of the implant 751 attachment to the bone 755. A stem 703 having an in-growth surface 705 inserted into the bone 755 and over time the bone will grow into the in-growth surface 705 improving the strength. Once the bone has grown to the implant, micromotion is prevent between cement and the host bone. The secure implant prevents the loosening over time which is common to most cemented implants, especially in the case of revision total joint surgery. The cap 710 can be made of cured PMMA which bonds to the PMMA cement 753. The hybrid insert 750 provides great bonding strength for the implant 751 and cement 753 to resist both shear forces 752 and tension forces 754.

Cemented implants typically have there greatest strength and bonding to the host bone at the time of implantation. Non-cemented implants are weakest from the time of implantation until the bone has ingrown to the implant. This invention provides for the stability of cemented implants at early time points with the improved longevity at the bone interface of non-cemented implants. Cemented implants offer many advantages over non-cemented in more closely matching the mechanical properties of the host bone and modulus of elasticity. More anatomic force transmission reduces stress shielding and subsequent adverse bone remodeling effects. However the implants frequently expected to perform for decades and over that time cemented implants are prone to loosening at the bone interface. The mechanical implants that bridge the interface offer the sustained mechanical resistance to tension and shear that can reduce micro motion and reduce the long term rates of loosening.

Figure 114:
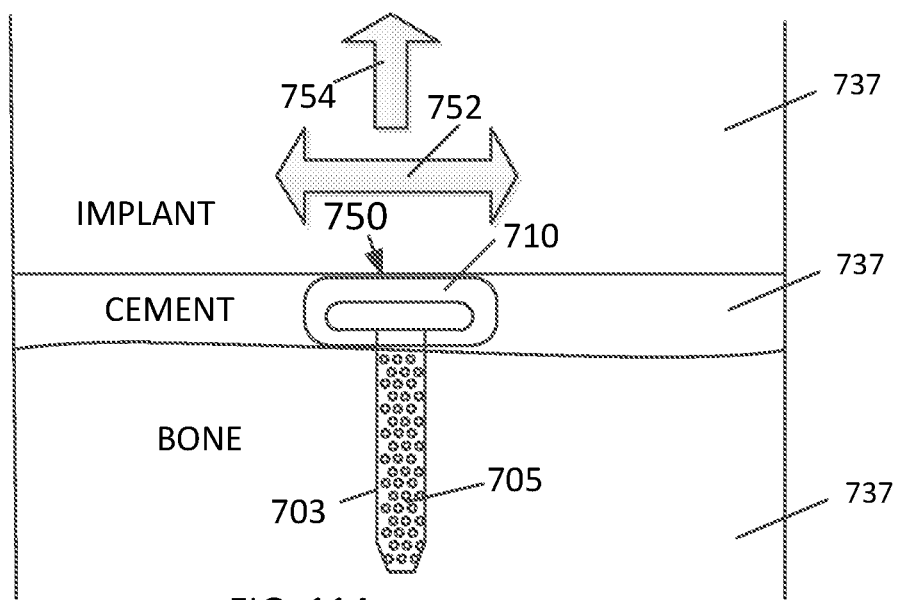

With reference to FIG. 114, a hybrid insert 750 has been used to function as a positioning spacer for an implant 751 attached to a bone 755 as well as improve the shear and tension strength of the implant 755. The implant 751 can be placed in direct contact with the upper surface of the hybrid insert 750 so that the implant 751 is held in a proper position while the cement 753 cures. This positioning functionality can be very beneficial because the liquid PMMA cement 753 may not be able to hold the implant 751 in place alone resulting in improper implant positioning when the PMMA cement 753 cures. The long duration for cement curing and need to position cemented implants at an accurate position within a mm is frequently difficult to achieve for many clinical situations such as a large acetabular cavitary defect or cementing into a cage construct or oversized cup. During the cementing process the implant has a tendency to migrate.

Figure 115:
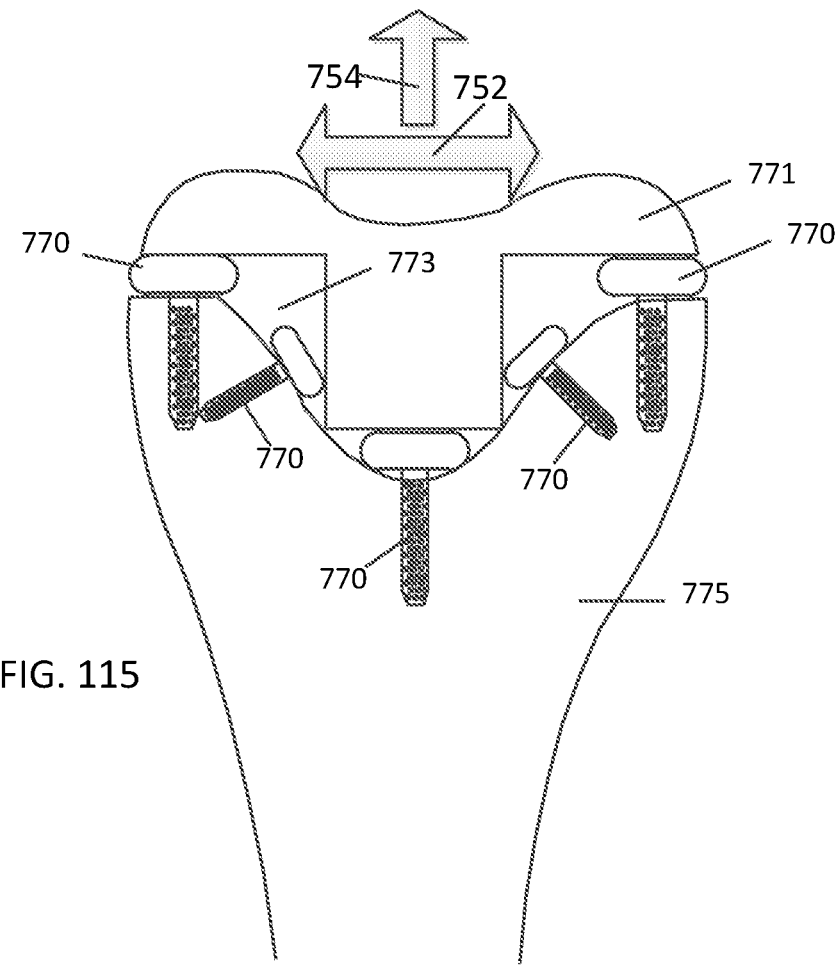
FIG. 115 illustrates an embodiment of a bone implant attached to bone with PMMA cement and hybrid inserts.

With reference to FIG. 115, another example of hybrid inserts 770 used as spacers to hold the implant 771 in a proper orientation to the bone 775 while the liquid PMMA cement cures 773. In this example, the hybrid inserts 770 on the edges and center hold the implant 771 in a proper vertical position relative to the bone 775 while the angled hybrid inserts 770 hold the implant 771 in a proper horizontal position relative to the bone 775. As discussed, the stems 703 of the hybrid inserts 770 can have in-growth surface 705 inserted into the bone 755 and over time the bone will grow into the in-growth surface 705 improving the strength. The caps 710 can be made of cured PMMA which bonds to the PMMA cement 773. The hybrid insert 770 provides great bonding strength for the implant 771 and cement 773 to resist both shear forces 752 and tension forces 754 applied to the implant 771. In addition to resisting shear forces 752 and tension forces 754, the hybrid insert 770 is also more resistant to torsional forces that are applied around the center axis of the hybrid insert 770.

Figure 116:
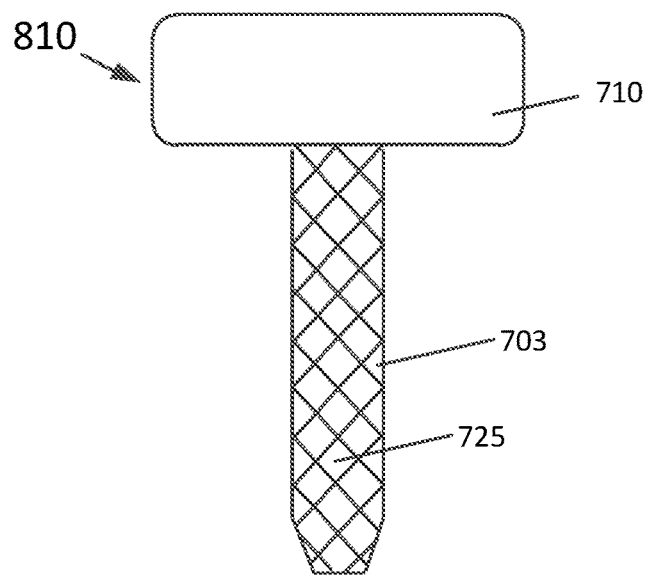
FIG. 116 embodiments of a hybrid insert with a stem having bone ingrowth surfaces.

The hybrid inserts shown in FIGS. 116-120 have a plurality of recesses that provide bone ingrowth and/or ongrowth. With reference to FIG. 116, in other embodiments, the hybrid insert 810 can include a stem 703 that has many surface grooves or knurled surface features 725, which can promote ingrowth and/or ongrowth. In the illustrated embodiment, the stem has a diamond knurled surface features 725 pattern that can be formed in a metal substrate material that is compatible with bone such as titanium and tantalum. In other embodiments, the surface features can be one of any type of surface features that promote ingrowth or ongrowth. The cap 710 of the hybrid insert 810 can have a cured PMMA surface, which can be pure PMMA or cured PMMA bonded to a metal substrate of the stem 703.

Figures 117, 118:
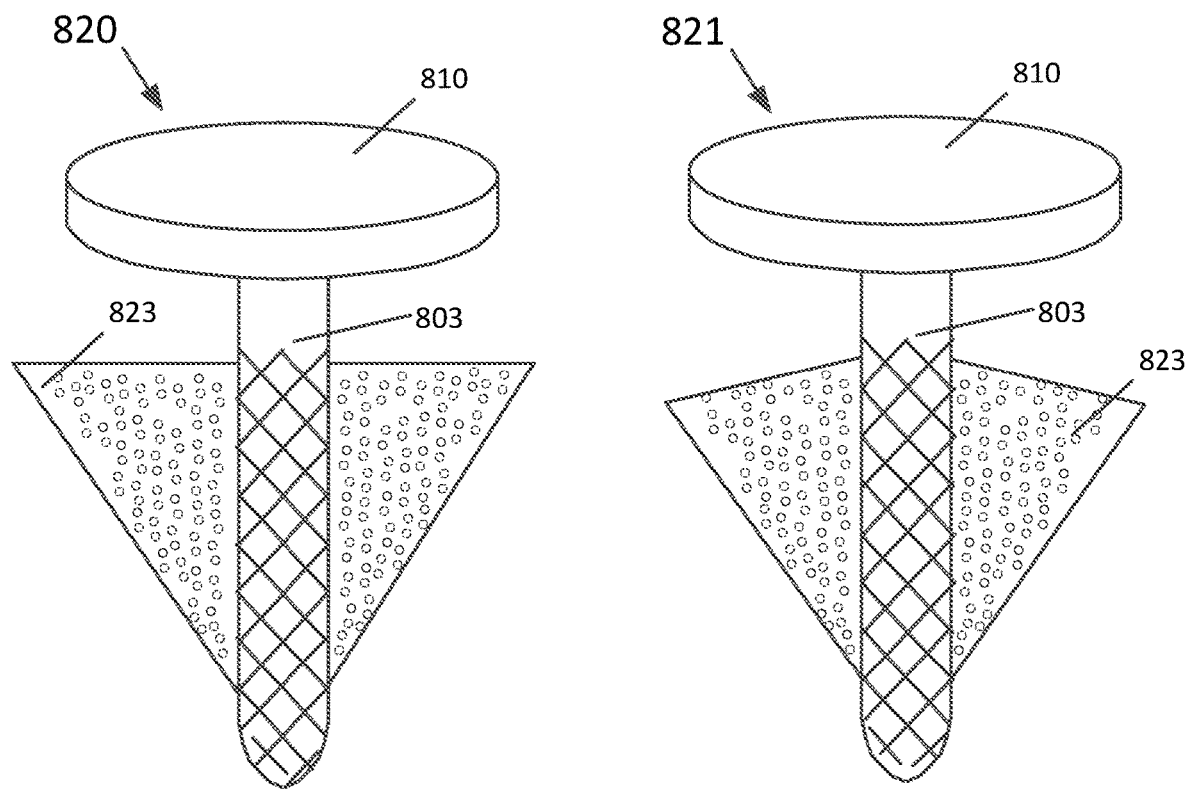
FIGS. 117 and 118 illustrate perspective views of hybrid inserts with a stem and wings having bone ingrowth surfaces.

With reference to FIGS. 117 and 118, embodiments of a hybrid insert are illustrated. In these embodiments, "wings" 823 can be attached to the stem 803 portion of the hybrid inserts. The stems 803 and the wings 823 provide ingrowth surfaces. The stems 803 and the wings 823 are inserted into the bone and the larger surface area of the wings 823 enhance binding to the bone over time. The wings 823 can be tapered to allow them to be more easily inserted into the bone like an arrowhead. The stems 803 can be pressed into the bone with the caps 810 can rest against the outer surface of the bone. The upper surface of the cap 810 can be made of cured PMMA which can provide a strong bond to the liquid PMMA cement used to secure the bone implant to the bone. The cured PMMA cap 810 can also provide a support surface for a bone implant as described above. FIG. 117 illustrates a hybrid insert 820 having wings 823 that are symmetrically aligned on opposite sides of the stem 803. The wings 823 can be in a common plane that is parallel to the center axis of the stem 803. FIG. 118 illustrates a hybrid insert 821 having wings 823 that are asymmetrically configured on opposite sides of the stem 803. The wings 823 can be each define different planes that each parallel to the center axis of the stem 803.

While the wings 823 have been illustrated as having a specific size and shape, one of ordinary skill in the art would recognize that the wings 823 can have any other suitable size or shape. In some embodiments wings 823 can function to prevent the removal of the hybrid insert 820 from the bone. In other embodiments, other structures or features of the hybrid inserts can be used to prevent removal from the bone. These structures can include anchors, barbs, friction devices, and other retention devices.

Figure 119:
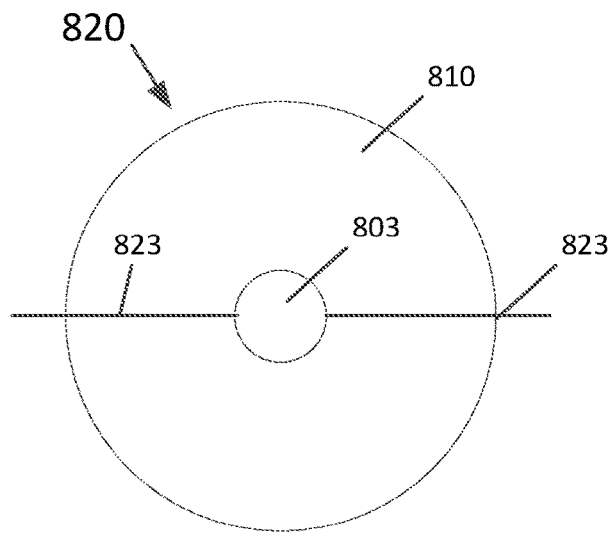
FIGS. 119-122 illustrate bottom views of hybrid inserts with a stem and wings.
Figure 120:
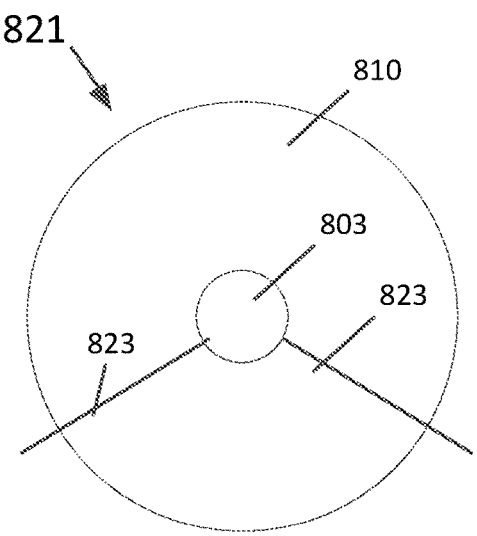
Figure 121:
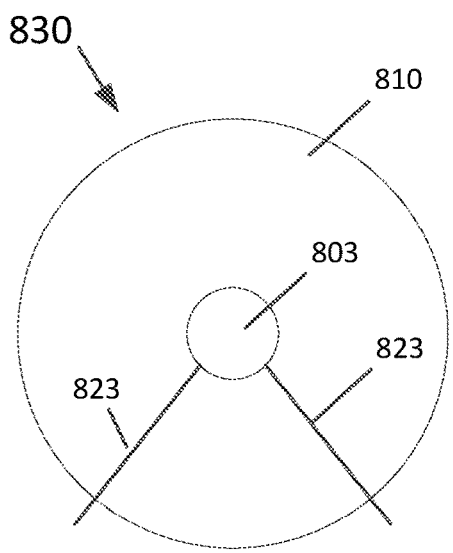
Figure 122:
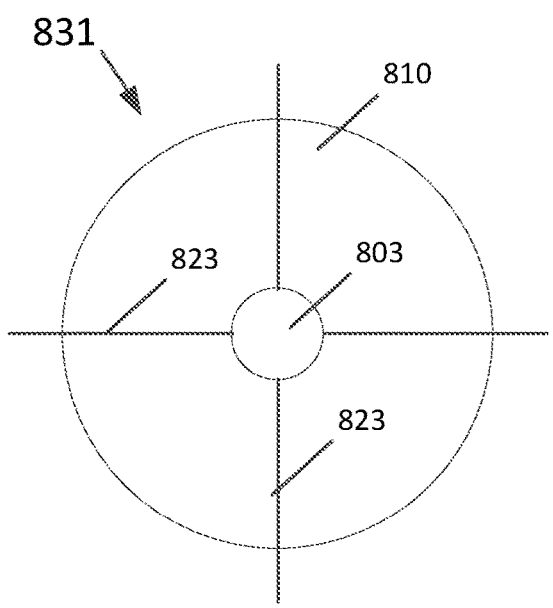

FIGS. 119-122 illustrate bottom views of different hybrid inserts. FIG. 119 illustrates a bottom view of the hybrid inserts 820 shown in FIG. 126 with the wings 823 that are symmetrically aligned on opposite sides of the stem 803. FIG. 120 illustrates a bottom view of the hybrid inserts 820 shown in FIG. 118 with the wings 823 that are asymmetrically configured on opposite sides of the stem 803 and form an obtuse angle. FIG. 121 illustrates a bottom view of an embodiment of a hybrid inserts 830 with the wings 823 that are asymmetrically configured on opposite sides of the stem 803 that form an acute angle. FIG. 122 illustrates a bottom view of the hybrid inserts 831 with four wings 823 that are symmetrically configured around the stem 803. In other embodiments, the hybrid inserts can have any number of wings and angles between the wings.

Figure 123:
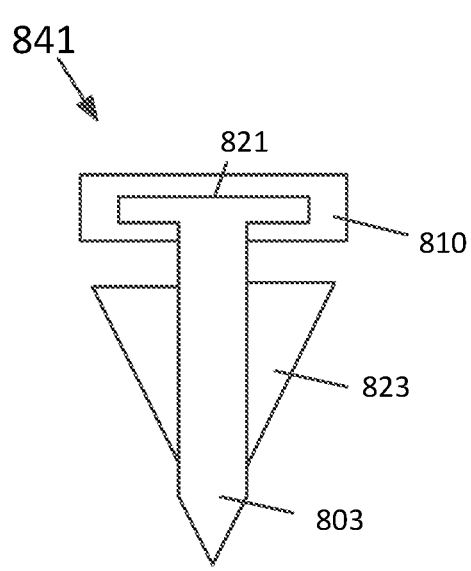
FIGS. 123-126 illustrate side views of different embodiments of hybrid inserts with a stem and wings where the cap is surrounded by different PMMA shapes.

With reference to FIG. 123, a cross section side view of an embodiment of a hybrid insert 841 is illustrated. The hybrid insert 841 has a stem 803, wings 823 and a cap 810. In this embodiment, the stem 803 made of a material and surface features that promotes bone ingrowth and/or ongrowth. The hybrid insert 841 can have a metal stem 803 such as titanium or tantalum. A metal cap 821 can be encapsulated so that exposed surfaces of the cap 810 are completely covered with PMMA material. In this embodiment, the upper surface of the PMMA material can be a planar surface. As discussed, the ingrowth surfaces in the stem 803 and wings 823 can be grooves or other holes or indentations that are 40-800 microns in diameter, width and/or depth. The stem 803 and wings 823 are inserted into the bone. Over time, the bone grows into the ingrowth surface features on the stem 803 and wings 823 strengthening the bond between the bone and insert 841. Cement is used to attached the bone implant to the bone. The bone implant can be pressed against the top of the hybrid insert 841 and the cement forms a strong bond with the PMMA surfaces of the cap 810.

In some situations it may be necessary to remove the hybrid insert 841 from the bone. The bone implant and cement can be removed from the bone. The PMMA coating can be removed from the metal cap 821. The removal of the PMMA coating can expose an opening at a lower surface of the metal cap 821. A tool similar to a nail puller on a hammer can be placed between the lower surface of the metal cap 821 and the bone. The tool can be used to pull the metal cap 821 and hybrid insert 841 from the bone.

Figure 124:
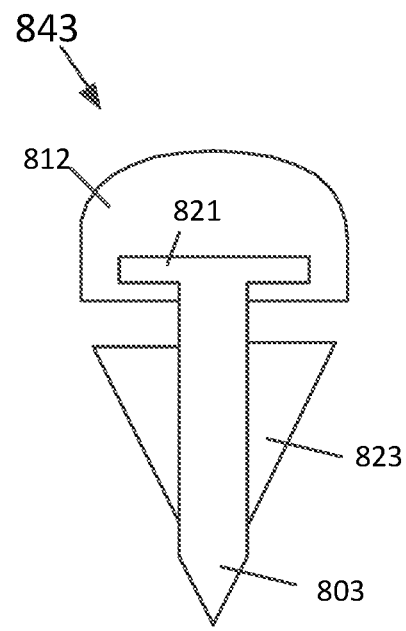

As discussed, the hybrid inserts can be used to properly position the bone implants. It can be useful to use different cap shapes to properly position the bone implants. For example, with reference to FIG. 124 illustrates a hybrid insert 843 which has a rounded cap 812 which can be molded to the metal cap 821 at the top of the stem 803. The lower portion of the hybrid insert 843 is similar to the lower portion of the hybrid insert described above in FIG. 123.

Figure 125:
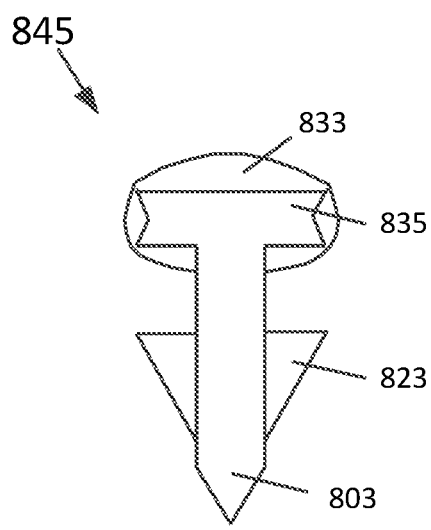

With reference to FIG. 125, another embodiment of a hybrid insert 845 is illustrated. The stem 803 can be attached to a metal cap 835 that has recessed side surfaces around the perimeter of the metal cap 835 which can be used to extract the hybrid insert 845 if the PMMA material 833 surrounding the cap 835 is removed. The lower portion of the hybrid insert 843 is similar to the lower portion of the hybrid insert described above in FIG. 123.

Figure 126:
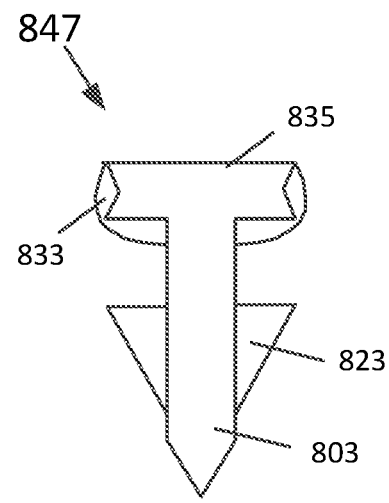

With reference to FIG. 126, an embodiment of a hybrid insert 847 is illustrated which has a metal cap 835 that has recessed side surfaces around the perimeter of the metal cap 835 which can be used to extract the hybrid insert 845 if the PMMA material 833 surrounding the cap 835 is removed. The upper surface of the metal cap 835 is not covered with PMMA. In this embodiment, a downward force can be applied to the upper surface of the metal cap 835 to drive the hybrid insert 847 into the bone. For example, a tool such as a hammer can be used to tap the hybrid insert 847 into the bone. The upper surface of the metal cap 835 can contact the inner surface of the bone implant. The PMMA material 833 can surround the perimeter and lower surface of the cap 835 which can bond to the liquid PMMA cement that is applied to the bone, cap 835 and inner surfaces of the bone implant. The lower portion of the hybrid insert 847 is similar to the lower portion of the hybrid insert described above in FIG. 123.

Figure 127:
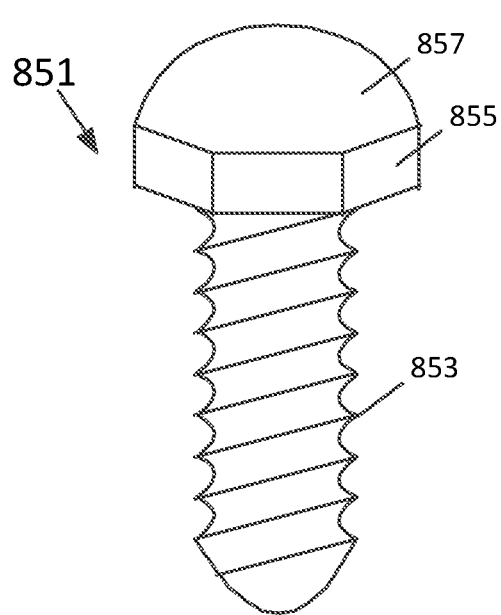
FIGS. 127 and 128 illustrate perspective views of embodiments of threaded stem hybrid inserts.
Figure 128:
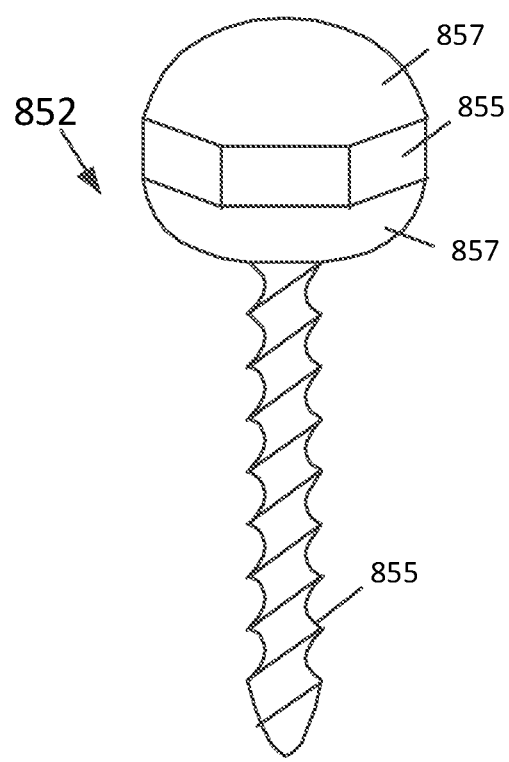

With reference to FIGS. 127 and 128, different embodiments of hybrid inserts are illustrated which have threaded stems and caps with rotational driving surfaces. With reference to FIG. 127, a hybrid insert 851 includes a threaded stem 853 that includes ingrowth surface features as described above. The ingrowth surface features can include holes, grooves or other features that are 40-800 microns diameter, width and/or depth. The threaded stem 853 can be integrally coupled to the rotational driving surfaces 855. In this embodiment the rotational driving surfaces 855 are hexagonal outer driving surfaces of the cap 810. Cured PMMA material 857 can be attached to the upper surface of the cap 810.

When the hybrid insert 851 is needed, the bone can be drilled and the tip of the hybrid insert 851 can be placed in the hole entrance. A driving tool such as a hex wrench can be used to rotate the hybrid insert 851 so that the threaded stem 853 contacts the inner surface of the bone hole and the hybrid insert 851 is driven into the bone hole. The hybrid insert 851 can be rotated until the cap 810 is properly positioned relative to the bone surface to properly support the bone implant. The hybrid insert 851 can be further rotated clockwise or counter clockwise if adjustments need to be made. Once the hybrid inserts 851 are properly positioned in the bone, liquid PMMA cement can be placed on the bone and hybrid inserts 851. The bone implant can be placed in the cement and pressed against the caps 810 of the hybrid inserts 851. The liquid PMMA cement strongly bonds to the cured PMMA material 857 on the hybrid insert 851. Over time, the bone grows into the bone ingrowth surfaces of the threaded stem 853 which increases the strength of the bone to hybrid inserts 851 connection. If the hybrid inserts 851 ever needs to be removed, the bone implant and PMMA cement can be removed from the bone. The hex tool can then be used to remove the hybrid insert 851 from the bone.

FIG. 128 illustrates a hybrid insert 852 that is similar to the hybrid insert shown in FIG. 127 with a threaded stem 855 that is narrower in diameter. The threaded stem 855 is coupled to a cap 810 that has a hexagonal outer driving surface. The threaded stem 855 can be self tapping so a bone hole may not be necessary. In this embodiment, the cured PMMA material 857 can be attached to the upper and lower surfaces of the cap 810.

When the hybrid insert 852 is needed, the tip of the hybrid insert 851 can be placed against the bone. A driving tool such as a hex wrench can be used to rotate the threaded stem 853 to drive the hybrid insert 852 into the surface of the bone and the hybrid insert 851 is driven into the bone. The hybrid insert 852 can be rotated until the cap 810 is properly positioned relative to the bone surface to properly support the bone implant and further rotated clockwise or counter clockwise if adjustments need to be made. Once the hybrid inserts 852 are properly positioned in the bone, liquid PMMA cement can be placed on the bone and hybrid inserts 852. The bone implant can be placed in the cement and pressed against the caps 810 of the hybrid inserts 851. The liquid PMMA cement strongly bonds to the cured PMMA material 857 on the hybrid insert 851. Over time, the bone grows into the bone ingrowth surfaces of the threaded stem 853, which increases the strength of the bone to hybrid inserts 852 connection. If the hybrid insert 852 ever needs to be removed, the bone implant and PMMA cement can be removed from the bone. The hex tool can then be used to remove the hybrid inserts 852 from the bone.

Figure 129:
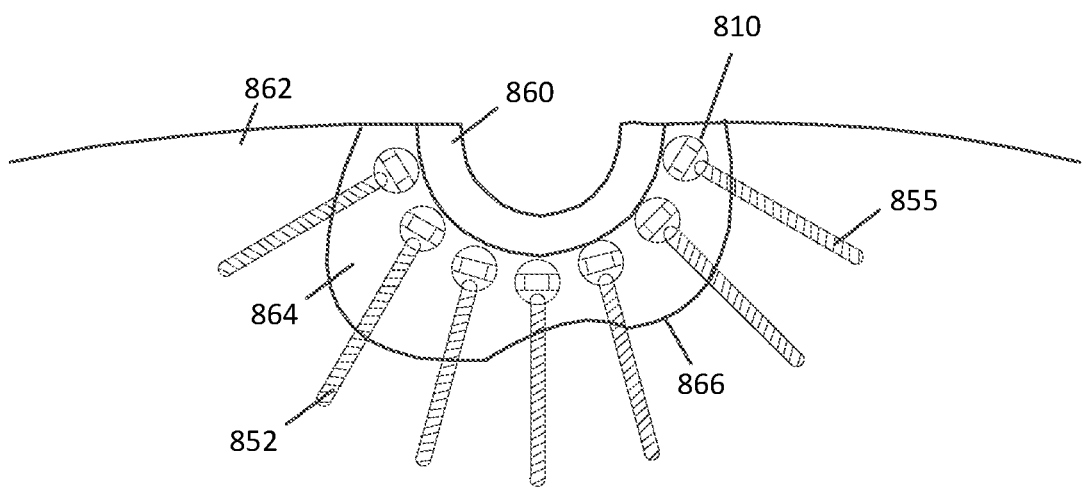
FIG. 129 illustrates a bone implant positioned on a bone with threaded stem hybrid inserts.

FIG. 129 illustrates an example of how the hybrid inserts 852 can be placed in a bone 862 and used to position and support a bone implant 860 in a recessed volume 862. In this example, the bone 862 has a recessed surface 866. The hybrid inserts 852 can be screwed into the recessed surface 866 with the caps 810 positioned to support the bone implant 860. The hybrid inserts 852 are can be rotated with a hex wrench tool to match the outer surfaces of the bone implant 860. Once the hybrid inserts 852 are properly positioned, liquid PMMA cement 864 can be placed into the recessed surface 866 and around the hybrid inserts 852. The bone implant 860 can then be placed against the caps 810, which support the bone implant 860 as the PMMA cement cures. The PMMA cement 864 forms a strong bond with the cured PMMA on the cap 810 as well as the textured surfaces of the threaded stem. Over time the bone 862 grows into the ingrowth surfaces of the threaded stem 855 further increasing the strength of the bond between the bone 862 and the hybrid inserts 852.

Figure 130:
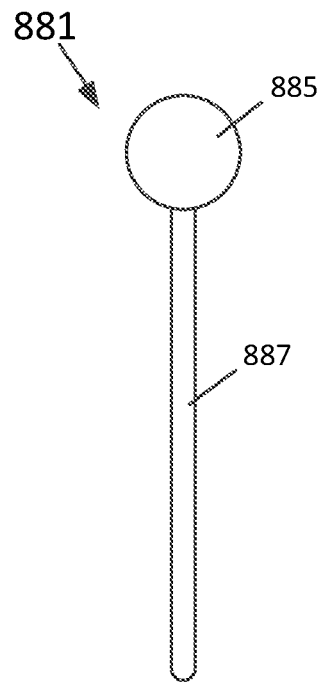
FIG. 130 illustrates a hybrid insert with a thin stem and a rounded PMMA head.
Figure 131:
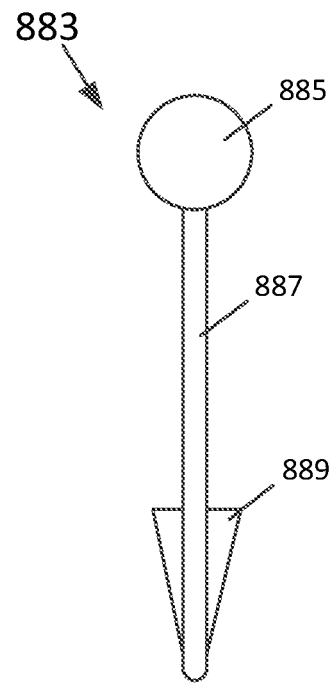
FIG. 131 illustrates a hybrid insert with a thin stem with wings and a rounded PMMA head.

With reference to FIG. 130, an embodiment of a hybrid insert 881 is illustrated that includes a stem 887 coupled to a cured PMMA head 885 which can have rounded outer surfaces. The stem 887 can have ingrowth surfaces that can include grooves or other holes or indentations that are 40-800 microns in diameter, width and/or depth. The hybrid inserts 881 can be pressed into the bone so that the positions of the heads 885 which can support a bone implant. With reference to FIG. 131, an embodiment of a hybrid insert 883 is illustrated that includes a stem 887 having wings 889 coupled to a cured PMMA head 885. The stem 887 and wings 889 can have ingrowth surfaces.

Figure 132:
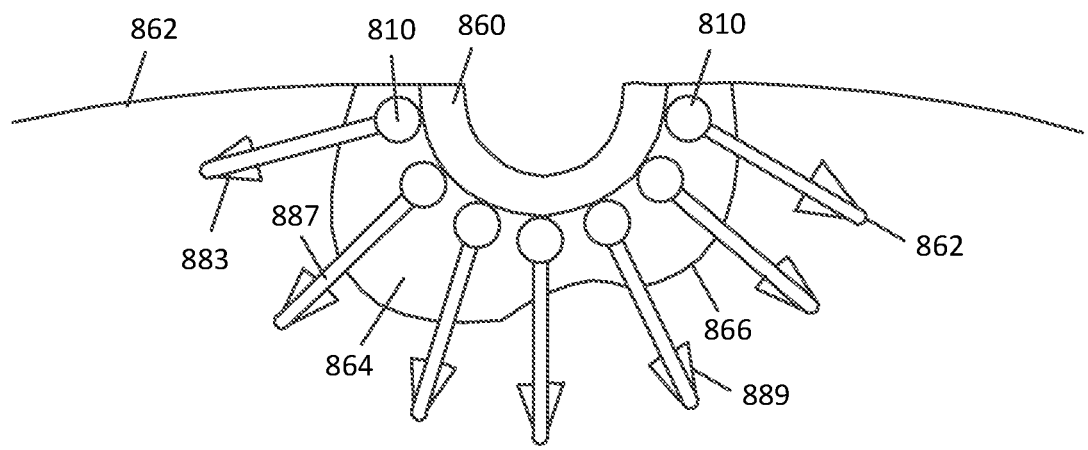
FIG. 132 illustrates a bone implant positioned on a bone with thin stem with wings hybrid inserts.

FIG. 132 illustrates an example of how the hybrid inserts 883 can be placed in a bone 862 and used to position and support a bone implant 860 in a recessed surface 866. In this example, the bone 862 has a recessed surface 866. The hybrid inserts 883 can be pressed into the recessed surface 866 with the caps 810 positioned to support the bone implant 860 and match the outer surfaces of the bone implant 860. Once the hybrid inserts 883 are properly positioned, liquid PMMA cement 864 can be placed into the recessed surface 866 and around the hybrid inserts 883. The bone implant 860 can then be placed against the caps 810 as the PMMA cement cures. The PMMA cement 864 forms a strong bond with the cured PMMA on the cap 810 as well as the textured surfaces of the threaded stem. Over time the bone 862 grows into the ingrowth surfaces of the stem 887 further increasing the strength of the bond between the bone 862 and the hybrid inserts 883.

Figure 133:
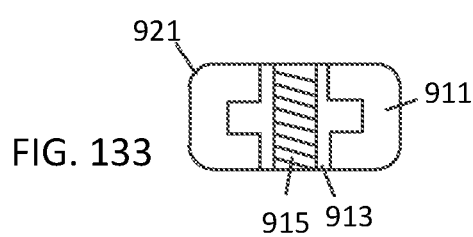
FIG. 133 illustrates a side view of an embodiment of a PMMA outer surface cap.
Figure 137:
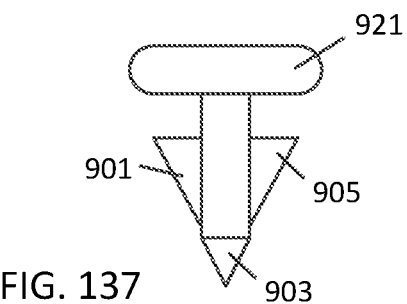
FIGS. 136-140 illustrates a side view of an embodiment of an assembled hybrid insert with wings.
Figure 134:
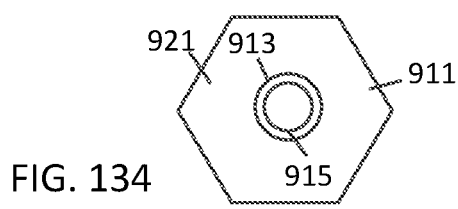
FIG. 134 illustrates a top view of an embodiment of a PMMA outer surface cap.
Figure 138:
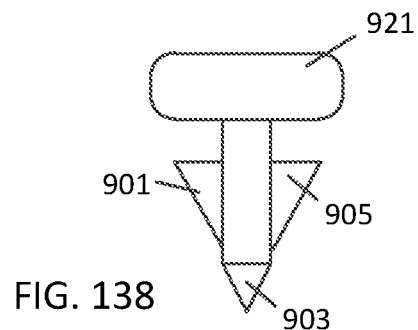
Figure 135:
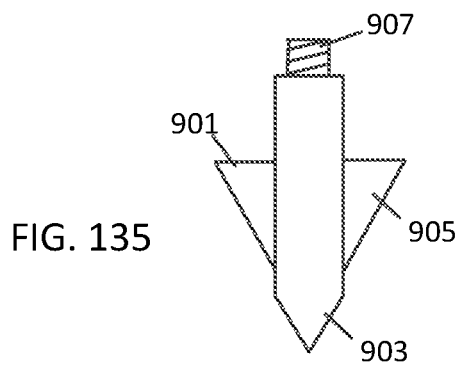
FIG. 135 illustrates a side view of an embodiment of a stem assembly with wings.
Figure 139:
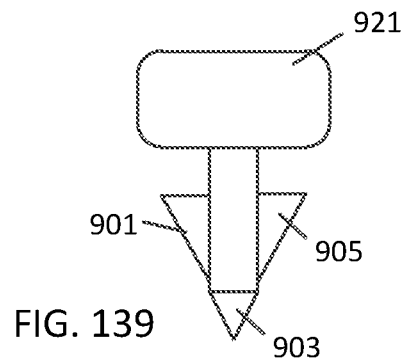
Figure 136:
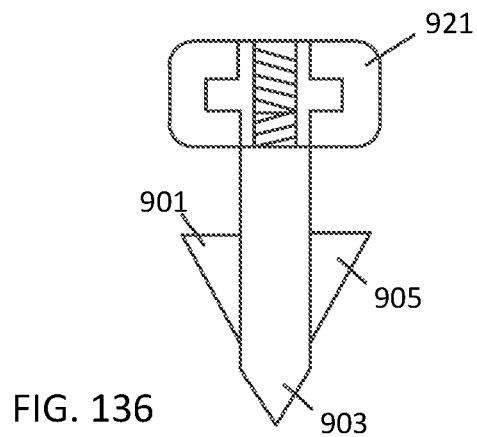
Figure 140:
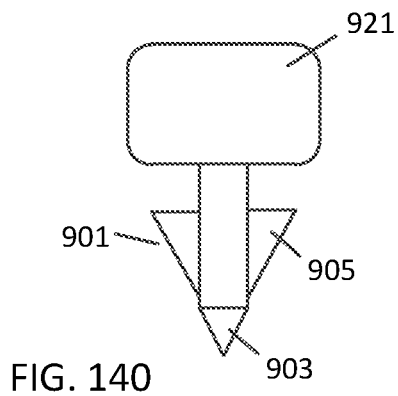

With reference to FIGS. 133-140, a modular hybrid insert is illustrated that includes a stem unit and a cap. As discussed, the hybrid insert can be used to position the bone implant at an offset relative to the surface of the bone. This positioning must be very accurate for successful bone implant functionality. As discussed, it very desirable to be able to adjust the offset of the hybrid insert relative to the bone surface. In this embodiment, the system uses a common stem assembly that can be coupled to various caps having different thicknesses. With reference to FIG. 133, a cross section view of an embodiment of a cap 921 is shown. The cap 921 can include a internal piece 913 having a threaded hole 915 and a cured PMMA 911 formed around the internal piece 913. The internal piece 913 can be made of a metal such as titanium or tantalum or any other suitable material. FIG. 134 illustrates a top view of the cap 921. FIG. 135 illustrates a side view of the stem assembly 901 is illustrated which includes a stem 903, wings 905 attached to the stem 903 and a threaded portion 907 attached to the top of the stem 903. The stem 903 and wings 905 can have bone ingrowth surface features with 40-800 micron depth: recesses, grooves, or other surface features such as diameter, width and/or depth. The stem assembly 901 can be made of titanium or tantalum. With reference to FIG. 136, the assembled hybrid insert is illustrated with the cap 921 screwed onto the threaded portion 907 of the stem assembly. In an embodiment, the stem assembly 901 can be placed into the bone and then the proper thickness offset can be determined. The cap 921 having the proper thickness offset can then be screwed onto the threaded portion of the stem assembly 901. The wings 905 prevent the stem 903 from rotating when the cap 921 is screwed onto the stem 903. If an offset thickness error is determined, the cap 921 can be removed and replaced with another cap having the correct offset thickness. If the stem assembly needs a removal tool having a female thread corresponding to the threaded portion 907 can be used to FIGS. 137-140 illustrate stem assemblies coupled to caps having different cap 921 thickness offsets.

With reference to FIGS. 141-145 another embodiment of a modular hybrid insert system that can be used for bone implants is illustrated. The modular hybrid insert can have a stem assembly and a variety if different offset thickness caps. FIG. 141 illustrates a cross section side view of a cap 931 that has a rounded outer hemispherical shape. The cap 931 includes an internal volume 933 and passageways 935 between the outer surface of the cap 931 and the internal volume 933. The lower surface of the cap 931 can be a layer of metal such as titanium, tantalum or any other suitable material. With reference to FIG. 142, a bottom view of a cap 931 is shown. The lower surface of the cap 931 has a slot 941 that extends into the internal volume 933. With reference to FIG. 143, a stem 941 can be inserted into the bone 945 and a T portion 943 attached to the top of the stem 941 can extend out of the surface of the bone 945. The slot 941 can be aligned with the T portion 943. The cap 931 can placed over the T portion 943 as shown in FIG. 144. The cap 931 can then be rotated 90 degrees so that the T portion 943 is out of alignment with the slot 941 as shown in FIG. 145. If the cap offset height needs to be changed, the cap can be removed and replaced with a proper offset thickness. Once the proper thickness caps have been installed on the T portions 943, liquid PMMA cement can be applied to the caps 931 between the bone 945. The PMMA cement can pass through the passageways 935 into the internal volume 933. The PMMA cement can cure to secure the T portion 943 in an out of aligned position relative to the slot 941. The bottom surface 949 of the cap 931 and the stem 941 can have bone ingrowth surface features as described above. Over time, after the stem 941 is inserted and the cap 931 is installed, the bone 945 can grow into the ingrowth surface features to more rigidly secure the hybrid insert to the bone 945.

In the described embodiments, the stem diameters can range from 3 mm to 10 mm and the caps can have a width and thickness between 3 mm and 20 mm.

The present disclosure, in various embodiments, includes components, and apparatus substantially as depicted and described herein, including various embodiments, sub-combinations, and subsets thereof. Those of skill in the art will understand how to make and use the present disclosure after understanding the present disclosure. The present disclosure, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation. Rather, as the flowing claims reflect, inventive aspects lie in less than all features of any single foregoing disclosed embodiment.

What is claimed is:

1. A hybrid bone insert comprising:
   a metal elongated stem having outer surfaces that have bone ingrowth features wherein the elongated stem is adapted to be inserted into a living bone and over time the living bone grows into the bone ingrowth features on the elongated stem; and
   a cap that is molded to the metal elongated stem, wherein an outer surface of the cap is formed from cured polymethyl methacrylate (PMMA) which hardens in a mold to bond the cap to the metal elongated stem;
   wherein the metal elongated stem has an interior volume which is filled with the cured PMMA.

2. The hybrid bone insert of claim 1 wherein an outer perimeter portion of the cap includes a concave surface.

3. The hybrid bone insert of claim 1 wherein the bone ingrowth features include grooves, recesses or protrusions which are 40-800 microns in width and depth.

4. The hybrid bone insert of claim 1 wherein the bone ingrowth features include pores which are 40-800 microns in diameter.

5. The hybrid bone insert of claim 1 wherein the bone ingrowth features include holes which are 40-800 microns in diameter.

6. The hybrid bone insert of claim 1 wherein an upper surface and a lower surface of the cap are planar and parallel.

7. The hybrid bone insert of claim 1 wherein a diameter of the metal elongated stem is 3 mm to 10 mm.

8. The hybrid bone insert of claim 1 wherein a width of the cap is 3 mm to 20 mm.

9. The hybrid bone insert of claim 1 wherein a thickness of the cap is 3 mm to 20 mm.

10. The hybrid bone insert of claim 1 further comprising:
    a plurality of PMMA spacers attached to the cap to increase an offset distance of the hybrid bone insert.

11. A hybrid bone insert comprising:
    a metal elongated stem having outer surfaces that have bone ingrowth features and a coupling mechanism on a proximal portion, wherein the metal elongated stem is adapted to be inserted into a living bone and over time the living bone grows into the bone ingrowth features on the metal elongated stem; and
    a first cap that is molded to the coupling mechanism on the proximal portion of the metal elongated stem, wherein an outer surface of the cap is formed from cured polymethyl methacrylate (PMMA) which hardens in a mold to bond the cap to the metal elongated stem;
    wherein an outer perimeter portion of the cap includes a concave surface.

12. The hybrid bone insert of claim 11 wherein the coupling mechanism includes a threaded rod and a threaded bore.

13. The hybrid bone insert of claim 11 wherein the coupling mechanism includes a slot and an internal volume in the cap and a "T" shaped feature at a proximal portion of the stem.

14. The hybrid bone insert of claim 13 wherein the metal elongated stem has an interior volume which is filled with the cured PMMA.

15. The hybrid bone insert of claim 11 wherein the bone ingrowth features include grooves, trabeculations, or recessed holes which are 40-800 microns in width and depth.

16. The hybrid bone insert of claim 11 wherein a diameter of the metal elongated stem is 3 mm to 10 mm.

17. The hybrid bone insert of claim 11 wherein a width of the cap is 3 mm to 20 mm.

18. The hybrid bone insert of claim 11 wherein a thickness of the cap is 3 mm to 20 mm.

\* \* \* \* \*